(12) United States Patent
Heffernan et al.

(10) Patent No.: US 9,234,046 B2
(45) Date of Patent: Jan. 12, 2016

(54) TREATMENT OF RENAL DISEASE

(75) Inventors: Mark Heffernan, Dublin (IE); Luke O'Neill, Dublin (IE); Peter McGuirk, Clonee (IE); Brian Keogh, Clondalkin (IE); Christopher Locher, Lexington, MA (US)

(73) Assignee: OPSONA Therapeutics Ltd, Dublin (IE)

( * ) Notice: Subject to any disclaimer, the term of this patent is extended or adjusted under 35 U.S.C. 154(b) by 29 days.

(21) Appl. No.: 13/526,873

(22) Filed: Jun. 19, 2012

(65) Prior Publication Data

US 2012/0258103 A1  Oct. 11, 2012

Related U.S. Application Data

(63) Continuation of application No. 12/667,450, filed as application No. PCT/EP2008/058732 on Jul. 4, 2008, now abandoned.

(60) Provisional application No. 61/038,304, filed on Mar. 20, 2008.

(30) Foreign Application Priority Data

Jul. 5, 2007 (IE) .................................... 2007/0486

(51) Int. Cl.
| | |
|---|---|
| A61K 39/395 | (2006.01) |
| C07K 16/28 | (2006.01) |
| C07K 14/705 | (2006.01) |
| A61K 45/06 | (2006.01) |
| A61P 13/12 | (2006.01) |
| C12N 5/07 | (2010.01) |
| A61K 38/00 | (2006.01) |
| A61K 39/00 | (2006.01) |

(52) U.S. Cl.
CPC ............. C07K 16/2896 (2013.01); A61K 45/06 (2013.01); C07K 14/70596 (2013.01); *A61K 38/00* (2013.01); *A61K 2039/505* (2013.01); *G01N 2500/02* (2013.01)

(58) Field of Classification Search
None
See application file for complete search history.

(56) References Cited

U.S. PATENT DOCUMENTS

| | | |
|---|---|---|
| 7,202,234 B2 | 4/2007 | Chow et al. |
| 2006/0165686 A1 | 7/2006 | Elson et al. |
| 2010/0278817 A1 | 11/2010 | Heffernan et al. |

FOREIGN PATENT DOCUMENTS

| | | |
|---|---|---|
| EP | 1293566 A1 | 3/2003 |
| WO | WO 2005/079419 A2 | 9/2005 |
| WO | WO 2008132516 A1 | 11/2008 |
| WO | WO 2009000929 A2 | 12/2008 |

OTHER PUBLICATIONS

Anders et al., Signaling danger: toll-like receptors and their potential roles in kidney disease. J Am Soc Nephrol. Apr. 2004;15(4):854-67. Review.
Immunobiology, The Immune System in Health and Disease, Third Edition, Janeway and Travers, Ed. 1997, 9 total pages.
Khan et al., Antibody blockade of TNF-α reduces inflammation and scarring in experimental crescentic glomerulonephritis. Kidney International, vol. 67 (2005), pp. 1812-1820.
Leemans et al., Renal-associated TLR2 mediates ischemia/reperfusion injury in the kidney. J Clin Invest. Oct. 2005;115(10):2894-903.
Meng, et al., Antagonistic antibody prevents toll-like receptor 2-driven lethal shock-like syndromes. The Journal of Clinical Investigation, 2004, vol. 113, No. 10, pp. 1473-1481.
Pålsson-McDermott et al., The potential of targeting Toll-like receptor 2 in autoimmune and inflammatory diseases. Ir J Med Sci. Dec. 2007;176(4):253-60. Epub Nov. 15, 2007. Review.
Dragun et al., ICAM-1 antisense oligodesoxynucleotides prevent reperfusion injury and enhance immediate graft function in renal transplantation. Kidney Int. Aug. 1998;54(2):590-602.
Farrar et al., Inhibition of TLR2 promotes graft function in a murine model of renal transplant ischemia-reperfusion injury. FASEB J. Feb. 2012;26(2):799-807. Epub Oct. 31, 2011.
Friedewald et al., Inflammatory cells in ischemic acute renal failure. Kidney Int. Aug. 2004;66(2):486-91.
Kelly et al., Intercellular adhesion molecule-1-deficient mice are protected against ischemic renal injury. J Clin Invest. Feb. 15, 1996;97(4):1056-63.
Salmela et al., A randomized multicenter trial of the anti-ICAM-1 monoclonal antibody (enlimomab) for the prevention of acute rejection and delayed onset of graft function in cadaveric renal transplantation: a report of the European Anti-ICAM-1 Renal Transplant Study Group. Transplantation. Mar. 15, 1999;67(5):729-36. Abstract Only.

*Primary Examiner* — Bridget E Bunner
*Assistant Examiner* — Fozia Hamud
(74) *Attorney, Agent, or Firm* — Wolf, Greenfield & Sacks, P.C.

(57) ABSTRACT

The present invention provides compounds and methods for the treatment and prophylaxis of renal disease and inflammation. In particular the invention provides methods for the treatment of kidney disease and failure through the administration of compounds which function as inhibitors of TLR2 function and expression.

15 Claims, 29 Drawing Sheets

```
  1 mphtlwmvwv lgviislske essnqaslsc drngickgss gslnsipsgl teavksldls
 61 nnrityisns dlqrcvnlqa lvltsngint ieedsfsslg slehldlsyn ylsnlssswf
121 kplssltfln llgnpyktlg etslfshltk lqilrvgnmd tftkiqrkdf agltfleele
181 idasdlqsye pkslksiqnv shlilhmkqh illeifvdv  tssveclelr dtdldtfhfs
241 elstgetnsl ikkftfrnvk itdeslfqvm kllnqisgll elefddctln gvgnfrasdn
301 drvidpgkve tltirrlhip rfylfydlst lysltervkr itvenskvfl vpcllsqhlk
361 sleyldlsen lmveeylkns acedawpslq tlilrqnhla slektgetll tlknltnidi
421 sknsfhsmpe tcqwpekmky lnlsstrihs vtgcipktle ildvsnnnln lfslnlpqlk
481 elyisrnklm tlpdasllpm llvlkisrna ittfskeqld sfhtlktlea ggnnficsce
541 flsftqeqqa lakvlidwpa nylcdspshv rgqqvqdvrl svsechrtal vsgmccalfl
601 lilltgvlch rfhglwymkm mwawlqakrk prkapsrnic ydafvsyser daywvenlmv
661 qelenfnppf klclhkrdfi pgkwiidnii dsiekshktv fvlsenfvks ewckyeldfs
721 hfrlfeennd aailillepi ekkaipqrfc klrkimntkt ylewpmdeaq regfwvnlra
781 aiks
```

Figure 19 – SEQ ID NO:1

```
  1 mlralwlfwi lvaitvlfsk rcsaqeslsc dasgvcdgrs rsftsipsgl taamksldls
 61 fnkityiqhg dlracanlqv lmlkssrint iegdafyslg slehldlsdn hlssissswf
121 gplsslkyln lmgnpyqtlg vtslfpnltn lqtlrignve tfseirridf agltslnele
181 ikalslrnyq sqslksirdi hhltlhlses aflleifadi lssvrylelr dtnlarfqfs
241 plpvdevssp mkklafrgsv ltdesfnell kllryilels evefddctln glgdfnpses
301 dvvselgkve tvtirrlhip qfylfydlst vysllekvkr itvenskvfl vpcsfsqhlk
361 slefldlsen lmveeylkns ackgawpslq tlvlsqnhlr smqktgeill tlknltsldi
421 srntfhpmpd scqwpekmrf lnlsstgirv vktcipqtle vldvsnnnld sfslflprlq
481 elyisrnklk tlpdaslfpv llvmkirena vstfskdqlg sfpkletlea gdnhfvcsce
541 llsftmetpa laqilvdwpd sylcdspprl hghrlqdarp svlechqaal vsgvccalll
601 lillvgalch hfhglwylrm mwawlqakrk pkkapcrdvc ydafvsyseq dshwvenlmv
661 qqlensdppf klclhkrdfv pgkwiidnii dsiekshktv fvlsenfvrs ewckyeldfs
721 hfrlfdennd aailvllepi erkaipqrfc klrkimntkt ylewpldegq qevfwvnlrt
781 aiks
```

Figure 20 – SEQ ID NO:2

```
mphtlwmvwvlgviislskeessnqaslscdrngickgssgslnsips
glteavksldlsnnrityisnsdlqrcvnlqalvltsngintieedsf
sslgslehldlsynylsnlssswfkplssltflnllgnpyktlgetsl
fshltklqilrvgnmdtftkiqrkdfagltfleeleidasdlqsyepk
slksiqnvshlilhmkqhillleifvdvtssveclelrdtdldtfhfs
elstgetnslikkftfrnvkitdeslfqvmkllnqisgllelefddct
lngvgnfrasdndrvidpgkvetltirrlhiprfylfydlstlyslte
rvkritvenskvflvpcllsqhlksleyldlsenlmveeylknsaced
awpslqtlilrqnhlaslektgetlltlknltnidisknsfhsmpetc
qwpekmkylnlsstrihsvtgcipktleildvsnnnlnlfslnlpqlk
elyisrnklmtlpdasllpmllvlkisrnaittfskeqldsfhtlktl
eaggnnficsceflsftqeqqalakvlidwpanylcdspshvrgqqvq
dvrlsvsech
```

Figure 21 – SEQ ID NO:5

SEQUENCE LISTING

```
<160> NUMBER OF SEQ ID NOS: 5

<210> SEQ ID NO 1
<211> LENGTH: 784
<212> TYPE: PRT
<213> ORGANISM: Homo sapiens

<400> SEQUENCE: 1

Met Pro His Thr Leu Trp Met Val Trp Val Leu Gly Val Ile Ile Ser
1               5                  10                  15

Leu Ser Lys Glu Glu Ser Ser Asn Gln Ala Ser Leu Ser Cys Asp Arg
            20                  25                  30

Asn Gly Ile Cys Lys Gly Ser Ser Gly Ser Leu Asn Ser Ile Pro Ser
        35                  40                  45

Gly Leu Thr Glu Ala Val Lys Ser Leu Asp Leu Ser Asn Asn Arg Ile
    50                  55                  60

Thr Tyr Ile Ser Asn Ser Asp Leu Gln Arg Cys Val Asn Leu Gln Ala
65                  70                  75                  80

Leu Val Leu Thr Ser Asn Gly Ile Asn Thr Ile Glu Glu Asp Ser Phe
                85                  90                  95

Ser Ser Leu Gly Ser Leu Glu His Leu Asp Leu Ser Tyr Asn Tyr Leu
            100                 105                 110

Ser Asn Leu Ser Ser Ser Trp Phe Lys Pro Leu Ser Ser Leu Thr Phe
        115                 120                 125
```

```
Leu Asn Leu Leu Gly Asn Pro Tyr Lys Thr Leu Gly Glu Thr Ser Leu
130                 135                 140

Phe Ser His Leu Thr Lys Leu Gln Ile Leu Arg Val Gly Asn Met Asp
145                 150                 155                 160

Thr Phe Thr Lys Ile Gln Arg Lys Asp Phe Ala Gly Leu Thr Phe Leu
                165                 170                 175

Glu Glu Leu Glu Ile Asp Ala Ser Asp Leu Gln Ser Tyr Glu Pro Lys
                180                 185                 190

Ser Leu Lys Ser Ile Gln Asn Val Ser His Leu Ile Leu His Met Lys
                195                 200                 205

Gln His Ile Leu Leu Leu Glu Ile Phe Val Asp Val Thr Ser Ser Val
210                 215                 220

Glu Cys Leu Glu Leu Arg Asp Thr Asp Leu Asp Thr Phe His Phe Ser
225                 230                 235                 240

Glu Leu Ser Thr Gly Glu Thr Asn Ser Leu Ile Lys Lys Phe Thr Phe
                245                 250                 255

Arg Asn Val Lys Ile Thr Asp Glu Ser Leu Phe Gln Val Met Lys Leu
                260                 265                 270

Leu Asn Gln Ile Ser Gly Leu Leu Glu Leu Glu Phe Asp Asp Cys Thr
        275                 280                 285

Leu Asn Gly Val Gly Asn Phe Arg Ala Ser Asp Asn Asp Arg Val Ile
290                 295                 300

Asp Pro Gly Lys Val Glu Thr Leu Thr Ile Arg Arg Leu His Ile Pro
305                 310                 315                 320

Arg Phe Tyr Leu Phe Tyr Asp Leu Ser Thr Leu Tyr Ser Leu Thr Glu
                325                 330                 335

Arg Val Lys Arg Ile Thr Val Glu Asn Ser Lys Val Phe Leu Val Pro
                340                 345                 350

Cys Leu Leu Ser Gln His Leu Lys Ser Leu Glu Tyr Leu Asp Leu Ser
                355                 360                 365

Glu Asn Leu Met Val Glu Glu Tyr Leu Lys Asn Ser Ala Cys Glu Asp
370                 375                 380

Ala Trp Pro Ser Leu Gln Thr Leu Ile Leu Arg Gln Asn His Leu Ala
385                 390                 395                 400

Ser Leu Glu Lys Thr Gly Glu Thr Leu Leu Thr Leu Lys Asn Leu Thr
                405                 410                 415

Asn Ile Asp Ile Ser Lys Asn Ser Phe His Ser Met Pro Glu Thr Cys
                420                 425                 430

Gln Trp Pro Glu Lys Met Lys Tyr Leu Asn Leu Ser Ser Thr Arg Ile
                435                 440                 445

His Ser Val Thr Gly Cys Ile Pro Lys Thr Leu Glu Ile Leu Asp Val
                450                 455                 460

Ser Asn Asn Asn Leu Asn Leu Phe Ser Leu Asn Leu Pro Gln Leu Lys
465                 470                 475                 480

Glu Leu Tyr Ile Ser Arg Asn Lys Leu Met Thr Leu Pro Asp Ala Ser
                485                 490                 495

Leu Leu Pro Met Leu Leu Val Leu Lys Ile Ser Arg Asn Ala Ile Thr
                500                 505                 510

Thr Phe Ser Lys Glu Gln Leu Asp Ser Phe His Thr Leu Lys Thr Leu
                515                 520                 525

Glu Ala Gly Gly Asn Asn Phe Ile Cys Ser Cys Glu Phe Leu Ser Phe
530                 535                 540
```

```
Thr Gln Glu Gln Gln Ala Leu Ala Lys Val Leu Ile Asp Trp Pro Ala
545                 550                 555                 560

Asn Tyr Leu Cys Asp Ser Pro Ser His Val Arg Gly Gln Gln Val Gln
                565                 570                 575

Asp Val Arg Leu Ser Val Ser Glu Cys His Arg Thr Ala Leu Val Ser
            580                 585                 590

Gly Met Cys Cys Ala Leu Phe Leu Leu Ile Leu Leu Thr Gly Val Leu
        595                 600                 605

Cys His Arg Phe His Gly Leu Trp Tyr Met Lys Met Met Trp Ala Trp
    610                 615                 620

Leu Gln Ala Lys Arg Lys Pro Arg Lys Ala Pro Ser Arg Asn Ile Cys
625                 630                 635                 640

Tyr Asp Ala Phe Val Ser Tyr Ser Glu Arg Asp Ala Tyr Trp Val Glu
                645                 650                 655

Asn Leu Met Val Gln Glu Leu Glu Asn Phe Asn Pro Pro Phe Lys Leu
            660                 665                 670

Cys Leu His Lys Arg Asp Phe Ile Pro Gly Lys Trp Ile Ile Asp Asn
        675                 680                 685

Ile Ile Asp Ser Ile Glu Lys Ser His Lys Thr Val Phe Val Leu Ser
    690                 695                 700

Glu Asn Phe Val Lys Ser Glu Trp Cys Lys Tyr Glu Leu Asp Phe Ser
705                 710                 715                 720

His Phe Arg Leu Phe Glu Glu Asn Asn Asp Ala Ala Ile Leu Ile Leu
                725                 730                 735

Leu Glu Pro Ile Glu Lys Lys Ala Ile Pro Gln Arg Phe Cys Lys Leu
            740                 745                 750

Arg Lys Ile Met Asn Thr Lys Thr Tyr Leu Glu Trp Pro Met Asp Glu
        755                 760                 765

Ala Gln Arg Glu Gly Phe Trp Val Asn Leu Arg Ala Ala Ile Lys Ser
    770                 775                 780

<210> SEQ ID NO 2
<211> LENGTH: 784
<212> TYPE: PRT
<213> ORGANISM: Mus musculus

<400> SEQUENCE: 2

Met Leu Arg Ala Leu Trp Leu Phe Trp Ile Leu Val Ala Ile Thr Val
1               5                   10                  15

Leu Phe Ser Lys Arg Cys Ser Ala Gln Glu Ser Leu Ser Cys Asp Ala
                20                  25                  30

Ser Gly Val Cys Asp Gly Arg Ser Arg Ser Phe Thr Ser Ile Pro Ser
            35                  40                  45

Gly Leu Thr Ala Ala Met Lys Ser Leu Asp Leu Ser Phe Asn Lys Ile
        50                  55                  60

Thr Tyr Ile Gly His Gly Asp Leu Arg Ala Cys Ala Asn Leu Gln Val
65                  70                  75                  80

Leu Met Leu Lys Ser Ser Arg Ile Asn Thr Ile Glu Gly Asp Ala Phe
                85                  90                  95

Tyr Ser Leu Gly Ser Leu Glu His Leu Asp Leu Ser Asn His Leu
            100                 105                 110

Ser Ser Leu Ser Ser Ser Trp Phe Gly Pro Leu Ser Ser Leu Lys Tyr
        115                 120                 125

Leu Asn Leu Met Gly Asn Pro Tyr Gln Thr Leu Gly Val Thr Ser Leu
    130                 135                 140
```

-continued

```
Phe Pro Asn Leu Thr Asn Leu Gln Thr Leu Arg Ile Gly Asn Val Glu
145                 150                 155                 160

Thr Phe Ser Glu Ile Arg Arg Ile Asp Phe Ala Gly Leu Thr Ser Leu
            165                 170                 175

Asn Glu Leu Glu Ile Lys Ala Leu Ser Leu Arg Asn Tyr Gln Ser Gln
                180                 185                 190

Ser Leu Lys Ser Ile Arg Asp Ile His His Leu Thr Leu His Leu Ser
            195                 200                 205

Glu Ser Ala Phe Leu Leu Glu Ile Phe Ala Asp Ile Leu Ser Ser Val
        210                 215                 220

Arg Tyr Leu Glu Leu Arg Asp Thr Asn Leu Ala Arg Phe Gln Phe Ser
225                 230                 235                 240

Pro Leu Pro Val Asp Glu Val Ser Ser Pro Met Lys Lys Leu Ala Phe
                245                 250                 255

Arg Gly Ser Val Leu Thr Asp Glu Ser Phe Asn Glu Leu Leu Lys Leu
            260                 265                 270

Leu Arg Tyr Ile Leu Glu Leu Ser Glu Val Glu Phe Asp Asp Cys Thr
        275                 280                 285

Leu Asn Gly Leu Gly Asp Phe Asn Pro Ser Glu Ser Asp Val Val Ser
290                 295                 300

Glu Leu Gly Lys Val Glu Thr Val Thr Ile Arg Arg Leu His Ile Pro
305                 310                 315                 320

Gln Phe Tyr Leu Phe Tyr Asp Leu Ser Thr Val Tyr Ser Leu Leu Glu
                325                 330                 335

Lys Val Lys Arg Ile Thr Val Glu Asn Ser Lys Val Phe Leu Val Pro
            340                 345                 350

Cys Ser Phe Ser Gln His Leu Lys Ser Leu Glu Phe Leu Asp Leu Ser
        355                 360                 365

Glu Asn Leu Met Val Glu Glu Tyr Leu Lys Asn Ser Ala Cys Lys Gly
370                 375                 380

Ala Trp Pro Ser Leu Gln Thr Leu Val Leu Ser Gln Asn His Leu Arg
385                 390                 395                 400

Ser Met Gln Lys Thr Gly Glu Ile Leu Leu Thr Leu Lys Asn Leu Thr
                405                 410                 415

Ser Leu Asp Ile Ser Arg Asn Thr Phe His Pro Met Pro Asp Ser Cys
            420                 425                 430

Gln Trp Pro Glu Lys Met Arg Phe Leu Asn Leu Ser Ser Thr Gly Ile
        435                 440                 445

Arg Val Val Lys Thr Cys Ile Pro Gln Thr Leu Glu Val Leu Asp Val
450                 455                 460

Ser Asn Asn Asn Leu Asp Ser Phe Ser Leu Phe Leu Pro Arg Leu Gln
465                 470                 475                 480

Glu Leu Tyr Ile Ser Arg Asn Lys Leu Lys Thr Leu Pro Asp Ala Ser
                485                 490                 495

Leu Phe Pro Val Leu Leu Val Met Lys Ile Arg Glu Asn Ala Val Ser
            500                 505                 510

Thr Phe Ser Lys Asp Gln Leu Gly Ser Phe Pro Lys Leu Glu Thr Leu
        515                 520                 525

Glu Ala Gly Asp Asn His Phe Val Cys Ser Cys Glu Leu Leu Ser Phe
530                 535                 540

Thr Met Glu Thr Pro Ala Leu Ala Gln Ile Leu Val Asp Trp Pro Asp
545                 550                 555                 560
```

```
Ser Tyr Leu Cys Asp Ser Pro Pro Arg Leu His Gly His Arg Leu Gln
                565                 570                 575

Asp Ala Arg Pro Ser Val Leu Glu Cys His Gln Ala Ala Leu Val Ser
            580                 585                 590

Gly Val Cys Cys Ala Leu Leu Leu Ile Leu Leu Val Gly Ala Leu
        595                 600                 605

Cys His His Phe His Gly Leu Trp Tyr Leu Arg Met Met Trp Ala Trp
    610                 615                 620

Leu Gln Ala Lys Arg Lys Pro Lys Ala Pro Cys Arg Asp Val Cys
625                 630                 635                 640

Tyr Asp Ala Phe Val Ser Tyr Ser Glu Gln Asp Ser His Trp Val Glu
                645                 650                 655

Asn Leu Met Val Gln Gln Leu Glu Asn Ser Asp Pro Pro Phe Lys Leu
            660                 665                 670

Cys Leu His Lys Arg Asp Phe Val Pro Gly Lys Trp Ile Ile Asp Asn
        675                 680                 685

Ile Ile Asp Ser Ile Glu Lys Ser His Lys Thr Val Phe Val Leu Ser
    690                 695                 700

Glu Asn Phe Val Arg Ser Glu Trp Cys Lys Tyr Glu Leu Asp Phe Ser
705                 710                 715                 720

His Phe Arg Leu Phe Asp Glu Asn Asn Asp Ala Ala Ile Leu Val Leu
                725                 730                 735

Leu Glu Pro Ile Glu Arg Lys Ala Ile Pro Gln Arg Phe Cys Lys Leu
            740                 745                 750

Arg Lys Ile Met Asn Thr Lys Thr Tyr Leu Glu Trp Pro Leu Asp Glu
        755                 760                 765

Gly Gln Gln Glu Val Phe Trp Val Asn Leu Arg Thr Ala Ile Lys Ser
    770                 775                 780

<210> SEQ ID NO 3
<211> LENGTH: 21
<212> TYPE: PRT
<213> ORGANISM: Homo sapiens

<400> SEQUENCE: 3

Lys Glu Glu Ser Ser Asn Gln Ala Ser Leu Ser Cys Asp Arg Asn Gly
1               5                   10                  15

Ile Cys Lys Gly Ser
            20

<210> SEQ ID NO 4
<211> LENGTH: 13
<212> TYPE: PRT
<213> ORGANISM: Homo sapiens

<400> SEQUENCE: 4

Cys Ser Cys Glu Phe Leu Ser Phe Thr Gln Glu Gln Gln
1               5                   10

<210> SEQ ID NO 5
<211> LENGTH: 586
<212> TYPE: PRT
<213> ORGANISM: Homo sapiens
```

<400> SEQUENCE: 5

```
Met Pro His Thr Leu Trp Met Val Trp Val Leu Gly Val Ile Ile Ser
1               5                   10                  15

Leu Ser Lys Glu Glu Ser Ser Asn Gln Ala Ser Leu Ser Cys Asp Arg
            20                  25                  30

Asn Gly Ile Cys Lys Gly Ser Gly Ser Leu Asn Ser Ile Pro Ser
        35                  40                  45

Gly Leu Thr Glu Ala Val Lys Ser Leu Asp Leu Ser Asn Asn Arg Ile
    50                  55                  60

Thr Tyr Ile Ser Asn Ser Asp Leu Gln Arg Cys Val Asn Leu Gln Ala
65                  70                  75                  80

Leu Val Leu Thr Ser Asn Gly Ile Asn Thr Ile Glu Glu Asp Ser Phe
                85                  90                  95

Ser Ser Leu Gly Ser Leu Glu His Leu Asp Leu Ser Tyr Asn Tyr Leu
            100                 105                 110

Ser Asn Leu Ser Ser Ser Trp Phe Lys Pro Leu Ser Ser Leu Thr Phe
        115                 120                 125

Leu Asn Leu Leu Gly Asn Pro Tyr Lys Thr Leu Gly Glu Thr Ser Leu
    130                 135                 140

Phe Ser His Leu Thr Lys Leu Gln Ile Leu Arg Val Gly Asn Met Asp
145                 150                 155                 160

Thr Phe Thr Lys Ile Gln Arg Lys Asp Phe Ala Gly Leu Thr Phe Leu
                165                 170                 175

Glu Glu Leu Glu Ile Asp Ala Ser Asp Leu Gln Ser Tyr Glu Pro Lys
            180                 185                 190

Ser Leu Lys Ser Ile Gln Asn Val Ser His Leu Ile Leu His Met Lys
        195                 200                 205

Gln His Ile Leu Leu Glu Ile Phe Val Asp Val Thr Ser Ser Val
    210                 215                 220

Glu Cys Leu Glu Leu Arg Asp Thr Asp Leu Asp Thr Phe His Phe Ser
225                 230                 235                 240

Glu Leu Ser Thr Gly Glu Thr Asn Ser Leu Ile Lys Lys Phe Thr Phe
                245                 250                 255

Arg Asn Val Lys Ile Thr Asp Glu Ser Leu Phe Gln Val Met Lys Leu
            260                 265                 270

Leu Asn Gln Ile Ser Gly Leu Leu Glu Leu Glu Phe Asp Asp Cys Thr
        275                 280                 285

Leu Asn Gly Val Gly Asn Phe Arg Ala Ser Asp Asn Asp Arg Val Ile
    290                 295                 300

Asp Pro Gly Lys Val Glu Thr Leu Thr Ile Arg Arg Leu His Ile Pro
305                 310                 315                 320

Arg Phe Tyr Leu Phe Tyr Asp Leu Ser Thr Leu Tyr Ser Leu Thr Glu
                325                 330                 335

Arg Val Lys Arg Ile Thr Val Glu Asn Ser Lys Val Phe Leu Val Pro
            340                 345                 350

Cys Leu Leu Ser Gln His Leu Lys Ser Leu Glu Tyr Leu Asp Leu Ser
        355                 360                 365

Glu Asn Leu Met Val Glu Glu Tyr Leu Lys Asn Ser Ala Cys Glu Asp
    370                 375                 380

Ala Trp Pro Ser Leu Gln Thr Leu Ile Leu Arg Gln Asn His Leu Ala
385                 390                 395                 400

Ser Leu Glu Lys Thr Gly Glu Thr Leu Leu Thr Leu Lys Asn Leu Thr
                405                 410                 415
```

-continued

```
Asn Ile Asp Ile Ser Lys Asn Ser Phe His Ser Met Pro Glu Thr Cys
            420                 425                 430

Gln Trp Pro Glu Lys Met Lys Tyr Leu Asn Leu Ser Ser Thr Arg Ile
        435                 440                 445

His Ser Val Thr Gly Cys Ile Pro Lys Thr Leu Glu Ile Leu Asp Val
    450                 455                 460

Ser Asn Asn Asn Leu Asn Leu Phe Ser Leu Asn Leu Pro Gln Leu Lys
465                 470                 475                 480

Glu Leu Tyr Ile Ser Arg Asn Lys Leu Met Thr Leu Pro Asp Ala Ser
                485                 490                 495

Leu Leu Pro Met Leu Leu Val Leu Lys Ile Ser Arg Asn Ala Ile Thr
            500                 505                 510

Thr Phe Ser Lys Glu Gln Leu Asp Ser Phe His Thr Leu Lys Thr Leu
        515                 520                 525

Glu Ala Gly Gly Asn Asn Phe Ile Cys Ser Cys Glu Phe Leu Ser Phe
        530                 535                 540

Thr Gln Glu Gln Gln Ala Leu Ala Lys Val Leu Ile Asp Trp Pro Ala
545                 550                 555                 560

Asn Tyr Leu Cys Asp Ser Pro Ser His Val Arg Gly Gln Gln Val Gln
                565                 570                 575

Asp Val Arg Leu Ser Val Ser Glu Cys His
            580                 585
```

TREATMENT OF RENAL DISEASE

CROSS REFERENCE TO RELATED APPLICATIONS

This application is a continuation of U.S. application Ser. No.: 12/667,450, filed Jun. 28, 2010, now abandoned, which application is a national stage filing under 35 U.S.C. §371 of international application PCT/EP2008/058732, filed Jul. 4, 2008, which was published under PCT Article 21(2) in English, and which claims the benefit under 35 USC §119(e) of U.S. Provisional Application No. 61/038,304, filed Mar. 20, 2008, and also Ireland Application No. 2007/0486, filed Jul. 5, 2007, the disclosures of all of which are incorporated by reference herein in their entirety.

FIELD OF THE INVENTION

The present invention relates to compositions and methods for the treatment and prophylaxis of renal disease. In particular, there is provided methods for the treatment of conditions such as glomerulonephritis which are characterised by inflammation of the glomeruli of the kidney, said methods comprising the use of compounds which antagonise the function of the receptor Toll-like Receptor 2.

BACKGROUND TO THE INVENTION

Each kidney is composed of around one million nephrons. The glomerulus, a component of the nephron, is comprised of a bundle of parallel capillaries, this structure being referred to as the Bowman's capsule the function of the glomerulus is to filter water and solutes from the blood.

Glomerulonephritis is a disease of the kidney which is characterised by the inflammation of the glomeruli. Inflammation of the glomerulus compromises glomerular function, this resulting in a narrowing or blocking of the capillaries which results in a disruption to normal glomerular filtration.

Glomrulonephritis can result in large amounts of protein being passed into the urine, in a condition known as proteinuria. Further symptoms of glomerulonephritis may include excessive blood urea nitrogen (uremia), haematuria, hyperlipidemia, a reduction in glomerular filtration rate, hypoalbuminaemia and lipiduria.

Current treatments for glomerulonephritis include the administration of corticosteroids and/or non-steroidal anti-inflammatory drugs. In more severe cases, blood dialysis or organ transplantation may be required. Such therapies are however unsatisfactory for a number of reasons. In the case of corticosteroid use, this being the most commonly employed therapy for the treatment of glomerulonephritis, the treatment has to be managed carefully in order to limit the immune suppression of the patient which can result from prolonged steroid administration. Further, the burden or long term dialysis, or the risks associated with transplant surgery and organ rejection also make these therapies less desirable.

Accordingly, there is a pressing need for a therapeutic treatment which can be targeted to the inflamed glomerulus in order to prevent or treat the inflamed glomerulus during glomerulonephritis and which does not suffer from the disadvantages and side effects of the hitherto known treatments.

Toll-like Receptors (TLRs) form a family of pattern recognition receptors which have a key role in activating the innate immune response. 11 Toll-like Receptors have been identified in humans to date. The members of the Toll-like Receptor family are highly conserved, with most mammalian species having between 10 to 15 Toll-like Receptors. Each Toll-like Receptor recognises specific pathogen-associated molecular signatures. For example, Toll-like Receptor 2 (TLR2, CD282, TLR-2) can be activated by peptidoglycan, lipoproteins and lipoteichoic acid. Toll-like Receptors are known to form either homodimers or heterodimers wherein each dimer has a different ligand specificity. TLR2 forms a heterodimer with either TLR1 or TLR6 and possibly also TLR10, in some instances, to form a membrane bound receptor complex. In addition, the ectodomain of Toll-like Receptor 2 is known to form a soluble heterodimer with the CD14 protein in the circulatory system and also in mammalian milk.

Ligand binding to Toll-like Receptor 2 results in downstream signalling involving cytoplasmic adaptor proteins such as MyD88 and Mal (MyD88-adaptor like), which is also known as TIRAP (Toll-Interleukin-1 receptor domain containing adaptor protein).

The involvement of Toll-like Receptor 2 and Toll-like Receptor 2-induced signalling and immune system activation has implicated Toll-like Receptor 2 as an important mediator in the development of inflammation and immune-mediated disease. Accordingly there has been significant therapeutic interest in relation to the modulation of the Toll-like Receptor 2 signalling pathway. Toll-like Receptor 2 mediated intracellular signaling results in activation of the innate immune system. However, in some instances, the activation of the innate immune system which results following Toll-like Receptor 2 activation has been shown to be a factor in causing inflammation and immune-mediated disease. As such, a number of therapeutic approaches have sought to block TLR-2 ligand binding, or which suppress the functional activity of Toll-like Receptor 2 following ligand binding, for example by suppressing Toll-like Receptor 2 mediated intracellular signalling which results following Toll-like Receptor 2 activation.

In relation to the pathology of kidney disease, Toll-like Receptor 2 has been shown to be involved in the induction of the antigen-specific adaptive immune response associated with the development and recurrence of immune-mediated kidney disease such as glomerulonephritis. Specifically, it has been shown that a Toll-like Receptor 2 ligand, lipopeptide, can exacerbate nephrotoxic nephritis in a Toll-like Receptor 2-dependent manner. Toll-like Receptor 2 activation showed an increased amount of antigen specific IgG isotypes such as $IgG_1$, $IgG_{2b}$, $IgG_3$ in the serum and $IgG_{2b}$ and $IgG_3$ are seen to be deposited within the glomerulus. Elevated CD4+ positive T cell infiltration was also observed in the glomerulus. Nevertheless, there has been no evidence to date to suggest that blocking the Toll-like Receptor 2 pathway would provide a basis for a treatment for immune-mediated kidney disorders.

Following extensive experimentation, the inventors have surprisingly identified that compounds which antagonise Toll-like Receptor 2 function, for example by blocking Toll-like Receptor 2 ligand binding, or by blocking intracellular signalling mediated by activated Toll-like Receptor 2, cause a reduction in the level of inflammation in the kidney. The inventors have identified that such compounds have utility in methods for the treatment of inflammatory conditions of the kidney, and in particular for the treatment of conditions such as glomerulonephritis. In particular, the inventors have surprisingly shown that blocking Toll-like Receptor 2 ligand binding, through the use of an antibody, or a functional binding fragment thereof, which has binding specificity to at least one binding epitopes present on Toll-like Receptor 2, and which inhibits ligand binding to Toll-like Receptor 2, can suppress the production of neutrophils, and suppress albuminuria and thrombosis which are typically elevated during onset of glomerulonephritis. As such, compounds which mediate such an effect downregulate Toll-like Receptor 2 mediated activation and downstream TLR-2 induced intracellular signalling.

SUMMARY OF THE INVENTION

According to a first aspect of the present invention there is provided a method of reducing one or more biological activities of Toll-like receptor 2 (TLR2) in a TLR2 expressing cell or tissue implicated in renal inflammation and disease, comprising:

contacting the cell or tissue with an antagonist of TLR2 activity or TLR2 expression, in an amount sufficient to reduce one or more biological activities of TLR2 in the cell or tissue.

In certain embodiments the TLR2 expressing cell or tissue is a cell or tissue of the kidney. In certain embodiments of the invention, the TLR2 expressing cell may be at least one cell type selected from the group comprising, but not limited to: renal tubular epithelial cells (TECs), an epithelial cell of the Bowman's capsule, a kidney glomerulus parietal cell, a kidney glomerulus podocyte, a kidney proximal tubule brush border cell, a loop of henle thin segment cell, a kidney distal tubule cell, or a kidney collecting duct cell.

In certain embodiments, the contacting step occurs in a cell lysate, a reconstituted system or to cells in culture. In certain embodiments, the contacting step occurs on cells or a tissue present in a subject. In certain embodiments the TLR2 may be a human TLR2, a murine TLR2, or a TLR2 derived from any other mammalian species.

In certain embodiments the method is performed on a human subject having, or at risk of having renal inflammation or renal disease.

As herein defined, the term "renal inflammation and disease" extends to all conditions which are substantially characterised by the occurrence of inflammation within the kidney, or where the occurrence of inflammation in the kidney is caused by a disease or an inflammatory condition which primarily affects a site in the body other than the kidney. In particular, inflammation may occur at a site including, but not limited to; the glomerulus, Bowman's capsule or Bowman's space. Typically, the inflammation results in at least partial impairment of kidney function and/or kidney failure.

Furthermore, the term "renal inflammation and disease" may further include "kidney disease", wherein the term kidney disease generally refers to a disorder of at least one kidney in a human, wherein the disorder compromises or impairs the function of the kidney(s), this being characterised physiologically by, for example, the leakage of protein into the urine, or by the excretion of nitrogenous waste. The Kidney disease may also result from a primary pathology of the kidney, such as injury to the glomerulus or tubule, or from damage to another organ, such as the pancreas, which adversely affects the ability of the kidney to perform biological functions, such as the retention of protein. Thus, Kidney disease in the human can be the direct or indirect effect of a disease condition which may affect other organs. Examples of diseases which affect the kidneys, but which do not specifically target the kidneys are diabetes and systemic lupus. The terms renal disease and kidney disease are used interchangeably herein with the phrase "diseases of the kidney". The kidney disease can, for example, result from, or be a consequence of any change, damage, or trauma to the glomerulus, tubules or interstitial tissue in either the kidney cortex or kidney medulla.

The kidney disease may also be a progressive kidney disease. The term "progressive kidney disease" as used herein refers to any disease of the kidney that over time (e.g., days, weeks, months, years) leads to a loss of kidney function. As herein defined, the term "kidney function" generally refers to a physiological property of the kidney, such as the ability to retain protein thereby preventing proteinuria (e.g., albuminuria). Kidney function can be assessed, for example, by glomerular filtration rate (e.g., creatinine clearance), excretion of protein in urine e.g. albuminuria, blood urea nitrogen, serum or plasma creatinine, or any combination thereof.

Examples of specific conditions which fall within the meaning of the term "renal inflammation and disease" include, but are not limited to: renal disorders which include, but are not limited to: chronic renal failure, acute renal failure, heterologous nephrotoxic nephritis, glomerulonephritis, sclerosis of the glomerulus, systemic lupus erythematosus (SLE), diabetic nephropathy, diabetic nephropathy wherein the diabetic nephropathy accompanies sclerosis of the liver, and glomerulonephritis wherein the glomerulonephritis is accompanied by sclerosis of the liver.

In certain further embodiments, renal inflammation and disease may relate to an immune-mediated disease which affects the cells of the kidney and/or kidney function. Such conditions may include, but are not limited to: Immunoglobulin A nephropathy, membranoproliferative glomerulonephritis, mesangial proliferative glomerulonephritis, nonproliferative glomerulonephritis, membranous glomerulonephritis, minimal-change disease, primary focal segmental glomerulosclerosis (FSGS), fibrillary glomerulonephritis, immunotactoid glomerulonephritis, proliferative glomerulonephritis, progressive glomerulonephritis, anti-GBM disease, kidney ischemia, kidney vasculitis, including disease associated with anti-neutrophil cytoplasmic antibodies (ANCA) (e.g., Wegener granulomatosis), lupus nephritis cryoglobulinemia-associated glomerulonephritis, bacterial endocarditis, Henoch-Schönlein purpura, postinfectious glomerulonephritis, Hepatitis C, diabetic nephropathy, myloidosis, hypertensive nephrosclerosis, light-chain disease from multiple myeloma, secondary focal glomerulosclerosis, and hypertensive nephrosclerosis.

The term "renal inflammation and disease" also encompasses acute renal failure. Acute renal failure ("ARF") refers to the clinical conditions associated with rapid, steadily increasing azotemia, with or without oliguria (<500 mL/day). The cause of ARF can be grouped into three diagnostic categories: prerenal (inadequate renal perfusion); postrenal (obstruction); and renal. The pathophysiology of ARF is complex and multifactorial. Current concepts suggest that ARF may result from direct renal tubular injury, renal ischemia or intra-tubular obstruction. Clinically, ARF results in diminished glomerular filtration and reduced secretion of metabolic waste products, water, and electrolytes. Fluid overload, electrolyte imbalances and the uremic syndrome result in organ dysfunction. Organ dysfunction may ultimately result in death.

The antagonist of TLR2 activity or TLR2 expression may also be referred to as TLR2 modulator agent. The TLR2 modulator agents of the invention inhibit TLR2 function and therefore act to prevent TLR2 mediated or dependent pathophysiological mechanisms contributing to renal failure. Examples of such pathophysiological mechanisms include direct renal tubular injury, renal ischemia, and intra-tubular obstruction.

In certain embodiments, the TLR2 modulator agent is administered to the subject such that it can specifically target cellular populations of the kidney such as the renal tubular epithelial cells (TECs) and/or the epithelial cells of the Bowman's capsule. Direct targeting of the Toll-like Receptor 2 modulator agent to the kidney or cells thereof avoids global suppression of Toll-like Receptor 2 function in a subject. This targeted approach to therapy can be particularly effective where it is desirable to suppress Toll-like Receptor 2-mediated inflammation in the kidney, but where it is not desirable to down-regulate Toll-like Receptor 2 activity at sites other than the kidney, this resulting in potential immunosuppression in sites other than the kidney. Compounds, such as labelling compounds or targeting molecules which can be used to direct the TLR2 modulator compound of the invention to the cells of the kidney will be known to the person skilled in the art. Such targeting means typically comprise a binding agent which has binding specificity for a ligand or cell surface marker which is specific to the cell which is to be targeted.

In certain embodiments the TLR2 antagonist is selected from the group comprising, but not limited to: a protein, a peptide, a peptidomimetic, a nucleic acid, a carbohydrate, a lipid, an aptamer and a small molecule compound.

In certain embodiments the TLR2 antagonist is an antibody molecule. Typically the antibody has binding specificity to an epitope present on human TLR2. In certain embodiments, the antibody molecule, or a binding fragment derived therefrom has binding specificity to an epitope comprising amino acid residues of the extracellular domain of TLR2. In certain embodiments, the TLR2 antagonist binds to a non-continuous epitope comprising amino acid residues derived from the amino and carboxyl terminals of the amino acid sequence of human TLR2. In certain embodiments the TLR2 antagonist binds to an epitope on TLR2 comprising amino acid residues 19 to 39, or 538 to 549 of the extracellular domain of TLR2 are defined in SEQ ID NO:2.

In certain embodiments the antibody is selected from the group consisting of a human, humanised, chimeric, synthetic, camelid, shark or in-vitro antibody which has binding specificity to TLR2. In further embodiments, the invention extends to an antibody binding fragment which is derived from any of the aforesaid antibodies. In certain embodiments, the antibody is an antibody binding fragment selected from the group consisting of a Fab, scFv, Fv, or dAb fragment. In certain embodiments the antibody molecule comprises two complete heavy chains, and two complete light chains, or an antigen-binding fragment thereof. In certain embodiments, the antibody is of the isotype IgG, IgA, IgM. In embodiments where the antibody is of the isotype IgG, the antibody may be of the subtype IgG1, IgG2 or IgG3.

In certain embodiments, the antibody is a murine IgG1 anti-TLR2 antibody (mouse Toll-like Receptor 2 (TLR2) antibody, derived from hybridoma clone T2.5, HyCult Biotechnology b.v., Cell Sciences, Canton, USA: catalogue number 1054), or a humanised version thereof.

In certain embodiments the TLR2 antagonist inhibits the expression of nucleic acid encoding the TLR2 protein. In such embodiments the TLR2 antagonist may be selected from the group comprising, but not limited to: an anti-sense oligonucleotides, triple helix molecules, anti-sense DNA, anti-sense RNA, ribozyme, iRNA, miRNA, siRNA, and an shRNA molecule.

According to a further aspect of the invention there is provided a method for the treatment and/or prophylaxis of a renal disorder, the method comprising the steps of:
  providing a therapeutically effective amount of an agent which modulates the function or expression of Toll-like Receptor 2 (TLR2), and
  administering said compound to a subject in need of such treatment.

In certain embodiments, the renal disorder is at least one of the group consisting of: renal disease, a renal inflammatory condition, chronic renal failure, acute renal failure, heterologous nephrotoxic nephritis, glomerulonephritis, sclerosis of the glomerulus, systemic lupus erythematosus (SLE), diabetic nephropathy, diabetic nephropathy wherein the diabetic nephropathy accompanies sclerosis of the liver, and glomerulonephritis wherein the glomerulonephritis is accompanied by sclerosis of the liver.

In certain further embodiments, the renal disorder relates to an immune-mediated disease which affects the cells of the kidney and/or kidney function. Such disorders may include, but are not limited to: Immunoglobulin A nephropathy, membranoproliferative glomerulonephritis, mesangial proliferative glomerulonephritis, nonproliferative glomerulonephritis, membranous glomerulonephritis, minimal-change disease, primary focal segmental glomerulosclerosis (FSGS), fibrillary glomerulonephritis, immunotactoid glomerulonephritis, proliferative glomerulonephritis, progressive glomerulonephritis, anti-GBM disease, kidney ischemia, kidney vasculitis, including disease associated with anti-neutrophil cytoplasmic antibodies (ANCA) (e.g., Wegener granulomatosis), lupus nephritis cryoglobulinemia-associated glomerulonephritis, bacterial endocarditis, Henoch-Schönlein purpura, postinfectious glomerulonephritis, Hepatitis C disease, diabetic nephropathy, myloidosis, hypertensive nephrosclerosis, light-chain disease from multiple myeloma, secondary focal glomerulosclerosis, and hypertensive nephrosclerosis.

In certain further embodiments, the renal disorder may relate to any renal inflammatory condition or disease as hereinbefore described, or further to any kidney disease as hereinbefore described.

As herein defined, the term 'modulates the function' means that the agent modulates one or more of the biological functional activities of Toll-like Receptor 2. In certain embodiments, the modulation of Toll-like Receptor 2 function relates to an inhibition of the functional activation of Toll-like Receptor 2 and/or of the inhibition or suppression of downstream intracellular signalling mediated by Toll-like Receptor 2. Modulation may further extend to a suppression of the expression of Toll-like Receptor 2 protein, or the expression of a gene which encodes Toll-like Receptor 2.

As defined herein, an 'agent' which modulates the expression or function of TLR2 is a compound which suppresses or blocks the activation, expression or function of Toll-like Receptor 2. In certain embodiments, the 'agent' may be a TLR2 antagonist compound which inhibits or blocks the binding of a ligand or binding compound to Toll-like Receptor 2. For example, the 'agent' may be a Toll-like Receptor 2 binding agent, such as an antibody, which binds to the extracellular domain of Toll-like Receptor 2, said agent inhibiting the binding of TLR2 activating ligands which have binding specificity for TLR2. Further, the 'agent' may be a compound which inhibits or suppresses intracellular signalling mediated by Toll-like Receptor 2 following ligand binding and/or Toll-like Receptor 2 activation.

The 'agent' may further modulate Toll-like Receptor 2 expression, for example by inhibiting the expression of a gene encoding a Toll-like Receptor 2 protein.

In certain embodiments, the 'an agent which modulates the function or expression of Toll-like Receptor 2' may be a binding compound which has binding specificity or which specifically binds Toll-like Receptor 2. In certain embodiments, the binding compound is selected from the group comprising, but not limited to: a protein, a peptide, a peptidomimetic, a nucleic acid, a polynucleotide, a polysaccharide, an oligopeptide, a carbohydrate, a lipid, an aptamer, a small molecule compound, and a naturally occurring compound, such as a plant derived compound.

In certain embodiments, the agent which modulates the function or expression of Toll-like Receptor 2 is a binding compound which specifically binds to Toll-like Receptor 2 at a site other than the ligand binding site, and which, upon binding, causes a change in the confirmation of Toll-like Receptor 2, which leads to an inhibition of Toll-like Receptor 2 agonist binding. Typically, said binding site will be located at the extracellular domain of TLR2.

The term "specifically binds" or "binding specificity" refers to the ability of a TLR2 modulator agent or TLR2 binding compound to bind to a target epitope present on TLR2 with a greater affinity than it binds to a non-target epitope. In certain embodiments, the term "specifically binds" refers to the binding of the agent to a target epitope present on TLR2 with a binding affinity which is at least 10, 50, 100, 250, 500, or 1000 times greater than the binding affinity for a non-target epitope. In certain embodiments, binding affinity is determined by an affinity ELISA assay. In alternative embodiments, affinity is determined by a BIAcore assay. Alternatively, binding affinity may be determined by a kinetic method. In certain embodiments, affinity is determined by an equilibrium/solution method.

According to one embodiment, TLR2 modulators, including TLR2 binding agents, such as TLR2 antagonists, bind to TLR2 with high affinity, for example, with an affinity constant of at least about $10^7$ $M^{-1}$, typically about $10^8$ $M^{-1}$, and more typically, about $10^9$ $M^{-1}$ to $10^{10}$ $M^{-1}$ or stronger; and modulate, e.g., reduce and/or inhibit, one or more TLR2 biological activities in a TLR2 responsive cell and/or tissue.

In certain embodiments, the TLR2 modulator agent is targeted to Toll-like Receptor 2 expressed on the cells of the kidney, in particular the glomerulus or Bowman's capsule. Exemplary TLR2 activities that can be modulated, e.g., inhibited or reduced, using the methods and compositions of the invention include, but are not limited to, one or more of the following: (i) inhibiting or suppressing TLR2 expression, (ii) inhibiting TLR2 ligand binding and associated TLR2 activation, and (iii) inhibiting or suppressing intracellular signalling mediated by TLR2.

Accordingly, in a further aspect, the invention provides a method of modulating a function (e.g., modulating one or more biological activities) of Toll-like Receptor 2 (TLR2) in a TLR2— responsive cell and/or tissue (e.g., a cell or tissue of the kidney). The method includes contacting the TLR2-responsive cell and/or TLR2-responsive tissue with a TLR2 modulator agent, e.g., a TLR2 binding compound, such as an antagonist of human TLR2 activity or expression, in an amount sufficient to modulate the function of the TLR2-responsive cell or tissue, or the biological activity of TLR2 in the cell or tissue. In one embodiment, the contacting step between the TLR2 modulator and the TLR2-responsive cell can be effected in vitro, for example in a cell lysate or in a reconstituted system. Alternatively, said method can be performed on cells in culture, e.g., in-vitro or ex-vivo. For example, cells, such as purified or recombinant cells can be cultured in-vitro and the contacting step can be effected by adding the TLR2 modulator to the culture medium. Typically, the TLR2-responsive cell is a mammalian cell, such as a human cell. In some embodiments, the TLR2-responsive tissue is a tissue of the kidney, or a cellular population associated therewith. In certain further embodiments, the method can be performed on cells present in a subject, for example as part of an in-vivo protocol, or in an animal subject, such as a human, or further in an in-vivo animal model. Said in-vivo protocol can be therapeutic or prophylactic, and the inflammatory model can be, for example, a genetically modified model, such as an animal model having renal inflammation or disease, overexpressed TLR2, or a mutation or deletion in a TLR2 receptor. For in vivo methods, the TLR2 modulator, alone or in combination with another agent, can be administered to a subject suffering from renal disease or inflammation, or a condition which results in kidney disease or failure of normal kidney physiological function, in an amount sufficient to modulate TLR2 expression, or one or more TLR2 mediated activities or functions in a subject. In certain embodiments, the dosage of the TLR2 modulator that is administered to the subject may be determined prior to administration by testing in-vitro or ex-vivo, the amount of TLR2 modulator required to alter, e.g., decrease or inhibit, one or more of TLR2 activities (e.g., one or more TLR2 biological activities described herein).

In certain embodiments where inhibition, reduction or diminution of one or more TLR2 biological activities is desired, the TLR2-responsive cell and/or tissue is contacted with a TLR2 antagonist, e.g., by administering the TLR2 antagonist to the subject. In one embodiment, the TLR2 antagonist interacts with, e.g., binds to, a TLR2 polypeptide or mRNA, and reduces or inhibits one or more TLR2 activities. Typically, the TLR2 antagonized is a mammalian TLR2 (or a functional variant thereof), e.g., human TLR2 or murine TLR2. In certain embodiments, the TLR2 antagonized includes the human TLR2 sequence as defined in FIG. 19 (SEQ ID NO:1) (comprising the 784 amino acid full length human Toll-like Receptor sequence as defined as Genbank Accession Number AAC 34133 (URL www.ncbi.nlm.nih.gov)) or of the murine TLR2 sequence comprising the amino acid sequence defined in FIG. 20 (SEQ ID NO:2) (Genbank Accession Number NP_036035 (*Mus musculus*)), or a portion thereof, and/or a sequence substantially homologous thereto, or encoded by a nucleotide sequence and/or a sequence substantially homologous thereto which encodes the amino acid sequence of SEQ ID NO:1 or SEQ ID NO:2.

As herein defined, the term "Toll-like Receptor 2 activation" means the binding of Toll-like Receptor 2 by a ligand, wherein the ligand acts as an agonist and activates Toll-like Receptor 2 in order to induce an intracellular signalling cascade. Intracellular signalling mediated following Toll-like Receptor 2 activation and signalling results in the activation of transcription factors and the expression of genes which mediate a pro-inflammatory immune response.

In certain embodiments the agent which modulates the function or expression of Toll-like Receptor 2 inhibits the interaction between Toll-like Receptor 2 and a Toll-like Receptor 2 agonist.

In certain embodiments, the modulator agent that suppresses Toll-like Receptor 2 activation and/or signalling is a compound which acts as a Toll-like Receptor 2 antagonist. Typically, antagonism of Toll-like Receptor 2 function is achieved by the binding of the Toll-like Receptor 2 binding agent to Toll-like Receptor 2 in such a way that ligand binding to Toll-like Receptor 2 is prevented. This inhibition of Toll-like Receptor 2 ligand binding may be achieved by a number of means, for example, through partially or fully blocking the Toll-like Receptor 2 ligand binding site, or by inducing a conformational change upon binding to or association with Toll-like Receptor 2 which results in the Toll-like Receptor 2 ligand binding site being altered in a manner which prevents Toll-like Receptor 2 ligand binding, for example due to a conformational change of the tertiary structure of the Toll-like Receptor 2 ligand binding site which precludes binding.

In certain embodiments, the TLR2 modulator agent binds to at least one epitope present on TLR2, wherein binding to this epitope results in an inhibition of TLR2 function, typically activation or TLR2 mediated downstream signalling. As herein defined, an "epitope" refers to a plurality of amino acid residues derived from the TLR2 protein which are capable of being recognised by, and bound to by, a binding compound such as a small molecule, antibody or the like. Epitopes generally comprise chemically active surface groups and have specific three dimensional structural characteristics, as well as specific charge characteristics.

Typically, the TLR2 modulator agent antagonises the functional activity of TLR2 and as such binds to an epitope known as an inhibiting epitope or an inhibitory epitope. An "inhibiting" or "inhibitory" epitope means an epitope present on TLR2 that, when bound by a binding compound such as a small molecule or an antibody, results in the loss of biological activity of TLR2, for example due to the binding compound preventing the binding of TLR2 by a TLR2 agonist. The epitope that is present on TLR2, and which is bound by the binding compounds in order to antagonise TLR2 function, may comprise 5 or more amino acid residues.

In certain embodiments, the TLR2 modulator agents of the invention recognise a continuous epitope. In further embodiments, the epitope is a discontinuous epitope which comprises residues derived from both the N-terminal (amino terminal) and C-terminal (carboxy terminal) portions of the mature Toll-like receptor 2 (TLR2) protein as defined in SEQ ID NO:1. In certain embodiments, the epitope may comprise residues 19 to 39 as determined from the 586 amino acid sequence of Toll-like Receptor 2, said amino acids being KEESSNQASLSCDRNGICKGS (SEQ ID NO:3). Further, the binding epitope may further comprise amino acids residues 538 to 549 of Toll-like Receptor 2 as present at the C-terminal region of the amino acid sequence of SEQ ID NO:1, this sequence comprising the amino acids CSCEFLSFTQEQQ (SEQ ID NO:4). The TLR2 modulatory agent binding site may further be defined by amino acid residues 19 to 39, or 538 to 549 of SEQ ID NO:1, or by amino acid residues 19 to 39, or 538 to 549 of SEQ ID NO:1.

The reduction, inhibition or antagonism of Toll-like Receptor 2 functional activity may occur regardless of whether Toll-like Receptor 2 forms a heterodimer with Toll-like Receptor 1, Toll-like Receptor 6 or another Toll-like Receptor such as Toll-like Receptor 4 or Toll-like Receptor 10. By the term "Toll-like Receptor 2 activation and downstream mediated signaling" it is meant any intracellular signaling pathway which is induced by activated TLR2. The signaling pathway may be a TLR2 specific pathway, or may be a "shared" signalling pathway, for example where the signalling pathway may be activated by other sources, for example, by means of the activation of receptors other than TLR2 which contribute to the activation of mediators of the immune response such as the transcription factor NF-kappaB.

TLR2 is known to dimerise into at least 2 functional heterodimers. Most commonly, TLR2 is known to form a heterodimer with either Toll-like Receptor 1 or Toll-like Receptor 6. Further heterodimers may be formed between TLR2 and Toll-like Receptor 4 (TLR4, TLR-4) and Toll-like Receptor 10 (TLR10, TLR-10). It is thought that this dimerisation is associated with a discrimination that results in the binding of TLR2 by different microbial-derived ligands. In addition, the ectodomain of TLR2 may form a soluble heterodimer with CD14 in the circulatory system and in mammalian milk.

The inventors have surprisingly identified that, in order to provide a therapeutic approach which is comprehensive in suppressing TLR2-mediated inflammation of the kidney, it is desirable to provide a binding compound which has binding specificity for TLR2, regardless of whether a heterodimer is formed with TLR1, TLR6, TLR4 or TLR10. In this regard, following extensive experimentation, the inventors have identified a conformational, discontinuous epitope comprised of amino acid residues present at both the N-terminal and C-terminal of the TLR2 protein which, when bound, results in the global suppression of TLR2 functional activity, that is the function of TLR2 is inhibited irrespective of which TLR TLR2 associates with to form a heterodimer. Accordingly, binding of this epitope by a TLR2 antagonist suppresses the function of TLR2 irrespective of whether TLR2 forms a heterodimer with TLR1, TLR4, TLR6 or TLR10.

As such, in certain further embodiments, the agent which modulates the function or expression of Toll-like Receptor 2 as provided by the present invention may have at least one of the following characteristics: (i) it is a monoclonal antibody, (ii) it is a human-derived or in-vitro generated antibody, (iii) it binds to a conformational, discontinuous epitope comprising the amino acids of SEQ ID NO:3 and/or 4 and mediates TLR2 functional suppression irrespective of whether a heterodimer is formed between TLR2 and TLR1, TLR6, TLR4 or TLR10, (iv) it binds to the epitope defined by the amino acids of the extracellular domain of TLR2, with an affinity constant (Ka) of at least $10^{-6}$M.

In certain embodiments, the agent which modulates the function or expression of Toll-like Receptor 2 is selected from at least one of the group comprising, but not limited to: proteins, peptides, peptidomimetics, nucleic acids, polynucleotides, polysaccharides, oligopeptides, carbohydrates, lipids, small molecule compounds, and naturally occurring compounds.

In certain embodiments, the agent which modulates TLR2 function is a TLR2 antagonist, such as any of the TLR2 agonists or binding compounds described hereinbefore.

In certain embodiments the TLR2 modulatory agent may be a soluble form of recombinant Toll-like Receptor 2. In particular the soluble form of TLR2 may be a fusion protein which substantially comprises the amino acid residues of the extracellular domain on the TLR2 protein conjoined to a secondary protein. In certain embodiments, the secondary protein may be an Fc domain derived from an immunoglobulin, or a fragment thereof.

In certain further embodiments, the TLR2 modulatory agent is an inhibitory nucleic acid which inhibits expression of the TLR2 protein. In certain embodiments the inhibitory nucleic acid protein is selected from the group consisting of: anti-sense oligonucleotides, triple helix molecules, antisense DNA, anti-sense RNA, ribozyme, iRNA, miRNA, siRNA, and shRNA.

In certain embodiments, the methods of the invention are used to administer a TLR2 modulatory agent to a subject in order to reduce or inhibit one or more TLR2 biological activities in a TLR2 expressing cell or tissue of the kidney.

In certain embodiments, the methods of the invention may be used for the treatment or prevention of ischemia reperfusion injury which may result from chronic kidney failure or kidney organ transplantation in a subject.

In certain embodiments, the methods of the invention may comprise the further step of administering a therapeutically effective amount of at least one secondary therapeutic compound along with, the agent which modulates the function or expression of Toll-like Receptor 2. Said secondary therapeutic compound may be, for example, an immunosuppressant compound selected from the group consisting of: a glucocorticoid, a cytostatic, an anti-metabolite, an anti-CD2 antibody or related binding fragment, an anti-CD20 antibody, an anti-TNF-alpha antibody, cyclosporine, tacrolimus, sirolimus or FTY720.

In certain embodiments, the secondary therapeutic agent may be administered simultaneously, sequentially or separately to the administration of the agent which modulates the function or expression of Toll-like Receptor 2.

According to a yet further aspect of the invention there is provided a pharmaceutical composition for use in the treatment and prophylaxis of renal inflammation or disease said composition comprising an agent which modulates the function or expression of Toll-like Receptor 2 along with at least one pharmaceutically acceptable carrier, diluent, solubilizer, emulsifier, preservative and/or adjuvant.

In certain embodiments the renal inflammation is a condition selected from the group comprising: renal disease, including kidney disease, acute renal failure, chronic renal failure or another associated inflammatory condition of the kidney such as glomerulonephritis, or any other condition as hereinbefore described.

In certain embodiments the TLR2 modulatory agent is a compound which is a TLR2 antagonist selected from the group consisting of, but not limited to: a polyclonal antibody, a monoclonal antibody, a humanized antibody, a chimeric antibody or antibody fragment, an aptamer, a fusion protein or a peptidomimetic.

In certain embodiments, the antibody is a murine IgG1 anti-TLR2 antibody (mouse Toll-like Receptor 2 (TLR2) antibody, derived from hybridoma clone T2.5, HyCult Biotechnology b.v., Cell Sciences, Canton, USA: catalogue number 1054), or a humanised version thereof.

In certain embodiments, the TLR2 modulatory agent is a soluble form of the TLR2 receptor, or a fragment thereof. Said soluble form of TLR2 may be produced by recombinant means. In certain embodiments, said soluble form of TLR2 may comprise the extracellular domain of TLR2 or a fragment thereof.

In certain embodiments the TLR2 modulatory agent is an inhibitory nucleic acid based compound which inhibits the expression of TLR2.

In certain embodiments, the pharmaceutical composition may further comprise, or be administered along with at least one secondary therapeutic agent, such as, but not limited to: an immunosuppressant, compound which may be at least one of the group consisting of, but not limited to: a glucocorticoid, in particular a glucocorticoid which suppresses the expression of a cytokine; a cytostatic such as an alkylating agent, an anti-metabolite such as methotrexate; an antibody or related binding fragment, such as an anti-CD3 antibody such as OKT-3, an anti-CD20 antibody, the anti-TNF-alpha antibody infliximab (REMICADE™), etanercept (ENBREL™) or adalimumab (HUMIRA™); a drug compound which acts on immunophilins such as cyclosporine, tacrolimus or sirolimus; or a small molecule, such as FTY720 or a therapeutic cardiovascular compound comprising at least one or more of; an HMG-CoA reductase inhibitor, a vasodilatory agent, a diuretic, an angiotensin converting enzyme inhibitor, a beta-blocker, an angiotensin II receptor antagonist, a calcium channel blocker, an anticoagulant, an adenosine diphosphate receptor antagonist such as ticlopidine or clopidogrel bisulfate, a glycoprotein IIb/IIIa receptor antagonist such as bivalirudin, argatroban or heparin, a beta adrenergic receptor agonist, an antithrombolytic agent, an antioxidant, and an alpha blocker.

In certain embodiments, the Toll-like Receptor 2 modulator agent is orally administered to the subject at a dose of from about 1 mg/kg to about 10 mg/kg of the subject's body weight per day. In certain embodiments, the dose of the Toll-like Receptor 2 modulator agent is from about 100 mg per day to about 1000 mg per day. In certain further embodiments, the dose of the Toll-like Receptor 2 modulator agent is from about 200 mg per day to about 300 mg per day. In certain embodiments, the Toll-like Receptor 2 modulator agent is administered to the subject parenterally with a dosage range of between about 0.001 mg/kg to 1.0 mg/kg of the mammal's body weight.

In certain embodiments, the Toll-like Receptor 2 modulator agent is administered to the subject for a time, and under conditions sufficient to down regulate the level and/or activity of Toll-like Receptor 2.

In certain embodiments the TLR2 modulatory agent is an inhibitory nucleic acid based compound which inhibits the expression of TLR2 by way of blocking the expression of a TLR2 gene, or allowing the expression of mRNA encoding for the TLR2 protein. In certain embodiments, the inhibitory nucleic acid may be selected from the group consisting of: anti-sense oligonucleotides, triple helix molecules, anti-sense DNA, anti-sense RNA, ribozyme, iRNA, miRNA, siRNA, and shRNA.

As herein defined, the terms "blocks" and "blocking" when used in relation to Toll-like Receptor 2 gene expression mean the silencing of the expression of at least one gene which results in the expression of the Toll-like Receptor 2 protein. Gene silencing is the switching off of the expression of a gene by a mechanism other than genetic modification. Gene silencing can be mediated at the transcriptional level or at the post-transcriptional level. Transcriptional gene silencing can results in a gene being inaccessible to transcriptional machinery, and can be mediated, for example, by means of histone modifications. Post-transcriptional gene silencing results from the mRNA of a gene being destroyed, thus preventing an active gene product, such as a protein, in the present case the TLR2 protein.

Accordingly, in one embodiment of this aspect of the invention, there is provided a method for the administration to a subject of an effective amount of an inhibitory nucleic acid molecule such as an RNAi (RNA interference) agent, for example an interfering ribonucleic acid (such as siRNA or shRNA) or a transcription template thereof, such as a DNA encoding an shRNA to at least one cell type, tissue or organ present in the subject in order to block the expression of the TLR2 gene and therefore expression of the TLR2 protein.

In certain further embodiments, the inhibitory nucleic acid molecule may be an antisense RNA molecule. Antisense causes suppression of gene expression and involves single stranded RNA fragments which physically bind to mRNA, this blocking mRNA translation. Techniques for the preparation of appropriate nucleic acids for use as an inhibitory nucleic acid are well known to the person skilled in the art.

According to a further aspect of the invention there is provided the use of an inhibitory nucleic acid which blocks the expression of the Toll-like Receptor 2 protein in the preparation of a medicament for the treatment of renal disease and inflammation.

A further aspect of the present invention provides a pharmaceutical composition for the treatment of renal disease and inflammation, the composition comprising a therapeutically effective amount of an inhibitory nucleic acid which blocks the expression of Toll-like Receptor 2, along with at least one pharmaceutically acceptable carrier, diluent, solubiliser, emulsifier, preservative and/or adjuvant.

In certain embodiments the inhibitory nucleic acid is selected from the group consisting of: anti-sense oligonucleotides, anti-sense DNA, anti-sense RNA, ribozyme, iRNA, miRNA, siRNA, shRNA. In certain embodiments the pharmaceutical composition may further comprise at least one further immunosuppressor compound, as defined hereinbefore.

Techniques for the preparation of appropriate nucleic acids for use as inhibiting nucleic acids which block the expression of Toll-like Receptor 2 are well known to the person skilled in the art.

In a further aspect, the invention extends to the provision of at least one aptamer with binding specificity to Toll-like Receptor 2, which causes blocking or suppression of the functional activity of Toll-like Receptor 2. Techniques for the selection of suitable aptamers will be well known to the person skilled in the art, for example, using SELEX technology.

Accordingly, in various further embodiments, the present invention extends to a method of identifying and isolating nucleic acid ligands which have binding specificity for Toll-like Receptor 2 or a Toll-like Receptor 2 gene product, the method comprising the steps of:
  (a) providing a candidate mixture of nucleic acids
  (b) contacting a cell expressing Toll-like Receptor 2 with the candidate nucleic acid mixture
  (c) selecting nucleic acids which have an increased affinity to Toll-like Receptor 2 relative to the other candidate nucleic acids,
  (d) amplifying the selected nucleic acids in order to provide at least one nucleic acid with affinity for Toll-like Receptor 2, and
  (e) selecting at least one nucleic acid therefrom which has a high affinity and specificity for Toll-like Receptor 2.

The inventors have further identified that suppression of the function of Toll-like Receptor 2 can be achieved by way of reducing the amount of TLR2 binding ligand which is available to bind to and activate membrane bound Toll-like Receptor 2. A reduction in the amount of ligand which is available to bind membrane bound Toll-like Receptor 2 results in a downregulation of Toll-like Receptor 2 mediated signalling and thus of TLR2-mediated activation of the pro-inflammatory immune response. In particular, the inventors have identified the utility of a soluble peptide which is either a soluble form of Toll-like Receptor 2 or a functional fragment thereof, in the suppression of Toll-like Receptor 2 mediated activation of a pro-inflammatory response. Said suppression results from the soluble form of Toll-like Receptor 2 or truncated non-membrane form of Toll-like Receptor 2 competing with the membrane bound form of TLR2 for the binding of TLR2 binding ligands. This competitive binding results in the soluble or truncated forms of TLR2 effectively "mopping up" available Toll-like Receptor 2 ligand, that is, due to the binding of TLR2 ligands to the soluble forms of TLR2, the pool of TLR2 ligands which is available to bindi to and activate membrane bound TLR2 is depleted. An associated reduction in the binding and activation of membrane bound Toll-like Receptor 2 results in a downregulation of the Toll-like Receptor 2 mediated pro-inflammatory immune response.

Accordingly, the administration of a soluble form of Toll-like Receptor 2 has utility in methods for suppressing the pro-inflammatory immune response which contributes to tissue injury during renal inflammation and disease.

The amino acid sequence of the extracellular domain (ectodomain) of human Toll-like Receptor 2 is provided herein as SEQ ID NO:5 (FIG. 21). The extracellular domain of the human form of Toll-like Receptor 2 comprises 587 amino acid resides, specifically amino acids 1-587 of the defined 784 amino acid full length human Toll-like Receptor sequence as defined in SEQ ID NO:1 and also defined as Genbank Accession Number AAC 34133 (URL www.ncbi.nlm.nih.gov). As herein defined, the ectodomain of TLR2 is the portion of the membrane bound form of TLR2 which extends into the extracellular space.

In certain embodiments of the invention, where the TLR2 modulatory agent is a soluble form of TLR2, the soluble form of TLR2 may be prepared by a recombinant technique. A soluble form of Toll-like Receptor 2 typically comprises the extracellular domain of TLR2 only, and hence the intracellular and transmembrane domains of Toll-like Receptor 2 as defined in Genbank Accession Number AAC 34133 are absent. In certain embodiments, the soluble form of Toll-like Receptor 2 may comprise amino acids 1 to 587 of the defined human Toll-like Receptor 2 sequence as shown in SEQ ID NO:1. The soluble Toll-like Receptor 2 sequence may be modified by means of the addition, deletion or substitution of 1 or more amino acid residues. Accordingly, in certain embodiments, the soluble form of the Toll-like Receptor 2 is derived from the extracellular domain of the determined membrane bound form of Toll-like Receptor 2 as defined herein in SEQ ID NO:1. In further embodiments, the soluble form of the Toll-like Receptor 2 is derived from a truncated form of the full length membrane bound Toll-like Receptor 2 amino acid sequence as defined herein in SEQ ID NO:1, wherein said truncated form exhibits the functional characteristics of (i) being soluble, and (ii) being capable of being bound by a ligand which has binding specificity to at least one epitope which is present on the membrane bound form of Toll-like Receptor 2.

In certain embodiments, in addition to a substitution of the amino acid residues relating to the intracellular and/or transmembrane domains derived from the membrane bound form of TLR2, at least one deletion and/or substitution may further be made to the amino acid residues of the extracellular domain of the TLR2 to form a homologous protein. Any number of deletions and/or substitutions to the amino acid residues of the extracellular domain of the TLR2 may be made so long as the resultant peptide is capable of binding a ligand which is capable of binding to at least one epitope present on the membrane bound form of TLR2. The soluble form of the Toll-like Receptor 2 may also comprise a sequence which has at least a 50%, 60%, 70%, 80%, 90%, 95%, 98%, or 99% homology to the amino acid sequence of SEQ ID NO:5. Such homology may be determined by a number of ways which are well known to the person skilled in the art, such as the use of an aligned algorithm. In particular, the percentage identity between two amino acid sequences may be determined, for example, by comparing the amino acid sequences of the 2 proteins using the GAP computer program, version 6.0 described by Devereux et al. (Nucl. Acids Res. 12:387, 1984) and available from the University of Wisconsin Genetics Computer Group (UWGCG). The GAP program utilises the alignment method of Needleman and Wunsch (J. Mol. Biol. 48:443, 1970), as revised by Smith and Waterman (Adv. Appl. Math 2:482, 1981).

In certain embodiments, the soluble form of Toll-like Receptor 2 (sTLR2) may be targeted to the kidney, or in particular to at least one specific cell type which is involved with disease pathogenesis of in an inflamed state, for example the renal tubular epithelial cells (TECs) and/or the epithelial cells of the Bowman's capsule. The targeting of sTLR2 in this way is advantageous as systemic administration of sTLR2 may result in global immunosuppression of the TLR2 receptor and accordingly TLR2 mediated signalling which may be undesirable in some instances.

Targeting of soluble forms of sTLR2 may be provided through the formation of a fusion protein, wherein said fusion protein is comprised of the soluble TLR2 protein, most typically the extracellular domain of TLR2 as described hereinbefore, or a portion thereof, which is linked to a secondary peptide, typically the Fc domain of an immunoglobulin, such as the heavy chain of an immunoglobulin, typically a human immunoglobulin. The Fc domain has been extensively used to prolong the circulatory half-life of therapeutic proteins. The fusion protein may be further modified to improve its half life, or efficacy. A number of techniques for mediating such modifications are known to the person in the art, such a PEGylation, or refolding of the tertiary protein structure.

A yet further aspect of the present invention provides a kit comprising a pharmaceutical preparation comprising an agent which suppresses the function, expression or signalling mediated by a membrane bound form of Toll-like Receptor 2 along with instructions for the administration of said preparation, said kit having utility in the treatment of subjects with kidney disease or inflammation. Typically said agent is a soluble form the Toll-like Receptor 2.

The present invention further extends to screening assays for use in identifying compounds which are capable of preventing TLR2 activation and TLR2 mediated immune responses which contribute to renal inflammation and disease by means of suppressing the function of Toll-like Receptor 2.

A yet further aspect of the present invention provides a screening method for the identification of compounds which suppress Toll-like Receptor 2 mediated inflammation associated with a renal disorder or disease the method comprising:
  providing membrane bound Toll-like Receptor 2 receptor along with a ligand which has binding specificity thereto,
  bringing a candidate compound into contact with the Toll-like Receptor 2,
  exposing the Toll-like Receptor 2 to a Toll-like Receptor 2 ligand agonist,
  determining the binding of the Toll-like Receptor 2 ligand agonist to Toll-like Receptor 2,
wherein the inhibition of binding of Toll-like Receptor 2 by the Toll-like Receptor 2 ligand indicates that said candidate compound is a modulator of Toll-like Receptor 2 activation and signalling.

A further aspect of the present invention provides for the use of a modulator identified according to the previous aspect of the invention in the preparation of a medicament for suppressing a TLR2-mediated inflammatory response for the treatment of renal inflammation and disease.

A further aspect of the present invention provides for a modulator identified by the foregoing assay method for the invention for use in the treatment of renal inflammation and disease.

In certain embodiments the agent which modulates the function or expression of Toll-like Receptor 2 for use in treating renal disease. In certain embodiments, the renal disease is selected from the group consisting of renal disease, chronic renal failure, acute renal failure heterologous nephrotoxic nephritis, glomerulonephritis, sclerosis of the glomerulus, systemic lupus erythematosus (SLE), diabetic nephropathy, and diabetic nephropathy.

In certain embodiments the agent is selected from the group consisting of a protein, a peptide, a peptidomimetic, a nucleic acid, a carbohydrate, a lipid, and a small molecule compound. In certain embodiments, the agent is an antibody which has binding specificity to human TLR2. In certain embodiments the antibody is selected from the group consisting of a human, humanised, chimeric, synthetic, camelid, shark or in-vitro antibody which has binding specificity to TLR2, or a binding fragment derived from any of the same.

In certain embodiments, the agent is a TLR2 antagonist which binds to an epitope defined by the extracellular domain of human TLR2. In certain embodiments, the agent is a TLR2 antagonist which binds to a non-continuous epitope comprising amino acid residues derived from the amino and carboxyl terminals of the amino acid sequence of human TLR2.

In certain embodiments of this aspect of the invention, the agent inhibits the expression of nucleic acid encoding the TLR2 protein. In certain embodiments, the agent is selected from the group consisting of an anti-sense oligonucleotides, triple helix molecules, anti-sense DNA, anti-sense RNA, ribozyme, iRNA, miRNA, siRNA, shRNA molecule.

In certain embodiments of this aspect of the invention, the agent is a soluble form of Toll-like Receptor 2. Typically, the soluble form of Toll-like Receptor 2 comprises an amino acid sequence as defined in SEQ ID NO:5, or a fragment thereof.

The inventors have identified that TLR2 mediated signalling and activation of the immune response results in the upregulation of levels of the cytokine IL-8. The expression of this cytokine has been identified by the inventors as being one of the key inflammatory mediators in stimulating renal inflammation, and the progress of disease conditions caused by renal inflammation.

Accordingly, a further aspect of the present invention provides a method of suppressing Toll-like Receptor 2-mediated IL-8 production by at least one cell type of the kidney, the method comprising the step of:
  providing a therapeutically effective amount of an agent which modulates the functional activity or expression of Toll-like Receptor 2 (TLR2), and
  administering the same to a subject in need of such treatment.

In certain embodiments the TLR2 modulator agent is a TLR2 antagonist selected from the group comprising, but not limited to: a protein, a peptide, a peptidomimetic, a nucleic acid, a carbohydrate, a lipid, an aptamer and a small molecule compound. In certain embodiments the TLR2 antagonist is an antibody molecule. In further embodiments, the TLR2 antagonist is a fusion protein, for example a fusion protein comprising a soluble fragment of TLR2. In certain further embodiments, the TLR2 modulator agent is an inhibitory nucleic acid which includes, but is not limited to; anti-sense oligonucleotides, anti-sense DNA, anti-sense RNA, ribozyme, iRNA, miRNA, siRNA, shRNA.

BRIEF DESCRIPTION OF THE FIGURES

Toll-like Receptor 2 deficient mice treated with either 30 mg/kg intraperitoneal (i.p.) prednisol (pred), PBS control 9PBS), 10 mg/kg intravenous (i.v.) isotype control antibody (cont) or 10 mg/kg intravenous anti-TLR2 antibody OPN301 (opn301) followed by immunization with 10 ug of the lipopeptide Pam3CysSK4, FIG. 19 shows the amino acid sequence of human Toll-like Receptor 2 (SEQ ID NO:1), FIG. 20 shows the amino acid sequence of human Toll-like Receptor 2 (SEQ ID NO:2), and FIG. 21 shows the amino acid sequence of the extracellular domain of human Toll-like Receptor 2 (SEQ ID NO:3).

DETAILED DESCRIPTION OF THE INVENTION

Figure 1:
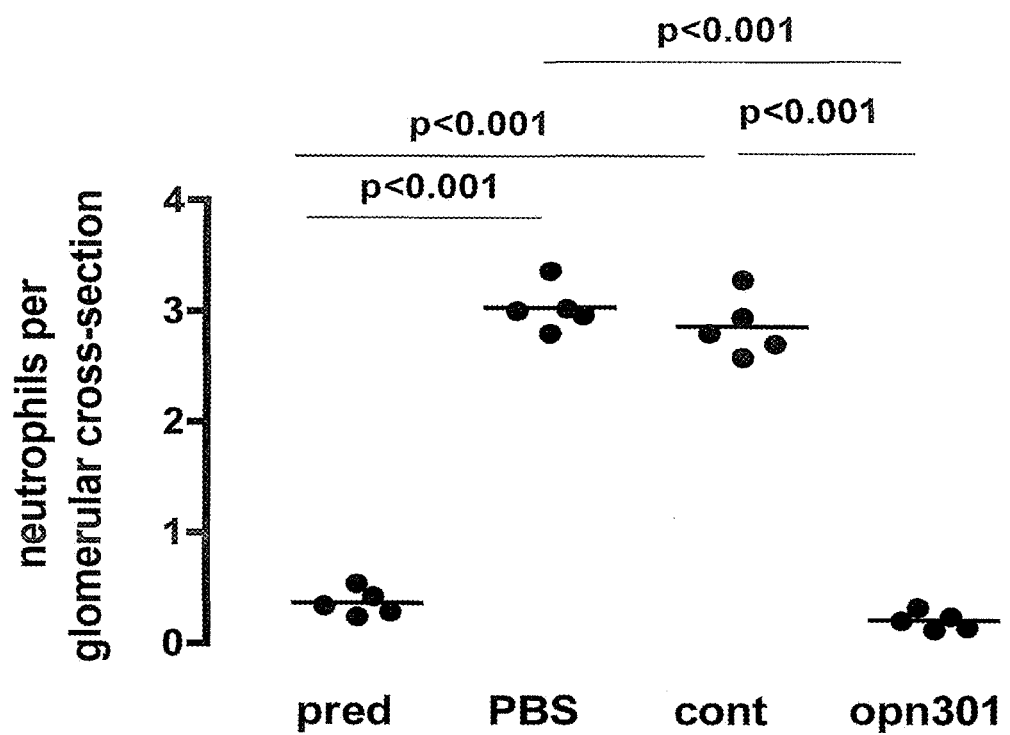
FIG. 1 shows a dot plot graph illustrating the number of neutrophils per glomerula in a glomerular cross section obtained from extracted kidneys of C57BL/6 Toll-like Receptor 2 deficient mice treated with either 30 mg/kg intraperitoneal (i.p.) prednisol (pred), PBS control (PBS), 10 mg/kg intravenous (i.v.) isotype control antibody (cont) or 10 mg/kg intravenous (i.v.) anti-TLR2 antibody OPN301 (opn301) followed by immunization with 10 ug of the lipopeptide Pam3CysSK4.

The present invention relates to agents which inhibit the function or expression of Toll-like Receptor 2 (TLR2), or to methods which use such agents for the treatment of renal disease and inflammation, and in particular for the treatment or prophylaxis of inflammation of the glomeruli as well as kidney diseases mediated by Toll-like Receptor 2 signaling.

TLR2 modulator agents such as TLR2 antagonistic binding compounds, which have affinity and binding specificity to a binding epitope of TLR2 have utility in the inhibition of a number of immune mediated and disease conditions which affect the kidney. As such, the present invention provides compositions and methods for the treatment and prophylaxis of immune-mediated, inflammatory and pathogenic conditions which target the kidney, or which affect kidney function.

In certain embodiments, the pathogenic condition is an infectious condition mediated by a bacterial pathogen. The bacterial pathogen may be a gram positive bacteria, or a gram negative bacteria. In certain embodiments, the bacterial pathogenic is a sepsis-causing bacteria, said compositions and methods having utility in the treatment of kidney related inflammation arising from conditions such as sepsis or septic shock, for example gram negative sepsis.

The term "epitope" as used herein relates to a portion of a macromolecule, in this case the TLR2 protein, or a related protein, which is capable of being bound by a specific binding ligand, in this case a Toll-like Receptor 2 ligand agonist. Epitopes may be defined from contiguous or non-contiguous sequences of amino acid residues comprised within a polypeptide sequence. The term "contiguous epitope" defines an epitope comprised of a linear series of amino acid residues within a polypeptide which define the epitope. A "non-contiguous epitope" is an epitope which is comprised of a series of amino acid residues which are non-linear in alignment, that is that the residues are spaced or grouped in a non-continuous manner along the length of a polypeptide sequence. A non-continuous epitope can be a discontinuous epitope wherein the amino acid residues are grouped into 2 linear sequences, or alternatively the non-continuous epitope can be a discontinuous scattered epitope wherein the residues which contribute to the epitope are provided in 3 or more groups of linear amino acid sequences arranged along the length of the polypeptide.

Antibodies

An "antibody" is an immunoglobulin, whether natural or partly or wholly synthetically produced. The term also covers any polypeptide, protein or peptide having a binding domain that is, or is homologous to, an antibody binding domain. These can be derived from natural sources, or they may be partly or wholly synthetically produced. Examples of antibodies are the immunoglobulin isotypes and their isotypic subclasses and fragments which comprise an antigen binding domain such as Fab, scFv, Fv, dAb, Fd, and a bi-specific antibody.

In further embodiments, the antibody may be a Camelid antibody, in particular a Camelid heavy chain antibody. Further the antibody fragment may be a domain antibody or a nanobody derived from a Camelid heavy chain antibody. In a further embodiment the antibody may be a shark antibody or a shark derived antibody.

In certain embodiments, the antibody is an "isolated antibody", this meaning that the antibody is (1) free of at least some proteins with which it would normally be found, (2) is essentially free of other proteins from the same source, e.g., from the same species, (3) is expressed by a cell from a different species, or (4) does not occur in nature.

As antibodies can be modified in a number of ways, the term "antibody" should be construed as covering any binding member or substance having a binding domain with the required specificity. The antibody of the invention may be a monoclonal antibody, or a fragment, derivative, functional equivalent or homologue thereof. The term includes any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in European Patent Application Publication Number EP 0,120,694 and European Patent Application Publication Number EP 0,125,023.

The constant region of the antibody may be of any suitable immunoglobulin subtype, however it is preferred that the antibody subtype is IgG1. However, in alternative embodiments, the subtype of the antibody may be of the class IgA, IgM, IgD and IgE where a human immunoglobulin molecule is used. Such an antibody may further belong to any subclass e.g. IgG1, IgG2a, IgG2b, IgG3 and IgG4.

Fragments of a whole antibody can perform the function of antigen binding. Examples of such binding fragments are; a Fab fragment comprising of the VL, VH, CL and CH1 antibody domains; an Fv fragment consisting of the VL and VH domains of a single antibody; a F(ab')2 fragments, a bivalent fragment comprising two linked Fab fragments; a single chain Fv molecule (scFv), wherein a VH domain and a VL domain are linked by a peptide linker which allows the two domains to associate to form an antigen binding site; or a bi-specific antibody, which may be multivalent or multispecific fragments constructed by gene fusion.

A fragment of an antibody or of a polypeptide for use in the present invention, for example, a fragment of a TLR2 specific antibody, generally means a stretch of amino acid residues of at least 5 to 7 contiguous amino acids, often at least about 7 to 9 contiguous amino acids, typically at least about 9 to 13 contiguous amino acids, more preferably at least about 20 to 30 or more contiguous amino acids and most preferably at least about 30 to 40 or more consecutive amino acids.

A "derivative" of such an antibody or polypeptide, or of a fragment of a TLR2 specific antibody means an antibody or polypeptide modified by varying the amino acid sequence of the protein, e.g. by manipulation of the nucleic acid encoding the protein or by altering the protein itself. Such derivatives of the natural amino acid sequence may involve insertion, addition, deletion and/or substitution of one or more amino acids, preferably while providing a peptide having TLR2 binding activity. Preferably such derivatives involve the insertion, addition, deletion and/or substitution of 25 or fewer amino acids, more preferably of 15 or fewer, even more preferably of 10 or fewer, more preferably still of 4 or fewer and most preferably of 1 or 2 amino acids only.

The term "antibody" includes antibodies which have been "humanised". Methods for making humanised antibodies are known in the art. Methods are described, for example, in Winter, U.S. Pat. No. 5,225,539. A humanised antibody may be a modified antibody having the hypervariable region of a monoclonal antibody such as a TLR2 specific antibody and the constant region of a human antibody. Thus the binding member may comprise a human constant region.

The variable region other than the hypervariable region may also be derived from the variable region of a human antibody and/or may also be derived from a monoclonal antibody such as a TLR2 specific antibody. In such case, the entire variable region may be derived from murine monoclonal antibody a TLR2 specific antibody and the antibody is said to be chimerised. Methods for making chimerised antibodies are known in the art. Such methods include, for example, those described in U.S. patents by Boss (Celltech) and by Cabilly (Genentech). See U.S. Pat. Nos. 4,816,397 and 4,816,567, respectively.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, the teachings of EP 0,184,187, GB 2,188,638A or EP 0,239,400. A hybridoma or other cell producing an antibody may be subject to genetic mutation or other changes, which may or may not alter the binding specificity of antibodies produced.

In certain embodiments, where the TLR2 inhibitory compound or TLR2 binding compound of the invention is an antibody, the antibody is administered to a subject in a therapeutically effective amount. In certain embodiments, the therapeutically effective amount comprises the antibody in a range chosen from 1 µg/kg to 20 mg/kg, 1 g/kg to 10 mg/kg, 1 µg/kg to 1 mg/kg, 10 µg/kg to 1 mg/kg, 10 µg/kg to 100 µg/kg and 500 µg/kg to 1 mg/kg.

Production of Antibodies

The antibodies provided by the present invention may be provided by a number of techniques. For example, a combinatorial screening technique such as a phage display-based biopanning assay may be used to in order to identify amino acid sequences which have binding specificity to the binding epitopes of the invention. Such phage display biopanning techniques involve the use of phage display libraries, which are utilised in methods which identify suitable epitope binding ligands in a procedure which mimics immune selection, through the display of antibody binding fragments on the surface of filamentous bacteria. Phage with specific binding activity are selected. The selected phage can thereafter be used in the production of chimeric, CDR-grafted, humanised or human antibodies.

In further embodiments, the antibody is a monoclonal antibody may be produced using any suitable method which produces antibody molecules by continuous cell lines in culture. Suitable methods will be well known to the person skilled in the art and include, for example, the method of Kohler and Milstein (Kohler et al. Nature, 256, 495-497. 1975), Chimeric antibodies or CDR-grafted antibodies are further provided within the scope of the present invention. In further embodiments, the antibodies of the invention may be produced by the expression of recombinant DNA in host cell.

In further embodiments, humanized antibodies are also provided. Humanized antibodies may be produced by the method of Winter as described in U.S. Pat. No. 5,585,089.

In further certain embodiments, the monoclonal antibodies may be human antibodies, produced using transgenic animals, for example, transgenic mice, which have been genetically modified to delete or suppress the expression of endogenous murine immunoglobulin genes, with loci encoding for human heavy and light chains being expressed in preference, this resulting in the production of fully human antibodies.

In certain further embodiments, the binding compound is a binding fragment which is derived from an antibody, for example, an antibody binding fragment, such as a Fab, F(ab') 2, Fv or a single chain Fv (scFV).

In certain further embodiments, the binding compound comprises a polyclonal antibody, a chimeric antibody, a synthesized or synthetic antibody, a fusion protein or fragment thereof, or a natural or synthetic chemical compound or a peptidomimetic.

Certain methodologies for producing antibodies which have an affinity and binding specificity for the Toll-like Receptor 2 epitope of the present invention are described hereinbefore.

The antibodies or antibody fragments of and for use in the present invention may also be generated wholly or partly by chemical synthesis. The antibodies can be readily prepared according to well-established, standard liquid or, preferably, solid-phase peptide synthesis methods, general descriptions of which are broadly available and are well known by the person skilled in the art. Further, they may be prepared in solution, by the liquid phase method or by any combination of solid-phase, liquid phase and solution chemistry.

Another convenient way of producing antibodies or antibody fragments suitable for use in the present invention is to express nucleic acid encoding them, by use of nucleic acid in an expression system.

Nucleic acid for use in accordance with the present invention may comprise DNA or RNA and may be wholly or partially synthetic. In a preferred aspect, nucleic acid for use in the invention codes for antibodies or antibody fragments of the invention as defined above. The skilled person will be able to determine substitutions, deletions and/or additions to such nucleic acids which will still provide an antibody or antibody fragment of the present invention.

Nucleic acid sequences encoding antibodies or antibody fragments for use with the present invention can be readily prepared by the skilled person using the information and references contained herein and techniques known in the art (for example, see Sambrook et al. (1989), and Ausubel et al, (1992)), given the nucleic acid sequences and clones available. These techniques include (i) the use of the polymerase chain reaction (PCR) to amplify samples of such nucleic acid, e.g. from genomic sources, (ii) chemical synthesis, or (iii) preparing cDNA sequences. DNA encoding antibody fragments may be generated and used in any suitable way known to those of skill in the art, including by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Modifications to the sequences can be made, e.g. using site directed mutagenesis, to lead to the expression of modified peptide or to take account of codon preferences in the host cells used to express the nucleic acid.

The nucleic acid may be comprised as constructs in the form of a plasmid, vector, transcription or expression cassette which comprises at least one nucleic acid as described above. The construct may be comprised within a recombinant host cell which comprises one or more constructs as above. Expression may conveniently be achieved by culturing under appropriate conditions recombinant host cells containing the nucleic acid. Following production by expression the antibody or antibody fragments may be isolated and/or purified using any suitable technique, then used as appropriate.

Systems for cloning and expression of a polypeptide in a variety of different host cells are well known. Suitable host cells include bacteria, mammalian cells, yeast, insect and baculovirus systems. Mammalian cell lines available in the art for expression of a heterologous polypeptide include Chinese hamster ovary (CHO) cells, HeLa cells, baby hamster kidney cells, NS0 mouse myeloma cells. A common, preferred bacterial host is E. coli. The expression of antibodies and antibody fragments in prokaryotic cells such as E. coli is well established in the art. Expression in eukaryotic cells in culture is also available to those skilled in the art as an option for production of a binding member.

General techniques for the production of antibodies are well known to the person skilled in the field, with such methods being discussed in, for example, Kohler and Milstein (1975) Nature 256: 495-497; U.S. Pat. No. 4,376,110; Harlow and Lane, Antibodies: a Laboratory Manual, (1988) Cold Spring Harbor, the contents of which are incorporated herein by reference.

Techniques for the preparation of recombinant antibody molecules are described in the above references and also in, for example, EP 0,623,679 and EP 0,368,684 which are incorporated herein by reference.

In certain embodiments of the invention, recombinant nucleic acids comprising an insert coding for a heavy chain variable domain and/or for a light chain variable domain of antibodies are employed. By definition such nucleic acids comprise coding single stranded nucleic acids, double stranded nucleic acids consisting of said coding nucleic acids and of complementary nucleic acids thereto, or these complementary (single stranded) nucleic acids themselves.

Furthermore, nucleic acids encoding a heavy chain variable domain and/or a light chain variable domain of antibodies can be enzymatically or chemically synthesised nucleic acids having the authentic sequence coding for a naturally-occurring heavy chain variable domain and/or for the light chain variable domain, or a mutant thereof.

Recombinant DNA technology may be used to improve the antibodies of the invention. Thus, chimeric antibodies may be constructed in order to decrease the immunogenicity thereof in diagnostic or therapeutic applications. Moreover, immunogenicity within, for example, a transgenic organism such as a pig, may be minimised, by altering the antibodies by CDR grafting in a technique analogous to humanising antibodies. Examples of such techniques are described in EP 0,239,400 to Winter. In order to reduce immunogenicity within a recipient, the invention may employ recombinant nucleic acids comprising an insert coding for a heavy chain variable domain of an antibody fused to a human constant domain. Likewise the invention concerns recombinant DNAs comprising an insert coding for a light chain variable domain of an antibody fused to a human constant domain kappa or lambda.

Antibodies may moreover be generated by mutagenesis of antibody genes to produce 5 artificial repertoires of antibodies. This technique allows the preparation of antibody libraries. Antibody libraries are also available commercially. Hence, the present invention advantageously employs artificial repertoires of immunoglobulins, preferably artificial scFv repertoires, as an immunoglobulin source in order to identify binding molecules which have specificity for the epitope of the present invention.

Antibody Selection Systems

Immunoglobulins which are able to bind to the epitope of the present invention and which accordingly may be used in the methods of the invention can be identified using any technique known to the skilled person. Such immunoglobulins may be conveniently isolated from libraries comprising artificial repertoires of immunoglobulin polypeptides. A "repertoire" refers to a set of molecules generated by random, semi-random or directed variation of one or more template molecules, at the nucleic acid level, in order to provide a multiplicity of binding specificities. Methods for generating repertoires are well characterised in the art.

Any library selection system may be used in conjunction with the invention. Selection protocols for isolating desired members of large libraries are known in the art, as typified by phage display techniques. Such systems, in which diverse peptide sequences are displayed on the surface of filamentous bacteriophage, have proven useful for creating libraries of antibody fragments (and the nucleotide sequences that encode them) for the in vitro selection and amplification of specific antibody fragments that bind a target antigen. The nucleotide sequences encoding the VH and VL regions are linked to gene fragments which encode leader signals that direct them to the periplasmic space of E. coli and as a result the resultant antibody fragments are displayed on the surface of the bacteriophage, typically as fusions to bacteriophage coat proteins (e.g., pIII or pVIII). Alternatively, antibody fragments are displayed externally on lambda phage capsids (phage bodies). An advantage of phage-based display systems is that, because they are biological systems, selected library members can be amplified simply by growing the phage containing the selected library member in bacterial cells. Furthermore, since the nucleotide sequence that encodes the polypeptide library member is contained on a phage or phagemid vector, sequencing, expression and subsequent genetic manipulation is relatively straight forward.

Methods for the construction of bacteriophage antibody display libraries and lambda phage expression libraries are well known in the art (for example, McCafferty et al. (1990) Nature 348 552-554. One particularly advantageous approach has been the use of scFv phage-libraries (see for example Huston et al., 1988, Proc. Natl. Acad. Sci. USA).

An alternative to the use of phage or other cloned libraries is to use nucleic acid, preferably RNA, derived from the B cells of an animal which has been immunised with the selected target, e.g. the TLR2 epitope of the present invention.

Isolation of V-region and C-region mRNA permits antibody fragments, such as Fab or Fv, to be expressed intracellularly. Briefly, RNA is isolated from the B cells of an immunised animal, for example from the spleen of an immunised mouse or the circulating B cells of a llama, and PCR primers used to amplify VH and VL cDNA selectively from the RNA pool. The VH and VL sequences thus obtained are joined to make scFv antibodies. PCR primer sequences may be based on published VH and VL sequences.

Peptidomimetics

Peptide analogues, such as peptidomimetics or peptide mimetics are non-peptide compounds with properties representative of a template peptide. Such peptide analogues are typically developed using computerised molecular modelling. Peptidomimetics which are structurally similar to peptides which have affinity and binding specificity to the TLR2 binding epitope of the present invention may be used to mediate similar diagnostic, prophylactic and therapeutic effects.

Peptidomimetics are typically structurally similar to a template peptide, but have one or more peptide linkages replaced by an alternative linkage, by methods which are well known in the art. For example, a peptide which has a binding specificity for the TLR2 epitope of the invention may be modified such that it comprises amide bond replacement, incorporation of non peptide moieties, or backbone cyclisation. Suitably if cysteine is present the thiol of this residue is capped to prevent damage of the free sulphate group. A peptide may further be modified from the natural sequence to protect the peptides from protease attack.

Suitably a peptide of and for use in the present invention may be further modified using at least one of C and/or N-terminal capping, and/or cysteine residue capping.

Suitably, a peptide of and for use in the present invention may be capped at the N terminal residue with an acetyl group. Suitably, a peptide of and for use in the present invention may be capped at the C terminal with an amide group. Suitably, the thiol groups of cysteines are capped with acetamido methyl groups.

Expression, isolation and purification of polypeptides defining the epitope of the invention and fragments thereof may be accomplished by any suitable technique.

A method for producing polypeptides comprises culturing host cells transformed with a recombinant expression vector encoding a polypeptide under conditions that promote expression of the polypeptide, then recovering the expressed polypeptides from the culture. The skilled man will recognise that the procedure for purifying the expressed polypeptides will vary according to such factors as the type of host cells employed, and whether the polypeptide is intracellular, membrane-bound or a soluble form that is secreted from the host cell.

Any suitable expression system may be employed. The vectors include a DNA encoding a polypeptide or fragment of the invention, operably linked to suitable transcriptional or translational regulatory nucleotide sequences, such as those derived from a mammalian, avian, microbial, viral, bacterial, or insect gene. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired (*E. coli*) host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide during translation, but allows secretion of polypeptide from the cell.

Suitable host cells for expression of polypeptides include higher eukaryotic cells and yeast. Prokaryotic systems are also suitable. Mammalian cells, and in particular Chinese hamster ovary (CHO) cells are particularly preferred for use as host cells. Appropriate cloning and expression vectors for use with mammalian, prokaryotic, yeast, fungal and insect cellular hosts are described, for example, in Pouwels et al. Cloning Vectors: A Laboratory Manual, Elsevier, New York, (1986) (ISBN 0444904018).

Small Molecules

In various further aspects, the present invention relates to screening and assay methods for use in identifying compounds which antagonise TLR2 activity. Certain further aspects extend to the compounds identified thereby, wherein said binding compounds have affinity and binding specificity for the epitope of the invention.

A substance identified as a ligand of the TLR2 receptor may be a peptide or may be non-peptide in nature, for example a peptidomimetic as described hereinbefore. However, non-peptide "small molecules" are often preferred for many in-vivo pharmaceutical uses. Accordingly, a mimetic or mimic of a TLR2 binding compound for use in the present invention may be designed for pharmaceutical uses.

The designing of mimetics to a known pharmaceutically active compound is a known approach to the development of pharmaceuticals based on a "lead" compound. This might be desirable where the active compound is difficult or expensive to synthesise, or where it is unsuitable for a particular method of administration. For example, peptides are not well suited as active agents for oral compositions and administration as they are degraded by proteases present in the alimentary canal. Mimetic design, synthesis and testing may be used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, for example by substituting each amino acid residue in turn. These parts or residues constituting the active region of the compound are known as its "pharmacophore".

Once the pharmacophore has been determined, its structure is modelled according to its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can also be used in this modelling process.

In a variant of this approach, the three-dimensional structure of the TLR2 binding compound is modelled. This can be especially useful where the ligand and/or binding partner change conformation on binding, allowing the model to take account of the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in-vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in-vivo or clinical testing.

In certain embodiments, the mimetic binding compound may be a natural or synthetic chemical compound used in drug screening programmes. Extracts of plants which contain several characterised or uncharacterised components may also be used.

A candidate binding compound which has affinity and binding specificity to TLR2 may be isolated and/or purified, manufactured and/or used to modulate TLR2 functional activity.

In yet further aspects, the invention extends to the use of combinatorial library technology (Schultz, JS (1996) Biotechnol. Prog. 12:729-743) which provides an efficient way of testing a potentially vast number of different substances for ability their ability to bind to an epitope or to modulate the activity of a ligand which binds to an epitope. Prior to, or as well as, being screened for modulation of activity, test substances may be screened for ability to interact with the polypeptide, e.g. in a yeast two-hybrid system (which requires that both the polypeptide and the test substance can be expressed in yeast from encoding nucleic acid). This may be used as a coarse screen prior to testing a substance for actual ability to modulate activity of the polypeptide.

The amount of test substance or compound which may be added to an assay of the invention will normally be determined by trail and error depending upon the type of compound used. Typically, from about 0.01 to 100 nM concentrations of putative inhibitor compound may be used, for example from 0.1 to 10 nM. Greater concentrations may be used when a peptide is the test substance.

Combination Medicaments

As described hereinbefore, the present invention extends to combinational therapies wherein compositions or methods relates to the administration of a binding compound which inhibits the functional activity of TLR2 are administered in combination with at least one further therapeutic compound which serves to suppress the immune response which may contribute to acute renal failure chronic renal failure or renal disease.

Typically the primary and secondary therapeutic compositions are given contemporaneously. In certain embodiments, the primary therapeutic composition (i.e. the binding compound which antagonises the functional activity of TLR2) and the secondary therapeutic compounds are administered simultaneously. In certain further embodiments, they are administered sequentially.

In certain embodiments, the combination therapy may comprise a TLR2 functional inhibitor which is co-administered to a subject along with at least one of: a cytokine inhibitor, such as, but not limited to an inhibitor of IL-1, IL-6, IL-8 and IL-15, and inhibitor of tumour necrosis factor, a growth factor inhibitor, an immunosuppressor, an anti-inflammatory, an enzymatic inhibitor, a metabolic inhibitor, a cytotoxic agent or a cytostatic agent.

A person of relevant skill in the field will recognise that the administration to a subject of a combination therapy can be advantageous in that it permits administration of a lower dose of therapeutic to a subject in order to achieve and associated therapeutically effective effect. The administration of a lower combined dose also results in the subject being exposed to a lower toxicity level. Furthermore, as the secondary therapeutic compounds which are administered as part of the combination therapy provided by the invention target different pathways, there is likely to be a synergistic improvement in the overall efficacy of the therapy. An improvement in efficacy would again result in the need for a lower dose to be administered and as such an associated reduction in toxicity.

In identifying and selecting suitable secondary therapeutic compounds for administration along with the TLR2 inhibitory compounds of the present invention, said secondary therapeutic compounds may be selected on the basis of such compounds modulating the immune response at a different stage of the inflammatory response which results in renal inflammation and disease. Such secondary compounds may include, but are not limited to; soluble receptors, peptide inhibitor compound, small molecule, fusion proteins or ligands, antibodies, and cytokines which mediate an anti-inflammatory effect.

Administration

The monoclonal antibody or fusion protein of the present invention may be administered alone but will preferably be administered as a pharmaceutical composition, which will generally comprise a suitable pharmaceutically acceptable excipient, diluent or carrier selected depending on the intended route of administration. Examples of suitable pharmaceutical carriers include; water, glycerol, ethanol and the like.

The monoclonal antibody or fusion protein of the present invention may be administered to a patient in need of treatment via any suitable route. As detailed herein, it is preferred that the composition is administered parenterally by injection or infusion. Examples of preferred routes for parenteral administration include, but are not limited to; intravenous, intracardial, intraarterial, intraperitoneal, intramuscular, intracavity, subcutaneous, transmucosal, inhalation or transdermal.

Routes of administration may further include topical and enteral, for example, mucosal (including pulmonary), oral, nasal, rectal.

In preferred embodiments, the composition is deliverable as an injectable composition. For intravenous, intradermal or subcutaneous application, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection or, Lactated Ringer's injection. Preservatives, stabilisers, buffers, antioxidants and/or other additives may be included, as required.

The composition may also be administered via microspheres, liposomes, other microparticulate delivery systems or sustained release formulations placed in certain tissues including blood.

Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition ISBN 0-912734-04-3 and Pharmaceutical Dosage Forms and Drug Delivery Systems; Ansel, H. C. et al. 7th Edition ISBN 0-683305-72-7, the entire disclosures of which is herein incorporated by reference.

The composition is preferably administered to an individual in a "therapeutically effective amount", this being sufficient to show benefit to the individual to whom the composition is administered. The actual dose administered, and rate and time-course of administration, will depend on, and can be determined with due reference to, the nature and severity of the condition which is being treated, as well as factors such as the age, sex and weight of the patient to be treated and the route of administration. Further due consideration should be given to the properties of the composition, for example, its binding activity and in-vivo plasma life, the concentration of the fusion protein in the formulation, as well as the route, site and rate of delivery.

Dosage regimens can include a single administration of the composition of the invention, or multiple administrative doses of the composition. The compositions can further be administered sequentially or separately with other therapeutics and medicaments which are used for the treatment of the condition for which the fusion protein of the present invention is being administered to treat.

Examples of dosage regimens which can be administered to a subject can be selected from the group comprising, but not limited to; 1 µg/kg/day through to 20 mg/kg/day, 1 µg/kg/day through to 10 mg/kg/day, 10 µg/kg/day through to 1 mg/kg/day.

The TLR2 epitope binding compound of the present invention is preferably administered to an individual in a "therapeutically effective amount", this being sufficient to show benefit to the individual.

The actual amount administered, and rate and time-course of administration, will depend on the nature and severity of what is being treated. Prescription of treatment, e.g. decisions on dosage etc, is ultimately within the responsibility and at the discretion of general practitioners and other medical doctors, and typically takes account of the disorder to be treated, the condition of the individual patient, the site of delivery, the method of administration and other factors known to practitioners.

Unless otherwise defined, all technical and scientific terms used herein have the meaning commonly understood by a person who is skilled in the art in the field of the present invention.

Throughout the specification, unless the context demands otherwise, the terms 'comprise' or 'include', or variations such as 'comprises' or 'comprising', 'includes' or 'including' will be understood to imply the inclusion of a stated integer or group of integers, but not the exclusion of any other integer or group of integers.

As used herein, terms such as "a", "an" and "the" include singular and plural referents unless the context clearly demands otherwise. Thus, for example, reference to "an active agent" or "a pharmacologically active agent" includes a single active agent as well as two or more different active agents in combination, while references to "a carrier" includes mixtures of two or more carriers as well as a single carrier, and the like.

The nomenclature used to describe the polypeptide constituents of the fusion protein of the present invention follows the conventional practice wherein the amino group (N) is presented to the left and the carboxy group to the right of each amino acid residue.

The expression "amino acid" as used herein is intended to include both natural and synthetic amino acids, and both D and L amino acids. A synthetic amino acid also encompasses chemically modified amino acids, including, but not limited to salts, and amino acid derivatives such as amides. Amino acids present within the polypeptides of the present invention can be modified by methylation, amidation, acetylation or substitution with other chemical groups which can change the circulating half life without adversely affecting their biological activity.

The terms "peptide", "polypeptide" and "protein" are used herein interchangeably to describe a series of at least two amino acids covalently linked by peptide bonds or modified peptide bonds such as isosteres. No limitation is placed on the maximum number of amino acids which may comprise a peptide or protein. Furthermore, the term polypeptide extends to fragments, analogues and derivatives of a peptide, wherein said fragment, analogue or derivative retains the same biological functional activity as the peptide from which the fragment, derivative or analogue is derived Furthermore the term "fusion protein" as used herein can also be taken to mean a fusion polypeptide, fusion peptide or the like, or may also be referred to as an immunoconjugate. The term "fusion protein" refers to a molecule in which two or more subunit molecules, typically polypeptides, are covalently or non-covalently linked.

As used herein, the term "effective amount" or "therapeutically effective amount" means the amount of an agent, binding compound, small molecule, fusion protein or peptidomimetic of the invention which is required to suppress TLR2-mediated inflammation in the kidney or which reduces the severity of and/or ameliorates a TLR2 mediated renal disease or at least one symptom thereof or condition associated therewith.

As used herein, the term "prophylactically effective amount" relates to the amount of a composition which is required to prevent the initial onset, progression or recurrence of TLR2-mediated inflammation of the kidney, or renal disease, or at least one symptom thereof in a subject following the administration of the compounds of the present invention.

As used herein, the term "treatment" and associated terms such as "treat" and "treating" means the reduction of the progression, severity and/or duration of a TLR2 mediated condition of at least one symptom thereof, wherein said reduction or amelioration results from the administration of a binding compound which has specificity for the TLR2 binding epitope of the present invention. The term 'treatment' therefore refers to any regimen that can benefit a subject. The treatment may be in respect of an existing condition or may be prophylactic (preventative treatment). Treatment may include curative, alleviative or prophylactic effects. References herein to "therapeutic" and "prophylactic" treatments are to be considered in their broadest context. The term "therapeutic" does not necessarily imply that a subject is treated until total recovery. Similarly, "prophylactic" does not necessarily mean that the subject will not eventually contract a disease condition.

As used herein, the term "subject" refers to an animal, preferably a mammal and in particular a human. In a particular embodiment, the subject is a mammal, in particular a human. The term "subject" is interchangeable with the term "patient" as used herein.

The present invention will now be described with reference to the following examples which are provided for the purpose of illustration and are not intended to be construed as being limiting on the present invention.

EXAMPLES

Example 1

Effect of Toll-like Receptor 2 Agonist on Glomerular Inflammation

Methods

Methods for generating nephrotoxic antibody, blood counts, processing histology, assessment of histology are disclosed in Brown H J, Lock, H R, Sacks S H, Robson M G TLR2 stimulation of intrinsic kidney cells in the induction of immune mediated glomerulonephritis, J Immunol 2006, 177 (3):1925-1931, the contents of which are incorporated herein by reference. These methods were followed in the performance of the present example.

Mice

Age, gender, and weight-matched wild-type C57BL/6 mice were obtained from Harlan (Harlan UK Limited, Bicester, Oxon, UK). All mice used were 9 to 10 weeks of age at commencement of the experiments. Animal experiments were performed according to United Kingdom Home Office regulations. The genotype of the TLR2-deficient mice was confirmed by PCR.

Induction of Accelerated Nephrotoxic Nephritis

A mouse glomerular extract was made as described previously in Brown et al., and serum was prepared in sheep by Micropharm (Llandysul, UK). The nephrotoxic serum (NTS) was heat inactivated at 56° C. for 30 minutes and frozen in aliquots at 120° C. until use. Mice were immunized intraperitoneally with 200 1 g of normal sheep IgG that was given with 80 µl of aluminum hydroxide gel (Sigma, Poole, UK) in 310 µl of PBS, with 100 1 g of Pam3CysSK4 (EMC Microcollections, Tubingen, Germany) in 10 µl of DMSO or with 10 µl of DMSO alone. All of these components were given as a single intraperitoneal (i.p.) injection. Five days later, mice received an injection of 160 µl of NTS via the tail vein to induce disease. The dose of lipopeptide and NTS given were based on those used in other in vivo studies and on our own pilot studies. At 14 days after disease induction, mice were killed and exsanguinated for serum, and the kidneys were harvested. Any mice that showed signs of ill health before 14 days were killed humanely according to local regulations.

Histologic Analysis of Glomerular Injury

Kidney samples were fixed for 4 hours in Bouin's solution, transferred into formalin, then processed and embedded in paraffin. Sections were cut at 0.5 µm thickness and stained with periodic acid-Schiff (PAS) reagent. All samples then were assessed blindly for glomerular thrombosis by identification of the amount of PAS-positive material. In total, 50 glomeruli were assessed for each mouse for signs of glomerular thrombosis, and a score was assigned to each as follows: Grade 0, no PAS-positive material; grade 1, 25%; grade 2, 25 to 50%, grade 3, 50 to 75%, and grade 4, 75 to 100%.

The average glomerular thrombosis score for each mouse then was calculated. Sections also were assessed blindly for glomerular crescents. A total of 50 glomeruli were assessed, and the number of crescents (two or more layers of cells in Bowman's space) was expressed as a percentage.

Immunohistochemical Analysis of Glomerular Inflammation

The glomerular histology was assessed at 2 hours and 24 hours following disease induction with NTS. Kidneys were fixed in Bouin's solution and stained with periodic acid-Schiff reagent. At 2 hours, the number of neutrophils (identified by their characteristic nuclear morphology) per 50 glomerular cross sections was counted. At 24 hours, the amount of glomerular thrombosis was assessed by identification of the amount of periodic acid-Schiff-positive material. In total, 50 glomeruli were assessed for each animal for signs of glomerular thrombosis, and a score was assigned as follows: grade 0, no periodic acid-Schiff-positive material; grade 1, <25%; grade 2, 25-50%; grade 3, 50-75%; grade 4, 75-100%. All sections scored for neutrophils and glomerular thrombosis were done so blindly.

Albuminuria

Mice were housed in metabolic cages for 24 hours for urine collections. The urine albumin concentration was measured by radial immunodiffusion. The sensitivity of the radial immunodiffusion assay for albumin was 0.05 mg/ml. Urine samples were diluted to 1:40 so that values fell on the standard curve.

Female C57BL/6 mice were from Harlan. Weights were as detailed in Table 1 below:

TABLE 1

Weights were as follows

| group | wts (not correlated with specific mice) | mean |
|---|---|---|
| 1 to 5 | 16.8, 16.7, 17.5, 17.4, 17.7 | 17.22 |
| 6 to 10 | 18.1, 17.3 17.3, 17, 17.1, | 17.36 |
| 11 to 15 | 17.8, 16.9, 16.8, 17.2, 17.9 | 17.32 |
| 16 to 20 | 17, 17.4, 17.9, 16.7, 17.4, | 17.28 |
| 21 to 24 | 18.9, 17.9, 18.7, 19.9 | 18.85 |
| 26 to 30 | 18.3, 18.4, 18.7, 19.4, 18.9 | 18.78 |
| 31 to 35 | 18.9, 19.3, 17.9, 19, 19 | 18.82 |
| 36 to 40 | 19, 19.1, 18.9, 18.7, 18.3 | 18.8 |

200 ul of nephrotoxic serum containing 10 ug of the lipopetide Pam3CysSK4 (EMC microcollections) was given intravenously via the tail vein. 2 hours prior to this, mice were treated as follows.

Group 1-5 were given prednisol 30 mg/kg via the intraperitoneal (ip) route which was dissolved in pyrogen free sterile PBS at 2.73 mg/ml. Therefore 190 ul=519 ug were given to all mice based on a mean weight of 17.3 g.

Group 6-10 were given 190 µl pyrogen free sterile PBS intravenously.

Group 11-15 were given isotype control antibody 10 mg/kg intravenously. The isotype control antibody is mouse IgG1 isotype control purchased from RnD systems (catalogue number MAB002), this isotype control antibody having binding specificity for Keyhole Limpet Hemocyanin (KLH) antigen. OD was checked after reconstitution as was shown to be 0.86 mg/ml, so 200 ul was equal to 173 ug given to all mice (based on a mean weight of 17.3 g).

Group 16-20 were given the anti-TLR2 monoclonal antibody OPN301 at a dose of 10 mg/Kg intravenously 0.91 mg/ml, so 190 ul=173 ug administered to all mice (based on a mean weight of 17.3 g). OPN301 (OPN-301) is a murine IgG1 anti-TLR2 antibody (mouse Toll-like Receptor 2 (TLR2) antibody, clone T2.5, HyCult Biotechnology b.v., Cell Sciences, Canton, USA: catalogue number 1054). The above mice were bled from the tail vein for total white count and blood film, and then exsanguinated under anaesthesia.

Group 11-15 were given prednisol 30 mg/kg intraperitoneally (i.p.). Dissolved in pyrogen free sterile PBS at 2.73 mg/ml, so 207 ul=564 ug given to all mice (based on a mean weight of 18.8 g).

Group 16-20 were given 207 µl pyrogen free sterile PBS intravenously.

Group 21-24 were given isotype control antibody 10 mg/kg intravenously (RnD Systems, catalogue number MAB002). OD was checked after reconstitution=0.86 mg/ml, so 219 µl=188 µg given to all mice (based on a mean weight of 18.8 g).

Group 36-40 were given the anti-TLR2 monoclonal antibody OPN301 at 10 mg/kg intravenously. 0.91 mg/ml, so 207 ul=188 ug given to all mice (based on a mean weight of 18.8 g).

The above groups were place in metabolic cages immediately after induction of disease and exsanguinated under anaesthesia 24 hours later. Statistics were performed with GraphPad prism software. A one-way ANOVA was used with Tukey's post-test. Albuminuria and thrombosis data was analysed after a logarithmic transformation.

Results

Glomerular Neutrophils

Figure 2:
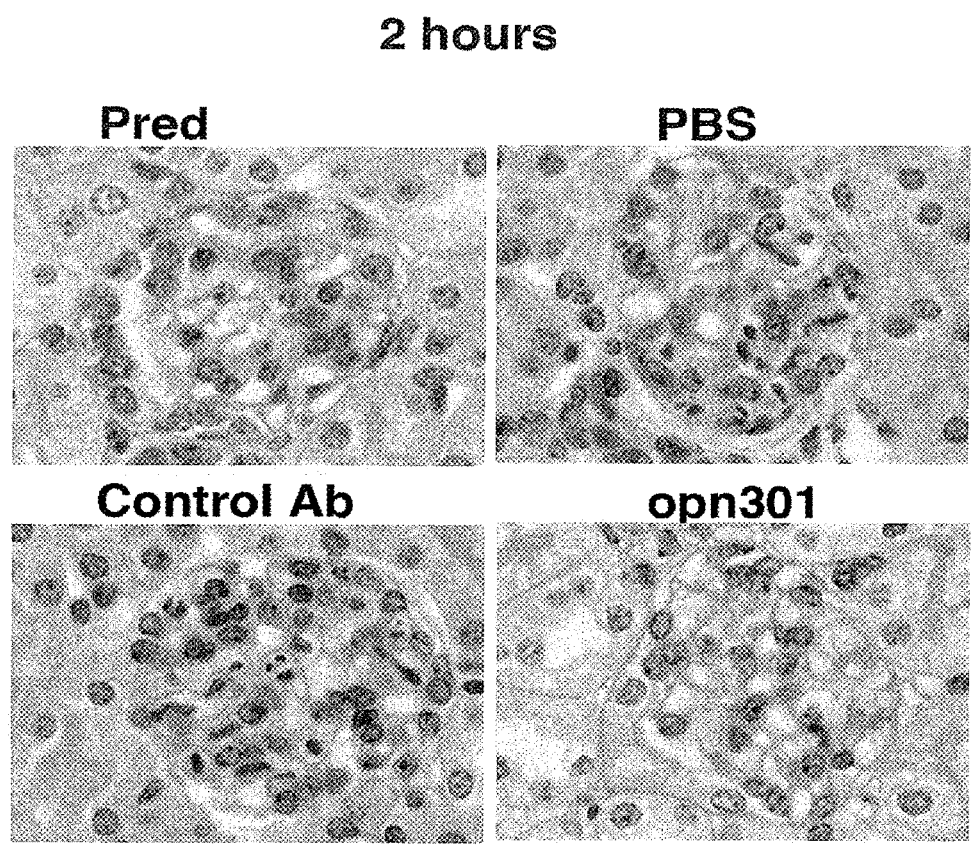
FIG. 2 shows histological sections of the kidney from C57BL/6 Toll-like Receptor 2 deficient mice treated with either 30 mg/kg intraperitoneal (i.p.) prednisol (pred), PBS control (PBS), 10 mg/kg intravenous (i.v.) isotype control antibody (Control Ab) or 10 mg/kg intravenous (i.v.) anti-TLR2 antibody OPN301 (opn301) followed by immunization with 10 ug of the lipopeptide Pam3CysSK4 for 2 hours.

There were less neutrophils in glomeruli at 2 hours in mice pretreated with the anti-TLR2 monoclonal antibody OPN301 than in PBS or control antibody treated mice (Table 1, FIG. 1). Neutrophil numbers were similar to those seen in mice pretreated with prednisolone, Representative histology at 2 hours is shown in FIG. 2.

Circulating Leukocytes

Figure 3:
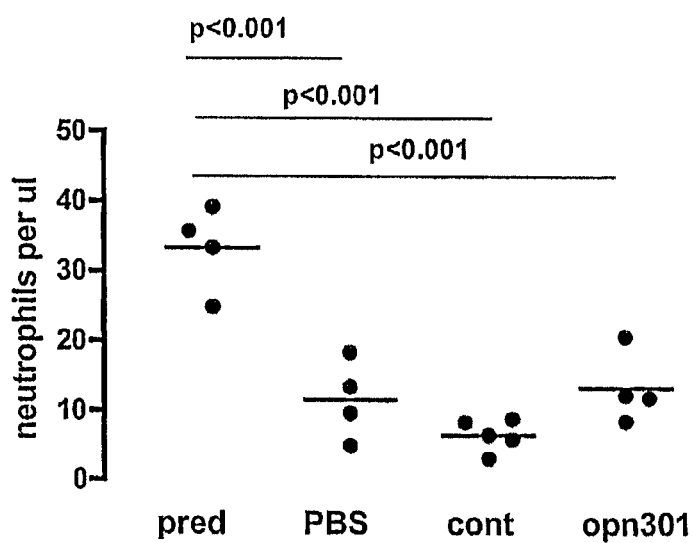
FIG. 3 shows a dot plot graph of circulating neutrophils from C57BL/6 Toll-like Receptor 2 deficient mice treated with either 30 mg/kg intraperitoneal (i.p.) prednisol (pred), PBS control (PBS), 10 mg/kg intravenous (i.v.) isotype control antibody (cont) or 10 mg/kg intravenous (i.v.) anti-TLR2 antibody OPN301 (opn301) followed by immunization with 10 ug of the lipopeptide Pam3CysSK4.
Figure 4:
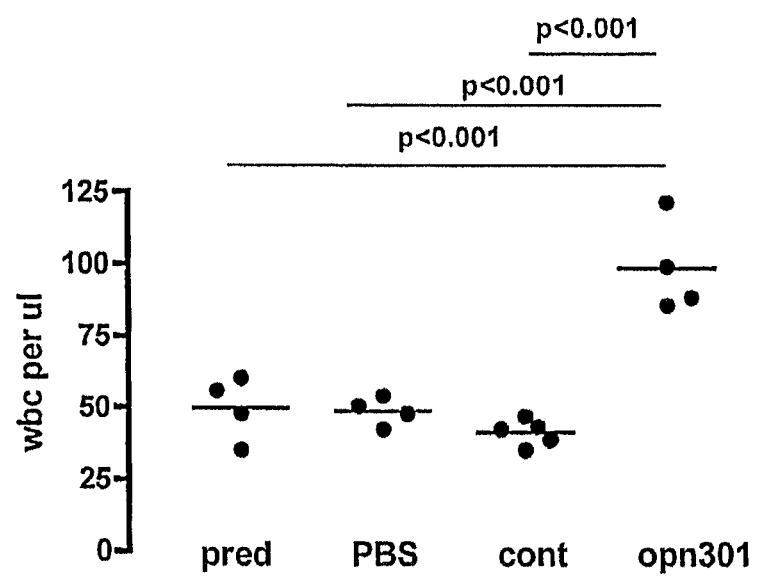
FIG. 4 shows a dot plot graph of total white blood cells from C57BL/6 Toll-like Receptor 2 deficient mice treated with either 30 mg/kg intraperitoneal (i.p.) prednisol (pred), PBS control (PBS), 10 mg/kg intravenous isotype control antibody (cont) or 10 mg/kg intravenous (i.v.) anti-TLR2 antibody OPN301 (opn301) followed by immunization with 10 ug of the lipopeptide Pam3CysSK4.

This decrease in neutrophil numbers seen in glomeruli in opn301 treated mice was not due to a decrease in circulating neutrophils since these were not lower in the anti-TLR2 monoclonal antibody OPN301 treated mice than PBS or isotype control antibody treated groups (Table 2, FIG. 3). In fact there was a trend towards more neutrophils in the anti-TLR2 monoclonal antibody OPN301 treated mice, which would have reached significance if at test was used to compare the anti-TLR2 monoclonal antibody OPN301 and the isotype control antibody treated mice (p=0.03). The circulating neutrophil numbers in steroid treated mice were much higher than in other groups, though this did not lead to a significant increase in glomerular number. The total blood leukocytes were higher in the anti-TLR2 monoclonal antibody OPN301 treated mice than in any other group (Table 2, FIG. 4).

TABLE 2

Circulating neutrophil numbers in treated mice

| Mouse | cells/ul | % pmn | pmn/ul | pmn/glom |
|---|---|---|---|---|
| Prednisone | | | | |
| 1 | 47.7 | 70 | 33.4 | 0.28 |
| 2 | 55.8 | 64 | 35.7 | 0.42 |
| 3 | | 49 | | 0.24 |
| 4 | 60.3 | 65 | 39.2 | 0.34 |
| 5 | 35.1 | 71 | 24.9 | 0.54 |
| PBS | | | | |
| 6 | | 12 | | 3 |
| 7 | 47.7 | 28 | 13.4 | 2.8 |
| 8 | 54 | 34 | 18.4 | 3.36 |
| 9 | 42.3 | 23 | 9.7 | 3.02 |
| 10 | 50.4 | 10 | 5.0 | 2.96 |

TABLE 2-continued

Circulating neutrophil numbers in treated mice

| Mouse | cells/ul | % pmn | pmn/ul | pmn/glom |
|---|---|---|---|---|
| Isotype Control Antibody | | | | |
| 11 | 42.3 | 21 | 8.9 | 2.7 |
| 12 | 38.7 | 17 | 6.6 | 2.94 |
| 13 | 35.1 | 9 | 3.2 | 2.8 |
| 14 | 46.8 | 18 | 8.4 | 3.28 |
| 15 | 43.2 | 14 | 6.0 | 2.58 |
| OPN301 Antibody | | | | |
| 16 | 121.5 | 17 | 20.7 | 0.14 |
| 17 | 99 | 12 | 11.9 | 0.12 |
| 18 | | 21 | | 0.32 |
| 19 | 88.2 | 14 | 12.3 | 0.24 |
| 20 | 85.5 | 10 | 8.6 | 0.2 |

Albuminuria and Glomerular Thrombosis

Figure 5:
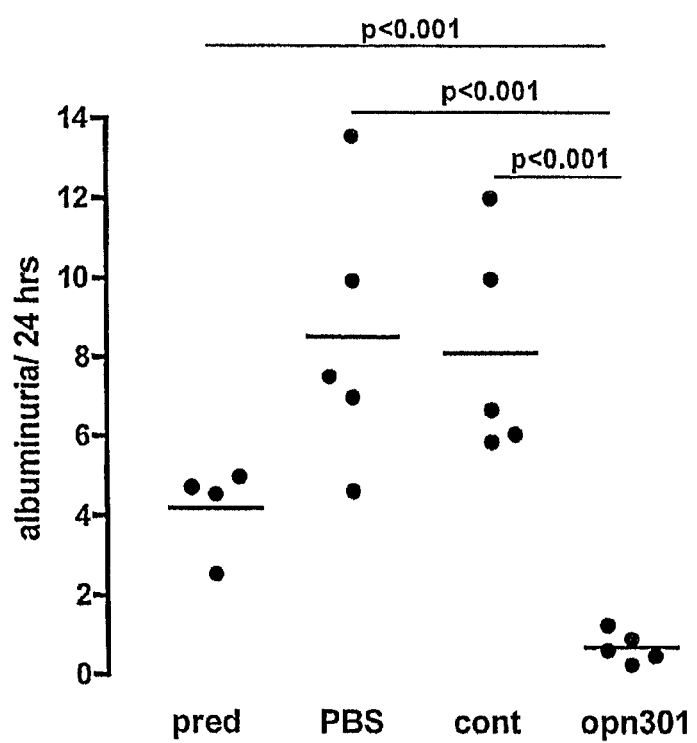
FIG. 5 shows a dot plot graph of albuminuria/24 hours from C57BL/6 Toll-like Receptor 2 deficient mice treated with either 30 mg/kg intraperitoneal (i.p.) prednisol (pred), PBS control (PBS), 10 mg/kg intravenpus (i.v) isotype control antibody (cont) or 10 mg/kg intravenous (i.v.) anti-TLR2 antibody OPN301 (opn301) followed by immunization with bug of the lipopeptide Pam3CysSK4.
Figure 6:
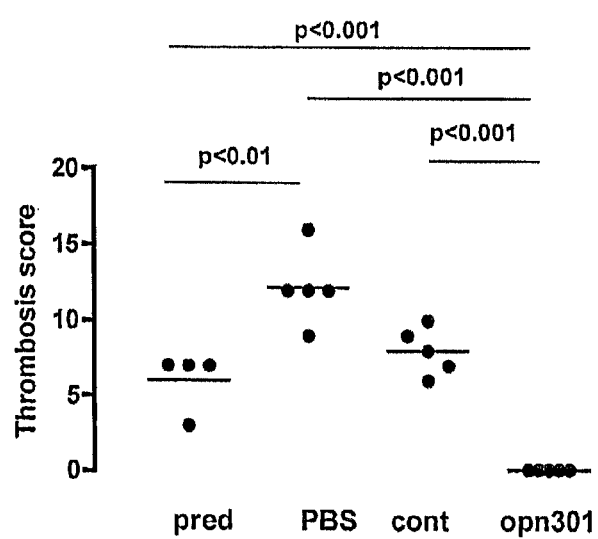
FIG. 6 shows a dot plot graph of thrombosis score from C57BL/6
Figure 7:
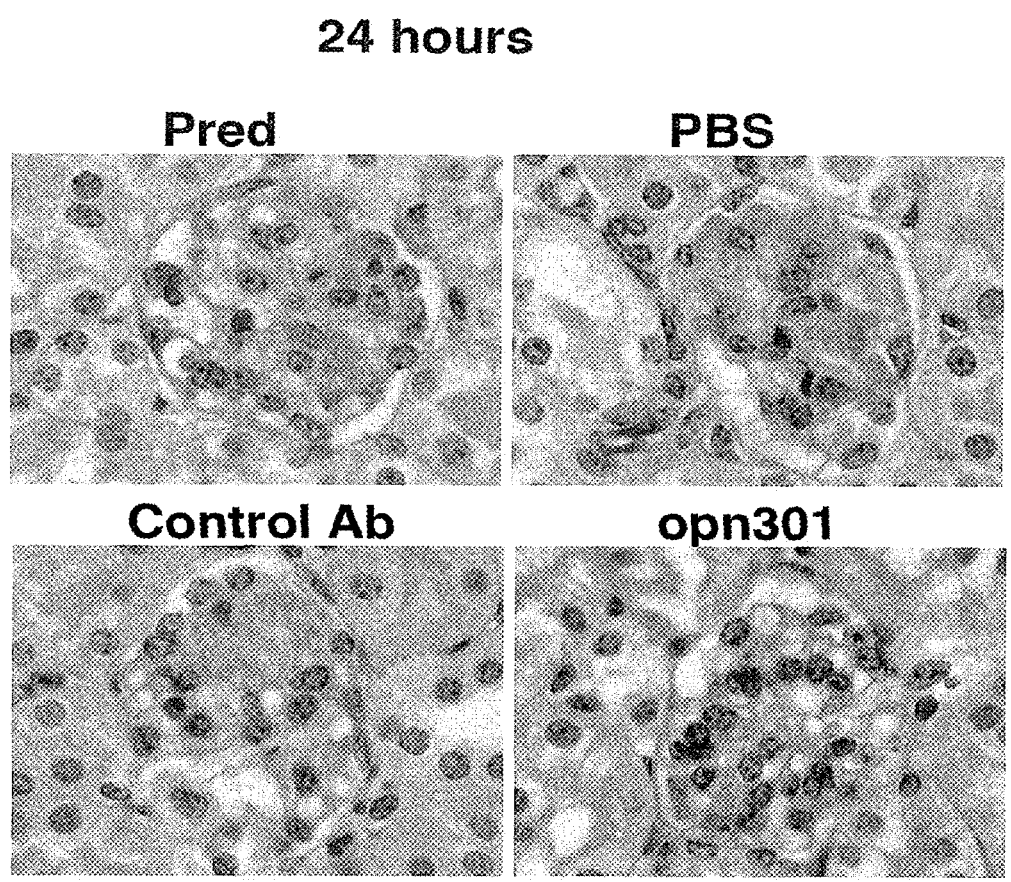
FIG. 7 shows histological sections of the kidney from C57BL/6 Toll-like Receptor 2 deficient mice treated with either 30 mg/kg intraperitoneal (i.p.) prednisol (Pred), PBS control (PBS), 10 mg/kg intravenous (i.v.) isotype control antibody (Control Ab) or 10 mg/kg intravenous (i.v.) anti-TLR2 antibody OPN301 (opn301) followed by immunization with bug of the lipopeptide Pam3CysSK4 at 24 hours.

There was less glomerular albuminuria and thrombosis in the anti-TLR2 monoclonal antibody OPN301 treated mice than in PBS, isotype control antibody or steroid treated mice (Table 3 and FIGS. 5 and 6). The reduction in albuminuria due to steroids did not reach significance when compared with PBS or control antibody treated mice. Steroid treated mice had significantly less thrombosis than PBS but not control antibody treated mice. It should be noted that glomerular thrombosis is not marked in this model, as the numbers shown are the numbers of glomeruli showing any thrombosis out of a total of 50. Representative histology at 24 hours is shown in FIG. 7.

TABLE 3

Glomerular albuminura and thrombosis in treated mice

| | Thromb/50 gloms | alb, mg/ml |
|---|---|---|
| Prednisone | | |
| 21 | 7 | 2.54 |
| 22 | 7 | 4.54 |
| 23 | 7 | 4.71 |
| 24 | 3 | 4.98 |
| PBS | | |
| 26 | 12 | 4.62 |
| 27 | 12 | 9.95 |
| 28 | 12 | 7 |
| 29 | 16 | 13.56 |
| 30 | 9 | 7.52 |
| OPN301 Antibody | | |
| 31 | 0 | 0.92 |
| 32 | 0 | 0.5 |
| 33 | 0 | 1.26 |
| 34 | 0 | 0.63 |
| 35 | 0 | 0.27 |
| Isotype Control Antibody | | |
| 36 | 8 | 12.02 |
| 37 | 7 | 9.99 |
| 38 | 9 | 5.86 |
| 39 | 6 | 6.68 |
| 40 | 10 | 6.06 |

Conclusions

The anti-TLR2 monoclonal antibody OPN301 caused a decrease in glomerular inflammation that was equivalent to high-dose steroids. The effect on albuminuria and thrombosis was greater than that seen with steroids.

Example 2

Renal Ischemia

All experiments reported were conducted as stated in the National Institutes of Health Guide For The Care And Use Of Laboratory Animals (Institute of Laboratory Animal Resources, National Academy Press, Washington D.C., 1996) and were approved by a local animal care and use committee, and in accordance with a currently valid license for experiments on vertebrate animals, issued by the French Ministry for Agriculture and Fisheries to Dr Yara Barreira (N° 125 dated 8 Jun. 2002, validity=5 years).

Nine Experimental groups were used as follows:
1) Sham-operated mice sacrificed 1 day after surgery, n=6,
2) PBS-vehicle-treated mice 15 min before ischemia/1 day reperfusion, n=6,
3) Isotype control antibody 10 mg/kg-treated mice 15 minutes before ischemia/1 day reperfusion, n=6 (The isotype control antibody is mouse IgG1 isotype control purchased from RnD systems (catalogue number MAB002), this isotype control antibody having binding specificity for Keyhole Limpet Hemocyanin (KLH) antigen),
4) OPN301 anti-TLR2 monoclonal antibody 10 mg/kg-treated mice 15 minutes before ischemia/1 day reperfusion, n=6,
5) Pargyline 6 mg/kg-treated mice 15 minutes before ischemia/1 day reperfusion, n=6,
6) PBS-vehicle-treated mice 15 minutes before ischemia/5 days reperfusion, n=6,
7) Isotype control antibody (RnD systems catalogue number MAB002) 10 mg/kg-treated mice 15 minutes before ischemia/5 days reperfusion, n=6,
8) OPN301 anti-TLR2 antibody 10 mg/kg-treated mice 15 minutes before ischemia/5 days reperfusion, n=6,
9) Pargyline 6 mg/kg-treated mice 15 minutes before ischemia/5 days reperfusion, n=6.

Experimental Warm Renal Ischemia/Reperfusion

Warm renal ischemia/reperfusion (I/R) experiments were adapted from a previous study (Stokman et al, 2005). Briefly, a wild type strain of C57BL/6 mice were anesthetized with 10 µl/g of a mix of 2.5 ml ketamine (Ketalar 50 mg/ml, Centravet; Lapalisse, France), 0.5 ml xylazine (Rompun 2.5%, Centravet; Lapalisse, France), and 7 ml NaCl 0.9% (Centravet; Lapalisse, France). During surgery, animals were set on a 35° C. hotplate. After a 2 millimeters incision, the jugular vein was exposed for intravenous injection (insulin syringe; VWR, Fontenay-sous-Bois, France) of 300 µl (1 min infusion) of the considered treatment. The incision was closed after haemostasis (5/0 Ethicrin thread, Ethicon; Auneau, France). Three centimetre in length abdominal cutaneous and muscular incisions were performed; renal pedicles were exposed and clamped for 30 minutes using microaneurysm clamps (AREX; Palaiseau, France). At the time of clamp installation and removal, kidneys were inspected for blood flow arrest and restoration, respectively. Throughout renal ischemia duration, the abdomen was wrapped up to avoid loss of heat and to keep a relative intra-abdominal pressure. At the time of abdomen closing in 2 layers (5/0 Ethicrin thread, Ethicon; Auneau, France), mice were supplemented with 1 ml sterile NaCl 0.9% to maintain fluid balance and volume status. Finally, all mice received an intramuscular injection of 10 mg/kg profenid 50 mg/ml (Centravet; Lapalisse, France) for analgesic purpose then allowed to recover from surgery for 12 hours at 32° C. in a ventilated stove. Food and water were given ad libitum. Sham-operated mice underwent the same procedure without clamping.

At the end of the experiment, mice were sacrificed by lethal injection of pentobarbital (100 µl/10 g, Ceva Sante Animate; Libourne, France) 1 and 5 days after surgery. Blood samples were collected by abdominal aortic puncture, transferred into tubes for coagulation (30 minutes, 4° C.) then centrifuged (10 minutes, 1200 rpm, 4° C.) for plasma collection and stored at −80° C. until use for renal function measurement. Kidneys were removed and divided for preparation of histology (one-half kidney transferred in Carnoy's solution—absolute ethanol 60%: chloroform 30%: icy acetic acid 1%), for biochemical analyses (2 one-half kidneys snap-frozen in liquid nitrogen then stored at −80° C. until use for MPO and MDA evaluations), and cytokine/chemokine measurements (one-half kidney snap-frozen in liquid nitrogen then stored at −80° C. until sending to the Sponsor by CryoExpress shipment).

All the following analyses were made blindly.

Renal Function

The renal function determination was based on the evaluation of plasmatic creatinine and urea concentrations on a Cobas Mira biochemical analyzer (Horiba ABX; Montpellier, France), according to standard diagnostic procedures followed by the Rangueil hospital research services. Results were expressed as mmol/l for urea and µmol/L for creatinine.

Histology for Ischemia/Reperfusion Injury Estimation

After the 24 hour-fixation in Carnoy's solution, the one-half kidneys were embedded in paraffin according to standard procedures. Longitudinal 3-4-µm-thick histological sections were performed and stained with PAS. Briefly, sections were deparaffinized and rehydrated to water, then oxidized in 0.5% periodic acid solution for 10 minutes (DAKO; Trappes, France). After rinsing, Schiff's reagent (DAKO; Trappes, France) was added for 10 minutes then washed in lukewarm tap water for 5 minutes to stop reduction of Schiff base. Counterstaining was proceeded in Mayer's hematoxylin solution (DAKO; Trappes, France) for 2 minutes, washed in tap water for 5 minutes, then rapidly dehydrated and mounted.

Damaged tubules were assessed by semi-quantitative scoring of the percentage of affected tubules per 10 non-overlapping fields (×400 magnitude) in the cortico-medullary region. The injury criteria such as tubular dilatation, epithelial necrosis, cast deposition, and loss of brush border were followed and graded on a 5-point scale: 0 for 0% injury, 1 for <10% injury, 2 for 10 to 25% injury, 3 for 25 to 50% injury, 4 for 50 to 75% injury, and 5 for >75% injury.

Immunohistology for Macrophage Infiltration

Longitudinal sections were also used for F4/80 immunodetection. Briefly, deparaffinized sections were incubated for 10 minutes with 3% hydrogen peroxide to block the endogenous peroxidase activity. After the non-specific antigenic sites were saturated, sections were sequentially incubated at room temperature in a humidified atmosphere with: (i) the rat monoclonal antibody to mouse F4/80 (1/400e—Caltag Laboratories, Invitrogen; Cergy Pontoise, France) for 15 minutes, (ii) the rabbit polyclonal antibody to rat IgG (1/800e—DAKO; Trappes, France) for 15 minutes; and then (iii) the labeled HRP anti-rabbit Envision System (DAKO; Trappes, France) for 20 minutes.

Specific antigenic sites were revealed with DAB (DAKO; Trappes, France). Sections were counterstained with Mayer's hematoxylin solution (DAKO; Trappes, France). Negative controls for the immunohistochemical procedure included use of the control isotype of primary antibody F4/80 (IgG2a, 1/400e—Caltag Laboratories, Invitrogen; Cergy Pontoise, France). Analysis was performed by an operator unaware of the origin of each kidney section and removal of the histological codes was performed at the end of recordings. Quantifications of the selected objects within a given image were recorded into a Microsoft Excel file combined to the ExploraNova software. Results were given in percentage (%) of specific coloured area per total studied area of the 10 non-overlapping fields (×200 magnitude), representing thus the surface occupied by the analyzed marker in the cortico-medullary junction.

Malondialdehyde production evaluation as an index of oxidative stress

Snap-frozen one-half kidneys were first homogenized in a mix of PBS and PMSF 2 mM (Sigma Aldrich; St Quentin Fallavier, France), then MDA concentration was indirectly determined by quantifying the production of a specific chromogen compound from the reaction between MDA and 2 molecules of thiobarbituric acid, as previously described (Aruoma et al, 1989).

Briefly, homogenate aliquot was mixed with trichloracetic acid 5% (Sigma Aldrich; St Quentin Fallavier, France) and centrifuged (20 minutes, 4000 rpm, 4° C.). The supernatant was added to thiobarbituric acid 78 mM (Sigma Aldrich; St Quentin Fallavier, France) and HCl 0.02M then heated for 10 minutes at 95° C. The chromogen compound produced was then spectrophotometrically measured at 535 nM wavelength (Helios β Unicam, Thermo Fisher Scientific; Courtaboeuf, France). MDA bismethyl acetal (Sigma Aldrich; St Quentin Fallavier, France) was used as an external standard. Results were expressed as nmol MDA/mg proteins.

Myeloperoxidase Activity for Neutrophil Accumulation

Snap-frozen one-half kidneys were also homogenized in a mix of potassium phosphate buffer 5 mM, pelleted (20,000 g, 45 minutes, 4° C.) and put suspended in a mix of phosphate buffer 50 mM and hexadecyltrimethyl ammonium bromide 0.5% (Fluka, Sigma Aldrich; St Quentin Fallavier, France). A last centrifugation (20,000 g, 45 minutes, 4° C.) finalized MPO release in the supernatant that was kept for the enzyme activity measurement.

Briefly, MPO activity was indirectly determined by using o-dianisidine dihydrochloride 0.167 mg/mL (Acros Organics; Noisy le Grand, France) and hydrogen peroxide 0.1 mM in phosphate buffer 50 mM/pH 6. The absorbance of the product was spectrophotometrically determined at 460 nm wavelength (Helios β Unicam, Thermo Fisher Scientific; Courtaboeuf, France). Results were expressed as U MPO/mg proteins after normalization to protein content.

Analysis and Expression of Results

The results were given as mean values±standard error of the mean (SEM). A one-way ANOVA was used for comparison of within-group difference followed by a Newman-Keuls test for comparison of all pairs of columns. p<0.05 was considered statistically significant.

Results

Effects of Warm Renal Ischemia/Reperfusion

Figure 8A:
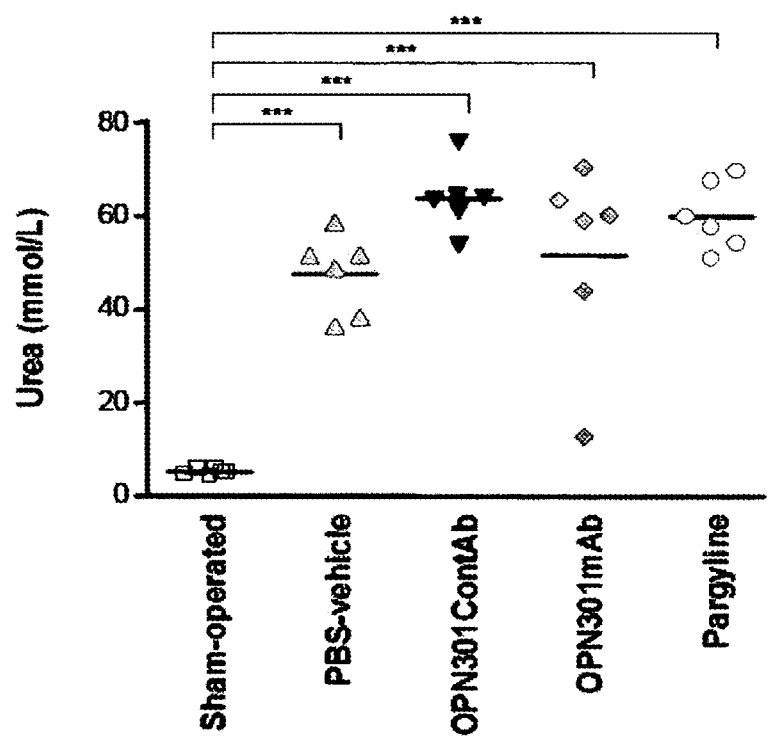
FIG. 8 shows dot plot graphs of measurements of urea (mmol/L) (A) and creatinine (mmol/L) (B) in mice kidneys from treatment groups (i) Sham-operated, (ii) PBS-vehicle, (iii) 10 mg/kg isotype control antibody (Control Ab), (iv) 10 mg/kg anti-TLR2 OPN301 monoclonal antibody, and (v) 6 mg/kg pargyline, measured 1 and 5 days after renal ischemia/reperfusion (n=6 per group)

The functional impact of I/R was assessed by the measurement of key plasmatic parameters such as urea (FIG. 8A) and creatinine (FIG. 8B). One day after I/R, creatininemia and uremia were greatly increased as compared to sham-operated group, indicating a renal function impairment (47.54±3.49 mmol/L urea and 371.83±27.34 µmol/L creatinine vs. 5.21±0.32 mmol/L urea and 43.02±12.01 µmol/L creatinine in PBS-vehicle and sham-operated groups, respectively; n=6 per group, ***p<0.01, ANOVA with Newman-Keuls test).

Figure 9A:
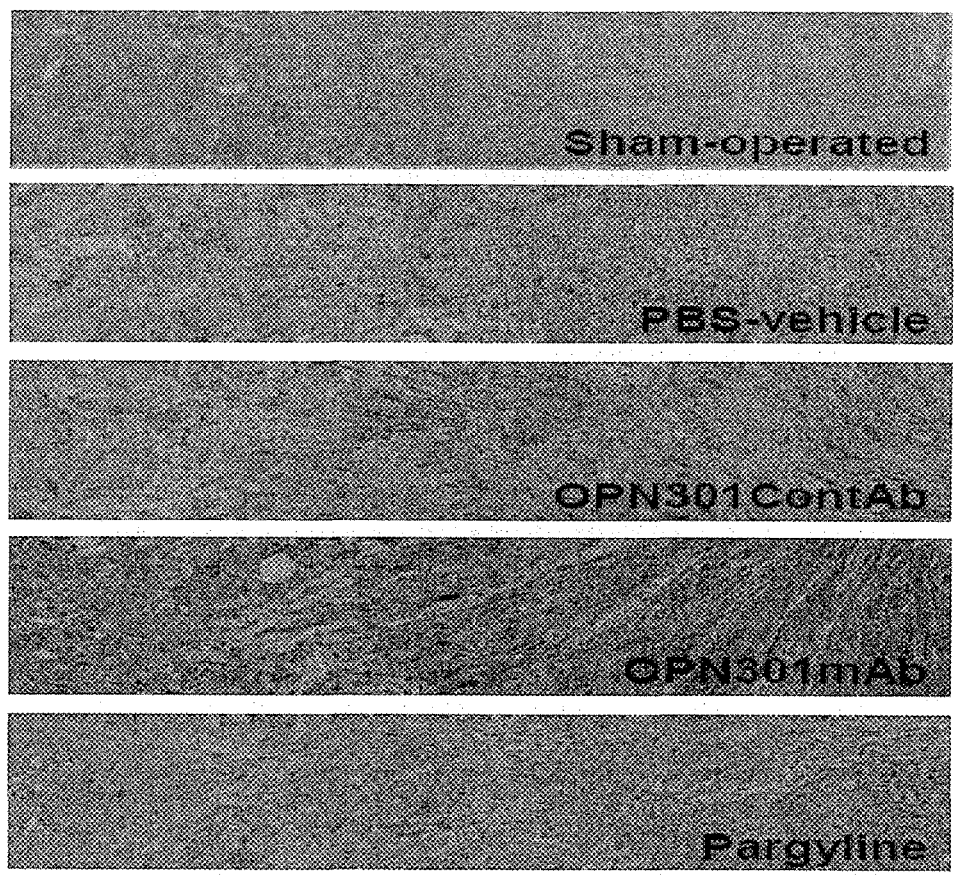
FIG. 9 shows (A) representative histological kidney sections showing tubular injury and (b) a dot plot graph of semi quantitative scoring of the percentage of damage tubules of mice from treatment groups (i) Sham-operated, (ii) PBS-vehicle, (iii) 10 mg/kg isotype control antibody (Control Ab), (iv) 10 mg/kg anti-TLR2 OPN301 monoclonal antibody, and (v) 6 mg/kg pargyline measured 1 day after renal ischaemia/repefusion (n=6)
Figure 9B:
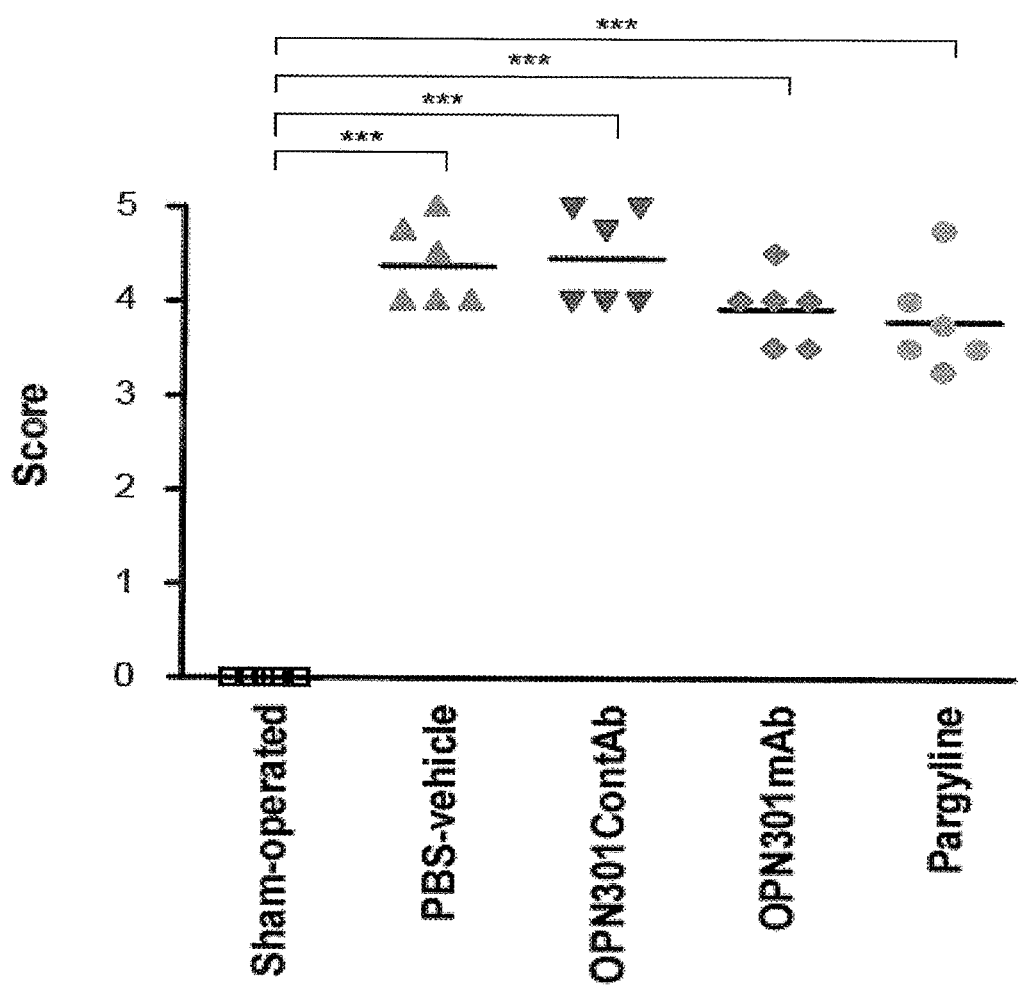

The loss of function was correlated to structural findings as assessed by the percentage of damaged tubules (FIG. 9(B)). One day after bilateral I/R, the degree of tubular injury in kidney sections was severe and spread to the whole cortico-papillar gradient, and not only to the outer medulla (FIG. 9A); (n=6 per group, ***p<0.01, ANOVA with Newman-Keuls test).

As one of the key features of I/R injury is acute inflammation associated with phagocytes infiltration (macrophages and neutrophils), F4/80 immunostaining (FIG. 10(A)) and MPO activity (FIG. 10(B)) quantifications were performed. One day after I/R, the increases in macrophage infiltration as well as MPO activity in renal tissue were correlated to the ischemic injury time course (3.24±0.21% F4/80-positive staining and 63.2±9.55 U MPO/mg protein vs. 0.91±0.13% F4/80-positive staining and 20.72±1.18 U MPO/mg protein in PBS-vehicle and sham-operated groups, respectively; ***p<0.01 compared to Sham-operated group, # p<0.05, ## p<0.01 and ### p<0.001 compared to PBS-vehicle group, §§§p<0.001 compared to OPN301ContAb, p<0.05 compared to OPN301 monoclonal antibody; n=6 per group, ANOVA with Newman-Keuls test.

MDA production used as an index of oxidative stress injury, was not significantly modified one day after I/R as compared to basal value (0.082±0.004 nmol MDA/mg protein vs. 0.080±0.005 nmol/mg protein in PBS-vehicle and sham-operated groups, respectively (FIG. 11); ***p<0.01 compared to Sham-operated group, # p<0.05 and ### p<0.001 compared to PBS-vehicle group, §p<0.001 compared to OPN301ContAb; n=6 per group, ANOVA with Newman-Keuls test.

The second endpoint, 5 days after renal I/R, was not assessed since mice mortality was about 80% at day 2 and 100% at day 4. Considering the functional values, it was concluded that the renal damage after 30-minute ischemia was too extended to allow the mice survival and the recovery of renal function. The histological analysis confirmed this hypothesis since the whole cortico-papillar gradient was destroyed by consequences of I/R injury.

Figure 8:
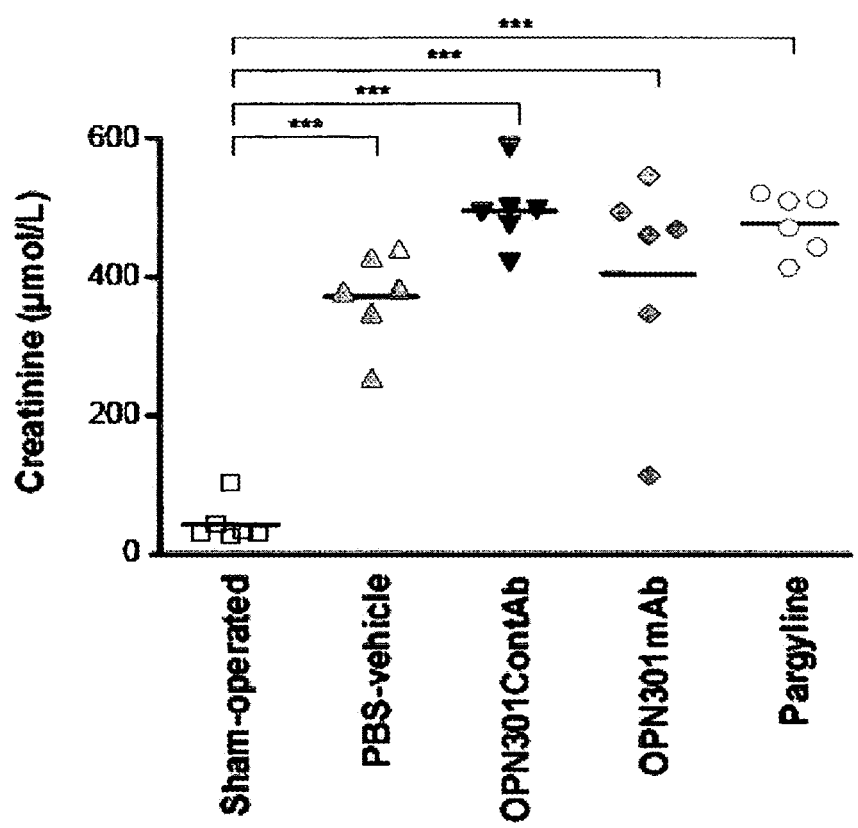

Effects of OPN301 anti-TLR2 Monoclonal Antibody and Pargyline on Acute Renal Failure One Day After Ischemia/Reperfusion When the effects of OPN301 anti-TLR2 monoclonal antibody were analyzed one day after I/R, the main obstacle encountered was the severity of damages induced, and thus, the stringency of the model. Indeed, from a functional and histological point of view, we could not be able to discriminate between experimental groups (FIGS. 8 and 9).

However, some parameters gave some encouraging suggestions such as those related to inflammation i.e. macrophage infiltration and neutrophil accumulation in renal tissue. Considering macrophage infiltration (FIG. 10(A)), immunohistochemical analysis of kidney sections demonstrated a decrease in F4/80 positive staining when compared with PBS-vehicle group (1.38±0.11% vs. 3.24±0.21% in OPN301 mAb and PBS-vehicle groups, respectively, n=6, p<0.001, ANOVA with Newman-Keuls test). Considering neutrophil accumulation (FIG. 10(B)), MPO activity levels demonstrated a decrease in enzyme activity when compared with PBS-vehicle group (27.32±1.95 U MPO/mg protein vs. 63.2±9.55 U MPO/mg protein in OPN301 mAb and PBS-vehicle groups, respectively, n=6, p<0.01, ANOVA with Newman-Keuls test).

Figure 10:
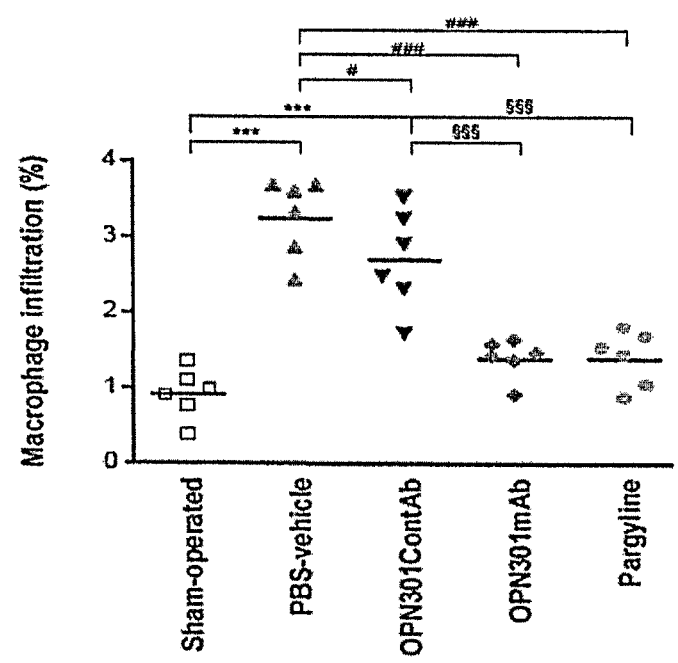
FIG. 10 shows (A) dot plot graphs of percentage of macrophage infiltration and (B) accumulation of myeloperoxidase (MPO) (U/mg proteins) in mice kidney from treatment groups (i) Sham-operated, (ii) PBS-vehicle, (iii) 10 mg/kg isotype control antibody (Control Ab), (iv) 10 mg/kg anti-TLR2OPN301 monoclonal antibody, and (v) 6 mg/kg pargyline measured 1 day after renal ischaemia/reperfusion (n=6 per group)
Figure 10:
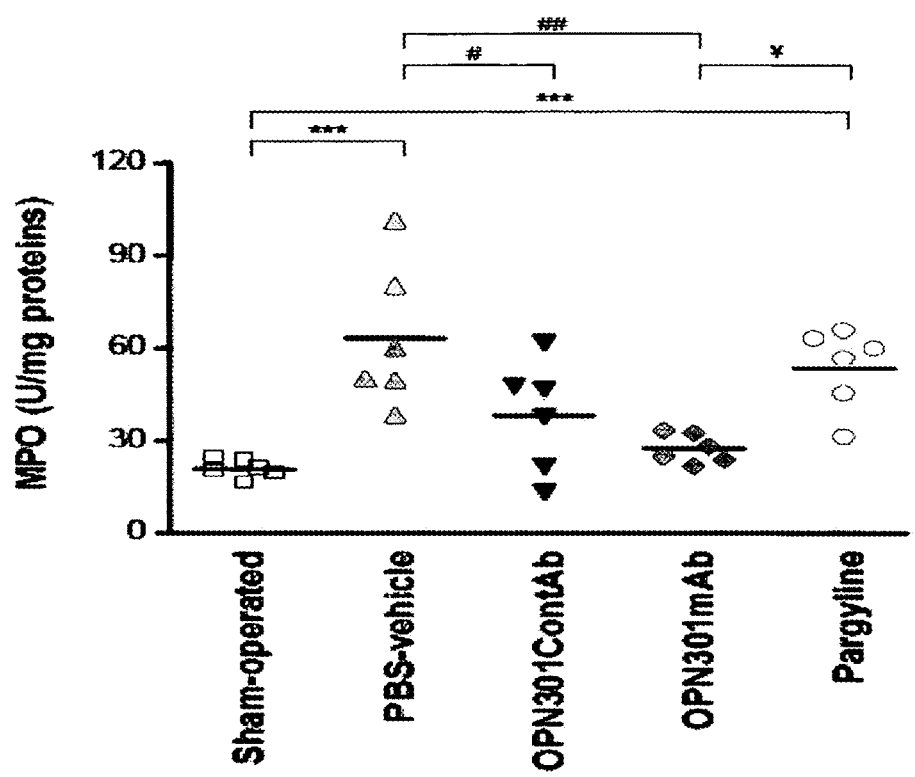

It was noteworthy that the isotype control antibody seemed to possess intrinsic properties since it was able to decrease macrophage infiltration (2.69±0.27% vs. 3.24±0.21% F4/80-positive staining in the isotype control antibody and PBS-vehicle groups, respectively, n=6, p<0.05, ANOVA with Newman-Keuls test; FIG. 10(3A)) as well as neutrophil accumulation in renal tissue (38.1±7.34 U MPO/mg protein and 63.2±9.55 U MPO/mg protein in the isotype control antibody and PBS-vehicle groups, respectively; n=6, p<0.05, ANOVA with Newman-Keuls test; FIG. 10(3B)). Whereas its activity was significantly distinct from OPN301 mAb on the decrease in macrophage infiltration (2.69±0.27% vs. 1.38±0.11% F4/80-positive staining in the isotype control antibody and OPN301 anti-TLR2 monoclonal antibody groups, respectively; n=6, p<0.0001, ANOVA with Newman-Keuls test), its effect was not significantly different from the experimental antibody on MPO activity (38.1±7.34 U MPO/mg protein vs. 27.32±1.95 U MPO/mg protein in the isotype control antibody and OPN301 anti-TLR2 monoclonal antibody groups, respectively; n=6, p<0.0001, ANOVA with Newman-Keuls test).

The reference substance treatment (pargyline) had no effect on neutrophil accumulation in renal tissue (53.48±5.34 U MPO/mg protein versus 63.20±9.55 U MPO/mg protein in pargyline and PBS-vehicle groups, respectively; n=6; FIG. 10(3B)). Its action on macrophage infiltration was similar to the experimental mAb (1.39±0.15% and 1.38±0.11% F4/80-positive staining in pargyline and OPN301 anti-TLR2 monoclonal antibody groups, respectively, n=6; FIG. 10(3A)).

Figure 11:
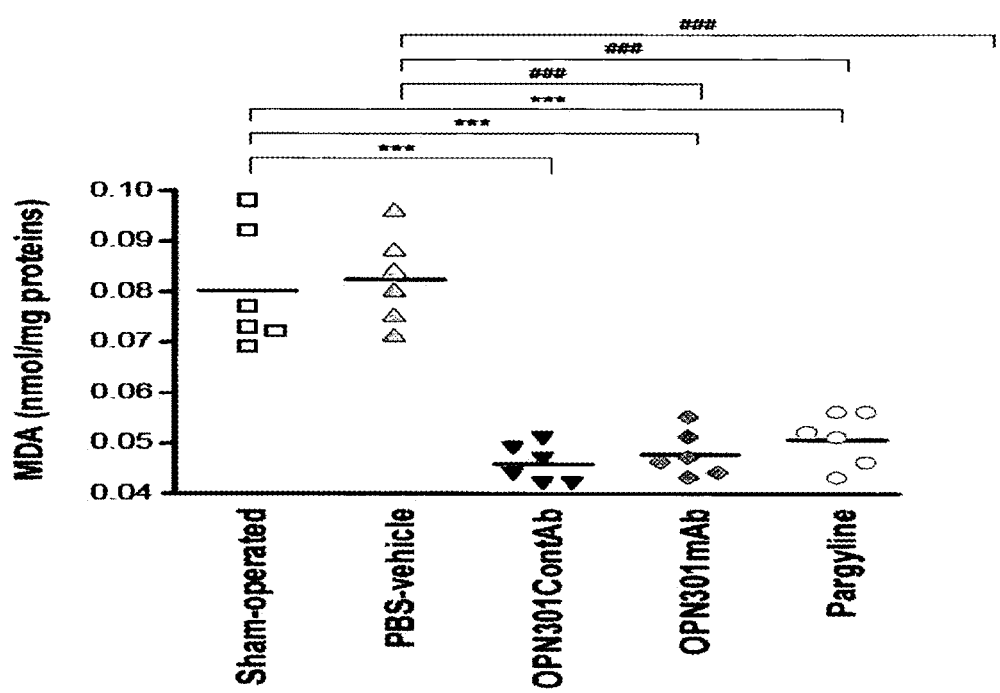
FIG. 11 shows a dot plot graph indicating malondialdehyde (MDA) production (nmol/mg proteins) used as an index of lipid peroxidation in mice kidney 1 day after renal ischaemia/reperfusion in the following treatment groups: (i) Sham-operated, (ii) PBS-vehicle, (iii) 10 mg/kg isotype control antibody (Control Ab), and (iv) 10 mg/kg anti-TLR2 OPN301 monoclonal antibody and (v) 6 mg/kg pargyline measured 1 day after renal ischaemia/reperfusion. (n=6 per group)

Considering lipid peroxidation, the administration of OPN301 anti-TLR2 monoclonal antibody produced a significant reduction in basal MDA level (0.048±0.002 nmol/mg proteins vs. 0.082±0.004 nmol/mg proteins in OPN301 anti-TLR2 monoclonal antibody and PBS-vehicle groups, respectively; n=6, p<0.001, ANOVA with Newman-Keuls test; FIG. 11). However, once again, it had to be taken into account that the isotype control antibody had the same effect on MDA level (0.046±0.002 nmol/mg proteins vs. 0.082±0.004 nmol/mg proteins in the isotype control antibody and PBS-vehicle groups, respectively; n=6, p<0.001, ANOVA with Newman-Keuls test; FIG. 11).

Regarding the reference substance treatment with pargyline, it led to an expected decrease in the oxidative stress induced by ischemia/reperfusion, as demonstrated by the MDA level (0.051±0.002 nmol/mg proteins vs. 0.082±0.004 nmol/mg proteins in pargyline and PBS-vehicle groups, respectively; n=6, p<0.001, ANOVA with Newman-Keuls test; FIG. 11).

Conclusions

Example 2 shows that renal warm ischemia/reperfusion (I/R) induced a huge loss of renal function characterized by increases in the creatininemia and uremia that could be directly correlated with marked damages along the whole cortico-papillar gradient mainly characterized by tubular necrosis. The only criticism of this model was its severity that did not allow discrimination of treatment efficacies from a functional or structural point of view. Indeed, as ischemic lesions of the initial acute renal failure were not reversible, the tubular cell loss was not compensated and ischemic acute renal failure quickly evolved towards terminal renal failure and animal death. However, some biochemical markers used as index of macrophage infiltration, neutrophil accumulation, and lipid peroxidation represented convincing arguments in favour of the usefulness of OPN301 anti-TLR2 monoclonal antibody treatment in ischemic renal injury. Indeed, a beneficial effect of OPN301 anti-TLR2 monoclonal antibody was demonstrated on these parameters, despite significant intrinsic properties of control antibody, notably on MPO activity and MDA level.

Example 3

Renal Ischemia Repeat Study

Five experimental groups were used in Step 1 as follows:
1) Sham-operated mice sacrificed 1 day after surgery,
2) 20 minutes of ischemia/1 day reperfusion, n=4,
3) 20 minutes of ischemia/5 day reperfusion, n=4,
4) 25 minutes of ischemia/1 day reperfusion, n=4,
5) 25 minutes of ischemia/1 day reperfusion, n=4.

Nine Experimental groups were used in Step 2:
1) Sham-operated mice sacrificed 1 day after surgery, n=6,
2) PBS-vehicle-treated mice 15 minutes before ischemia/1 day reperfusion, n=6,
3) Isotype control antibody 10 mg/kg-treated mice 15 minutes before 25 minutes ischemia/1 day reperfusion, n=6 (The isotype control antibody is mouse IgG1 isotype control purchased from RnD systems (catalogue number MAB002), this isotype control antibody having binding specificity for Keyhole Limpet Hemocyanin (KLH) antigen),
4) OPN301 anti-TLR2 monoclonal antibody 10 mg/kg-treated mice 15 minutes before 25 minutes ischemia/1 day reperfusion, n=6,
5) Pargyline 6 mg/kg-treated mice 15 minutes before 25 minutes ischemia/1 day reperfusion, n=6,
6) PBS-vehicle-treated mice 15 minutes before 25 min ischemia/5 day reperfusion, n=6,
7) Isotype control antibody (RnD Systems catalogue Number MAB002) 10 mg/kg-treated mice 15 minutes before 25 minutes ischemia/5 day reperfusion, n=6,
8) OPN301 anti-TLR2 monoclonal antibody 10 mg/kg-treated mice 15 minutes before 25 minutes ischemia/5 day reperfusion, n=6,
9) Pargyline 6 mg/kg-treated mice 15 minutes before 25 minutes ischemia/5 day reperfusion, n=6, Experimental Warm Renal Ischemia/Reperfusion (Step 1 and 2)

Briefly, mice were anesthetized with 10 µl/g of a mix of 2.5 ml ketamine (Ketalar 50 mg/mL, Centravet; Lapalisse, France), 0.5 ml xylazine (Rompun 2.5%, Centravet; Lapalisse, France), and 7 mL NaCl 0.9% (Centravet; Lapalisse, France). During surgery, animals were set on a 35° C. hotplate.

After a 2 millimetre incision was made at the right jugular level, jugular vein was exposed for a 1 minute-intravenous injection (insulin syringe; VWR, Fontenay-sous-Bois, France) of 70 µl of the considered treatment then closed after haemostasis (5/0 Ethicrin thread, Ethicon; Auneau, France). In Step 1, no jugular injection was performed.

Three centimetre midline incisions were made to abdominal cutaneous followed by muscular incisions were performed; renal pedicles were exposed and clamped for 25 minutes using microaneurysm clamps (AREX; Palaiseau, France). At the time of clamp installation and removal, kidneys were inspected for blood flow arrest and restoration, respectively. During renal ischemia duration, the abdomen was wrapped up to avoid loss of heat and be kept in relative intra-abdominal pressure. At the time of abdomen closing in 2 layers (5/0 Ethicrin thread, Ethicon; Auneau, France), mice were supplemented with 1 mL sterile NaCl (sodium chloride) 0.9% to maintain fluid balance and volume status. Finally, all mice received an intramuscular injection of 10 mg/kg profenid 50 mg/mL (Centravet; Lapalisse, France) for analgesic purpose then allowed to recover from surgery for 12 hours at 32° C. in a ventilated stove. Food and water were given ad libitum. Sham-operated mice underwent the same procedure without clamping.

At the end of the protocol, mice were sacrificed by lethal injection of pentobarbital (100 µL/10 g, Ceva Sante Animale; Libourne, France) 1 and 5 days after surgery.

Experimental methodology such as urea, creatinine, MPO and MDA as described in Example 2.

Analysis and Expression of Results

The results were given as mean values±standard error of the mean (SEM). A one-way ANOVA was used for comparison of within-group difference followed by a Newman-Keuls test for comparison of all pairs of columns (GraphPad Prism, San Diego, USA). A $p<0.05$ was accepted for statistical significance.

Results

Step 1: Determination of the Optimal Duration of Warm Renal Ischemia

Figure 12A:
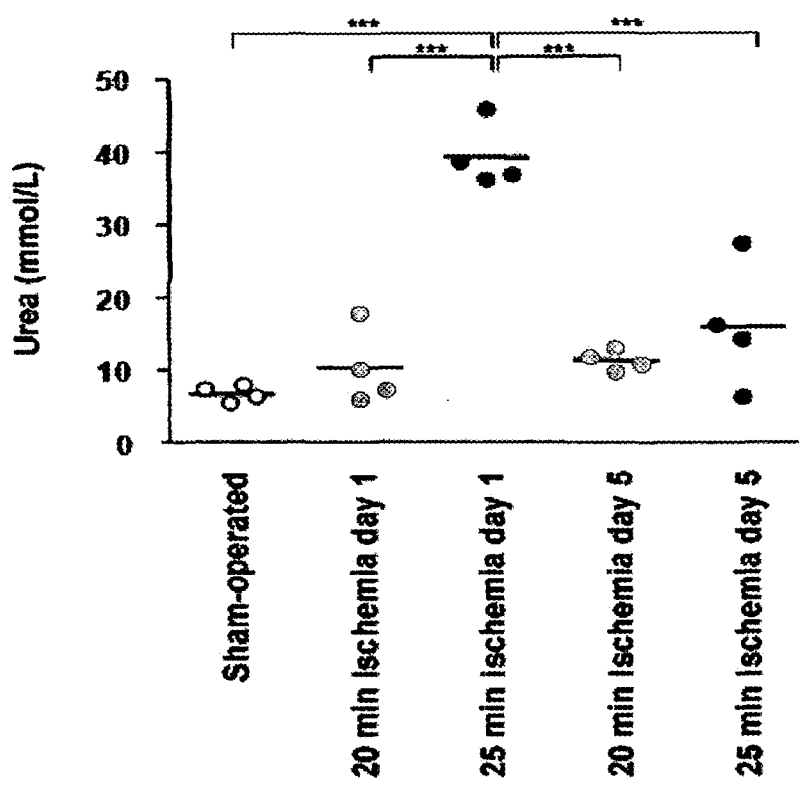
FIG. 12 shows dot plot graphs of measurements of (A) Uremia (urea (mmol/L)) and (B) Creatininemia (creatinine (mmol/L)) in mice kidney from Step 1 treatment groups 1 and 5 days after renal ischemia/reperfusion (n=4 per group)
Figure 12B:
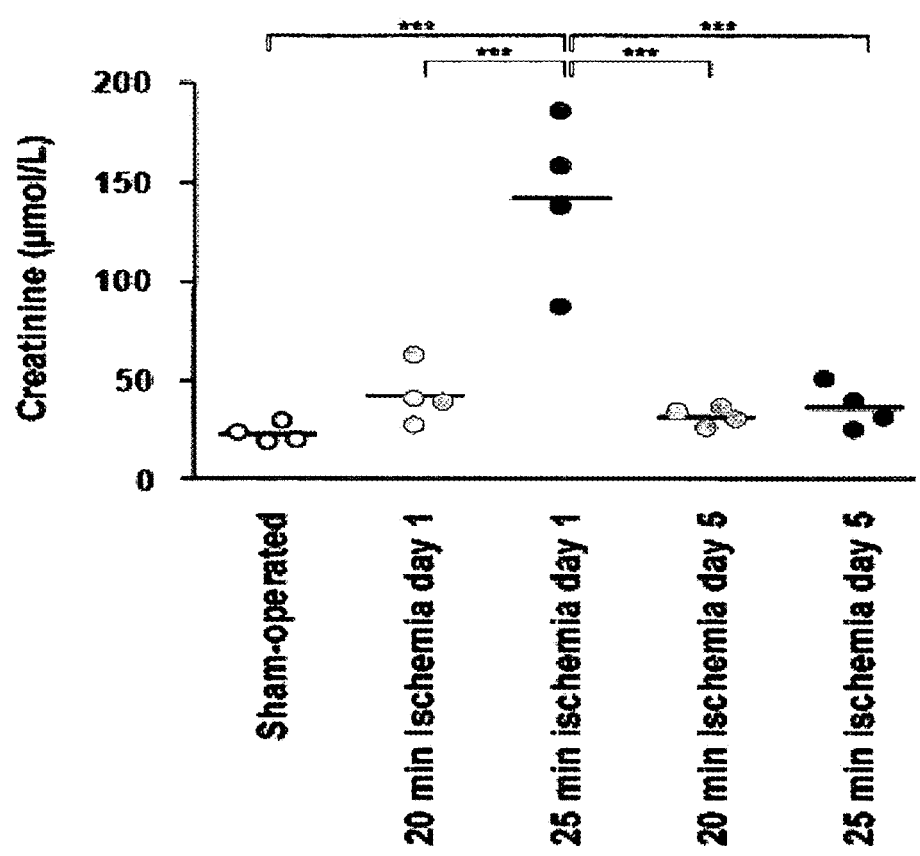

The functional impact of I/R was assessed by the measurement of key plasmatic parameters such as urea (FIG. 12(A)) and creatinine (FIG. 12(B), Table 4). No variation in the plasmatic parameter levels during the minute ischemia duration was noticed. However, it was demonstrated that when a 25 minute ischemia was performed, the loss of renal function then recovery that characterizes acute renal failure model was obtained. Indeed, one day after 25 minutes of ischemia, uremia and creatininemia were significantly increased as compared to sham-operated group, indicating renal function impairment (39.58±2.23 mmol/L urea and 142.18±20.74 µmol/L creatinine vs. 6.99±0.55 mmol/L urea and 23.20±2.44 µmol/L creatinine in 25 min ischemia day 1 and Sham-operated groups, respectively; ***$p<0.001$ compared to 25 min ischemia day 1 group; n=4 per group; ANOVA followed by Newman-Keuls test. Then, as expected, five days after ischemia, the plasmatic parameter levels returned to basal value (16.14±4.37 mmol/L urea and 36.83±5.52 µmol/L creatinine vs. 6.99±0.55 mmol/L urea and 23.20±2.44 µmol/L creatinine in 25 min ischemia day 5 and Sham-operated groups, respectively; n=4).

TABLE 4

Step 1: Individual data and mean results for the uremia (top) and creatininemia (bottom) at day 1 and day 5.

| | | Day 1 | | Day 5 | |
|---|---|---|---|---|---|
| | Sham-operated | 20 min ischemia | 25 min ischemia | 20 min ischemia | 25 min ischemia |
| | 7.59 | 10.45 | 37.05 | 10.97 | 6.35 |
| | 6.50 | 7.61 | 38.79 | 13.14 | 14.34 |
| | 5.69 | 6.26 | 36.40 | 11.99 | 16.33 |
| | 8.17 | 18.16 | 46.08 | 9.93 | 27.52 |
| Mean ± SEM | 6.99 ± 0.55 | 10.62 ± 2.66 | 39.58 ± 2.23 | 11.51 ± 0.69 | 16.14 ± 4.37 |
| | 19 | 39.3 | 137.8 | 36.6 | 25.2 |
| | 23.9 | 40.7 | 158.1 | 30.6 | 31.5 |
| | 20.1 | 27.4 | 87.3 | 34.4 | 39.9 |
| | 29.8 | 62.9 | 185.5 | 26 | 50.7 |
| Mean ± SEM | 23.20 ± 2.44 | 42.58 ± 7.40 | 142.18 ± 20.74 | 31.90 ± 2.33 | 36.83 ± 5.52 |

Figure 13A:
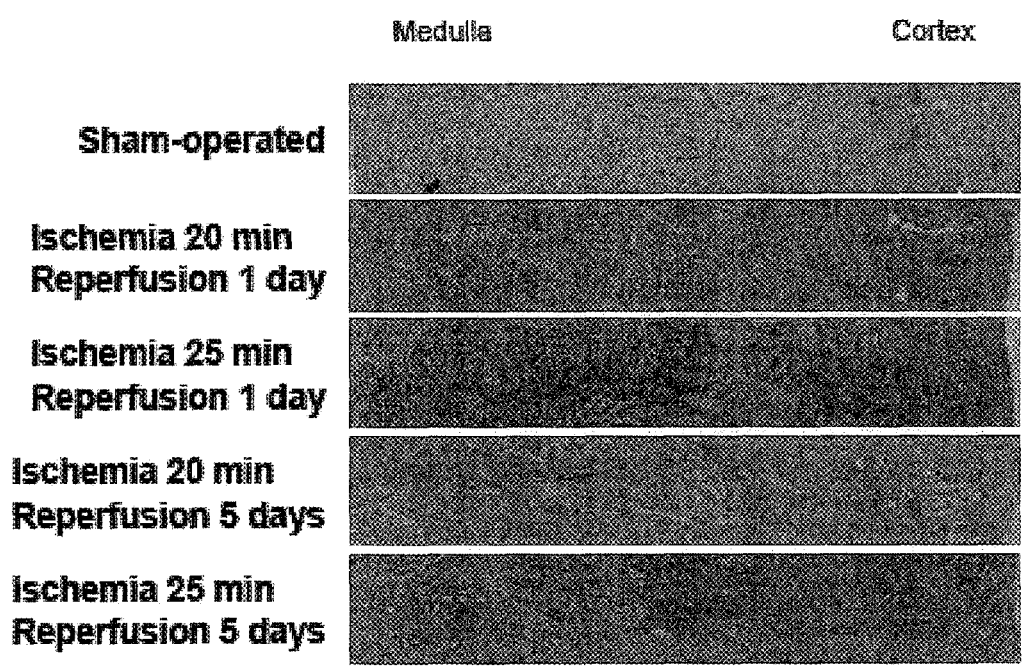
FIG. 13 shows (A) representative histological tubular kidney sections showing tubular injury, and (B) a dot plot graph of semi quantitative scoring of the percentage of damage tubules of mice from Step 1 treatment groups 1 and 5 days after renal ischaemia/repefusion (n=4 per group)
Figure 13B:
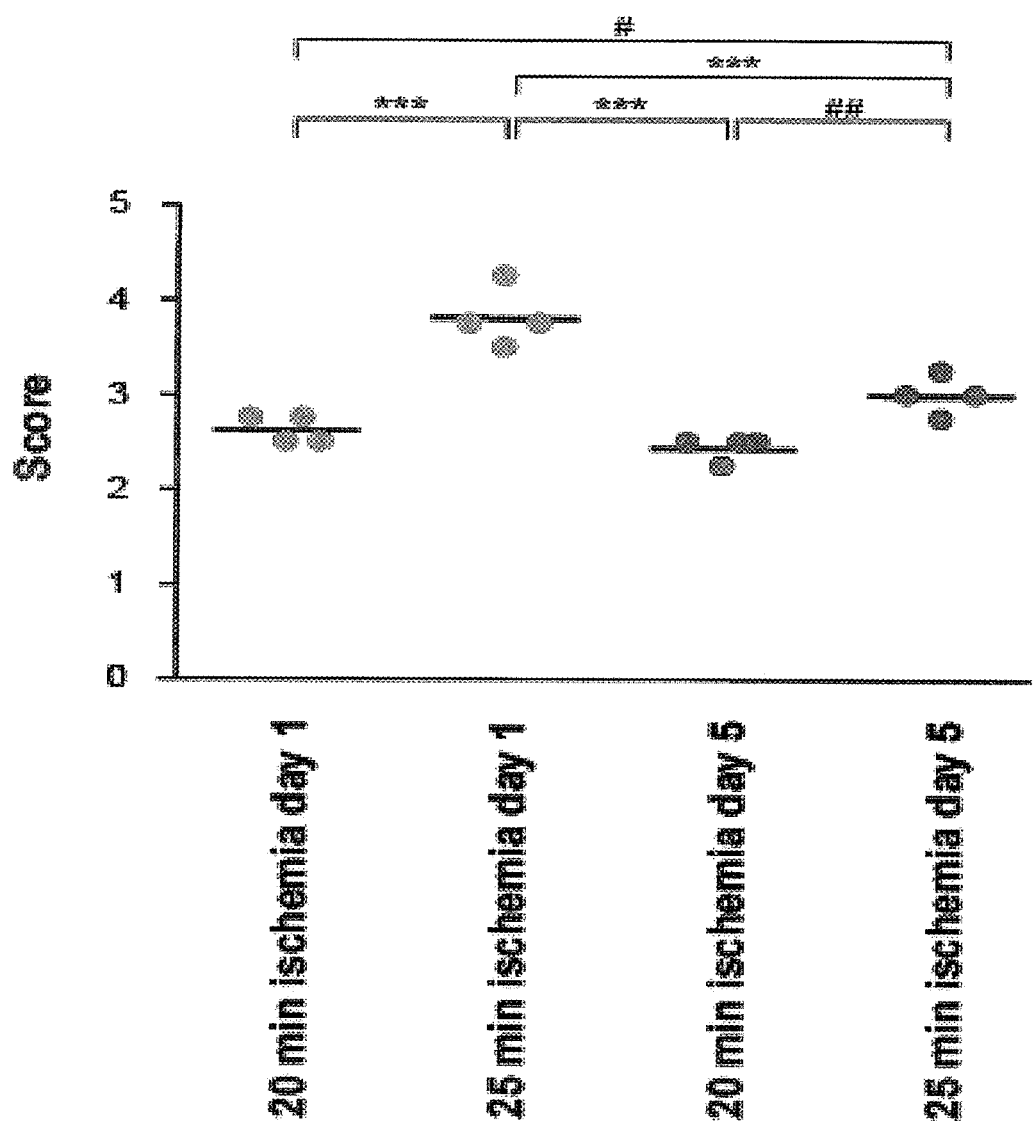

These functional modifications were correlated to structural damage as assessed by the percentage of damaged tubules (FIG. 13, Table 5). Data are expressed as the mean±SEM; #$p<0.05$, ##$p<0.01$ compared to 25 min ischemia day 5 group, ***$p<0.001$ compared to 25 min ischemia day 1 group; n=4 per group; ANOVA followed by Newman-Keuls test. One day after bilateral ischemia, the degree of tubular injury in kidney sections was significant and limited to the cortico-medullar junction. Five days after ischemia, tubular injury was still distinguishable but limited to the cortical area and associated with tubular regeneration. Lesions noticed at day 5 were less severe than those at day 1; for example, the losses of brush border or tubule cells as well as cast deposition were less/not detected as compared with tubular dilatation.

TABLE 5

Step 1: Individual data and mean results for the scoring of the percentage of damage tubules.

|  | Day 1 | | Day 5 | |
| --- | --- | --- | --- | --- |
| Sham-operated | 20 min ischemia | 25 min ischemia | 20 min ischemia | 25 min ischemia |
| 0 | 2.75 | 3.75 | 2.5 | 2.75 |
| 0 | 2.5 | 3.5 | 2.5 | 3.25 |
| 0 | 2.75 | 4.25 | 2.5 | 3 |
| 0 | 2.5 | 3.75 | 2.25 | 3 |
| Mean ± SEM: 0 | 2.63 ± 0.07 | 3.81 ± 0.16 | 2.44 ± 0.06 | 3.00 ± 0.10 |

It is noteworthy that, despite any functional impairment at both endpoints when 20 minute ischemia was performed, ischemic injury consequences were observed in the renal tissue. Moreover, 25 minute ischemia was necessary and sufficient to combine the reversibility of functional impairment with structural alterations, characteristic from acute renal failure. Finally, a 5 minute interval between 25 and 30 minutes was enough to convert an acute renal failure model in end stage renal disease for which no discrimination between treatments could be possible.

Figure 14A:
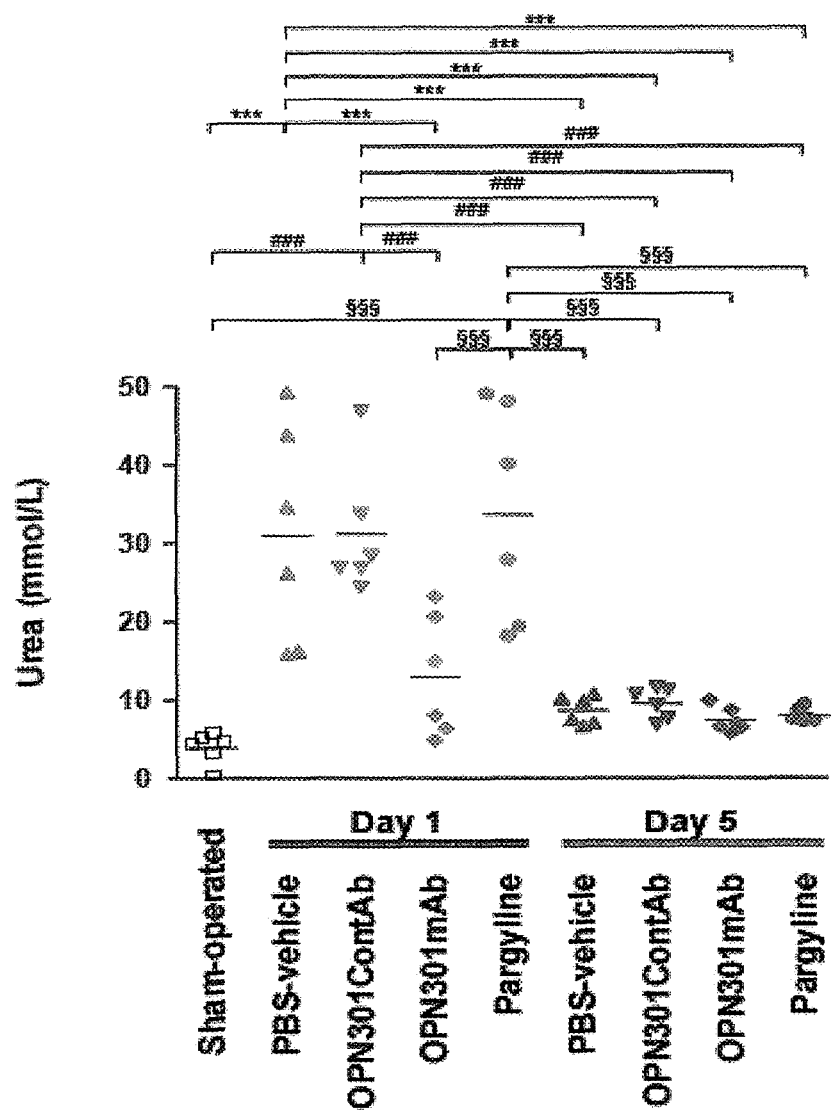
FIG. 14 shows dot plot graphs of measurements of (A) Uremia (urea (mmol/L)), and (B) Creatininemia (creatinine (mmol/L)) in mice kidney from Step 2 treatment groups as follows: (i) Sham-operated, (ii) PBS-vehicle, (iii) 10 mg/kg isotype control antibody (Control Ab), (iv) 10 mg/kg anti-TLR2 monoclonal antibody OPN301, and (v) 6 mg/kg pargyline measured 1 and 5 days after renal ischemia/reperfusion (n=6 per group)
Figure 14B:
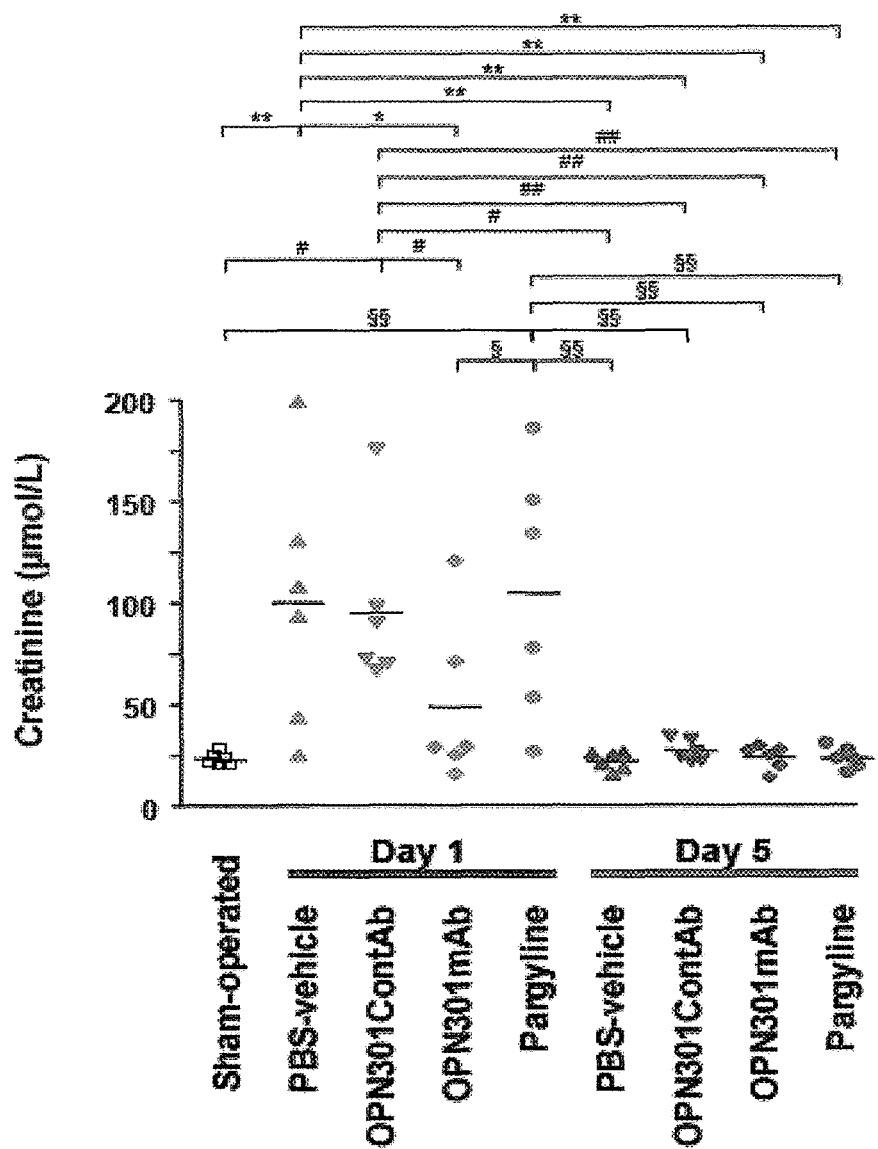

Step 2: Effects of OPN301 anti-TLR2 Monoclonal Antibody and Pargyline on Acute Renal Failure Plasmatic parameter follow up after 25 minute ischemia (FIGS. 14(A) and 14(B)) demonstrated that OPN301 anti-TLR2 monoclonal antibody had a preventive effect on renal function impairment induced by ischemic insult since uremia and creatininemia were not increased 1 day (D1) after ischemia when compared with the positive control group (13.10±3.15 mmol/L urea and 48.47±16.41 µmol/L creatinine vs. 31.05±5.70 mmol/L urea and 99.97±25.64 µmol/L creatinine in OPN301 anti-TLR2 monoclonal antibody D1 and PBS-vehicle D1 groups, respectively (Table 6 A & B). This effect was specific from OPN301 anti-TLR2 monoclonal antibody, as it was not observed for isotype control antibody (31.22±3.37 mmol/L urea and 95.55±16.80 µmol/L creatinine versus 31.05±5.70 mmol/L urea and 99.97±25.64 µmol/L creatinine in OPN301ContAb D1 and PBS-vehicle D1 groups, respectively, n=6), and also for pargyline (33.72±5.64 mmol/L urea and 104.7±25.20 µmol/L creatinine versus 31.05±5.70 mmol/L urea and 99.97±25.64 µmol/L creatinine in pargyline D1 and PBS-vehicle D1 groups, respectively; *$p<0.05$, $p<0.01$, *$p<0.001$ compared to PBS-vehicle D1 group, #$p<0.05$, ##$p<0.01$, #$p<0.001$ compared to the isotype control antibody D1 group, §$p<0.05$, §§$p<0.01$, §§§$p<0.001$ compared to Pargyline group; n=6 per group; ANOVA followed by Newman-Keuls test.

TABLE 6

Step 2: Individual data and mean results for the uremia (A) and creatininemia (B) 1 and 5 days after 25 minute ischemia.

A

| | Day 1 | | | | |
| --- | --- | --- | --- | --- | --- |
| | Sham-operated | PBS-vehicle | OPN301ContAb | OPN301mAb | Pargyline |
| | 4.47 | 43.83 | 46.83 | 8.13 | 47.99 |
| | 5.9 | 49.25 | 26.95 | 23.23 | 48.92 |
| | 0.54 | 16.37 | 33.73 | 15.08 | 40.01 |
| | 4.76 | 26.33 | 24.39 | 20.67 | 27.83 |
| | 3.47 | 34.62 | 26.92 | 6.51 | 19.35 |
| | 5.34 | 15.89 | 28.47 | 4.95 | 18.22 |
| Mean ± SEM | 4.08 ± 0.78 | 31.05 ± 5.70 | 31.22 ± 3.37 | 13.10 ± 3.15 | 33.72 ± 5.64 |

| | Day 5 | | | |
| --- | --- | --- | --- | --- |
| | PBS-vehicle | OPN301ContAb | OPN301mAb | Pargyline |
| | 7.62 | 10.87 | 6.65 | 7.63 |
| | 7.16 | 11.69 | 7.2 | 9.48 |
| | 9.99 | 9.48 | 10.03 | 7.37 |
| | 6.82 | 11.43 | 5.86 | 7.53 |
| | 10.82 | 7.83 | 6.71 | 8.78 |
| | 10.27 | 6.99 | 8.8 | 7.29 |
| Mean ± SEM | 8.78 ± 0.72 | 9.72 ± 0.80 | 7.54 ± 0.64 | 8.01 ± 0.37 |

B

| | Day 1 | | | | |
| --- | --- | --- | --- | --- | --- |
| | Sham-operated | PBS-vehicle | OPN301ContAb | OPN301mAb | Pargyline |
| | 20.3 | 130.9 | 175.6 | 29.2 | 185.9 |
| | 19.8 | 199.1 | 98.3 | 120.6 | 150.7 |
| | 24.6 | 43.5 | 90.2 | 28.9 | 134.1 |
| | 21.2 | 93.4 | 66.5 | 71.1 | 77.6 |
| | 28.1 | 108 | 72.5 | 25.2 | 53.3 |
| | 23.8 | 24.9 | 70.2 | 15.8 | 26.6 |
| Mean ± SEM | 22.97 ± 1.29 | 99.97 ± 25.64 | 95.55 ± 16.80 | 48.47 ± 16.41 | 104.7 ± 25.20 |

TABLE 6-continued

Step 2: Individual data and mean results for the uremia (A) and creatininemia (B) 1 and 5 days after 25 minute ischemia.

| | Day 5 | | | |
|---|---|---|---|---|
| | PBS-vehicle | OPN301ContAb | OPN301mAb | Pargyline |
| | 20.6 | 22.6 | 14 | 16 |
| | 15.5 | 24.4 | 19.8 | 27.2 |
| | 25.2 | 21.8 | 27.5 | 30.7 |
| | 26.4 | 26.9 | 24.9 | 19.2 |
| | 25.8 | 34.1 | 29.5 | 22.9 |
| | 18.3 | 32.7 | 26.9 | 22.9 |
| Mean ± SEM | 21.97 ± 1.84 | 27.08 ± 2.13 | 23.77 ± 2.37 | 23.15 ± 2.16 |

Figure 15:
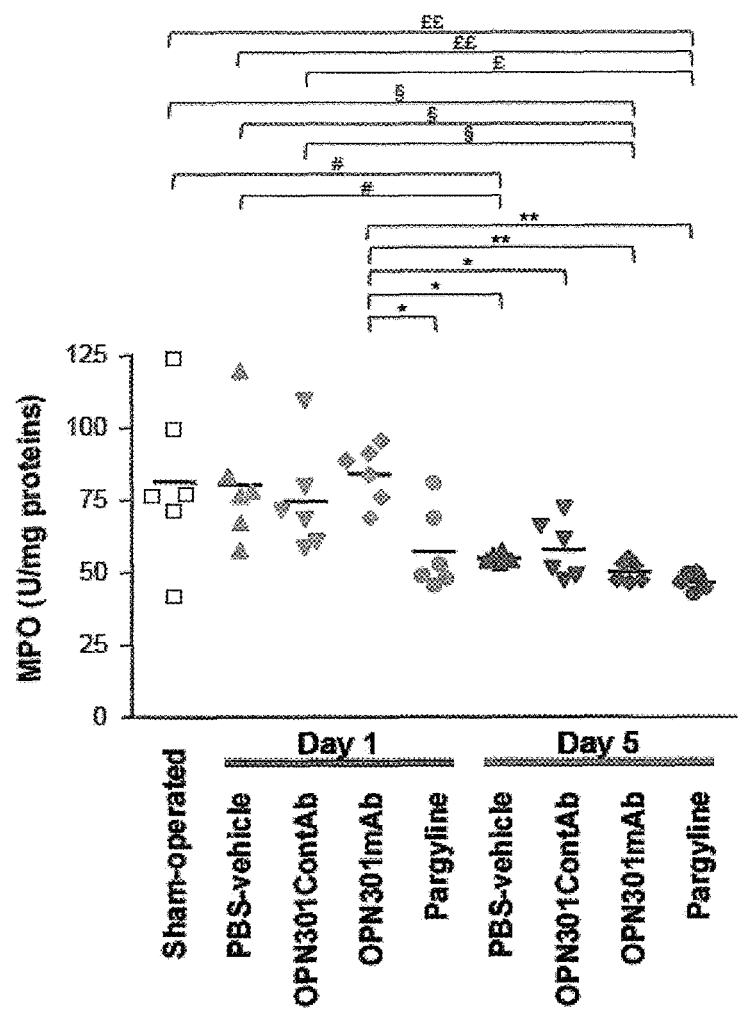
FIG. 15 shows a dot plot graph of accumulation of myeloperoxidase (MPO) (U/mg proteins) accumulation from neutrophils in mice from Step 2 treatment groups as follows: (i) Sham-operated, (ii) PBS-vehicle, (iii) 10 mg/kg isotype control antibody (Control Ab), (iv) 10 mg/kg anti-TLR2 monoclonal antibody OPN301, and (v) 6 mg/kg pargyline measured 1 and 5 days after renal ischaemia/repefusion (n=6 per group)
Figure 16:
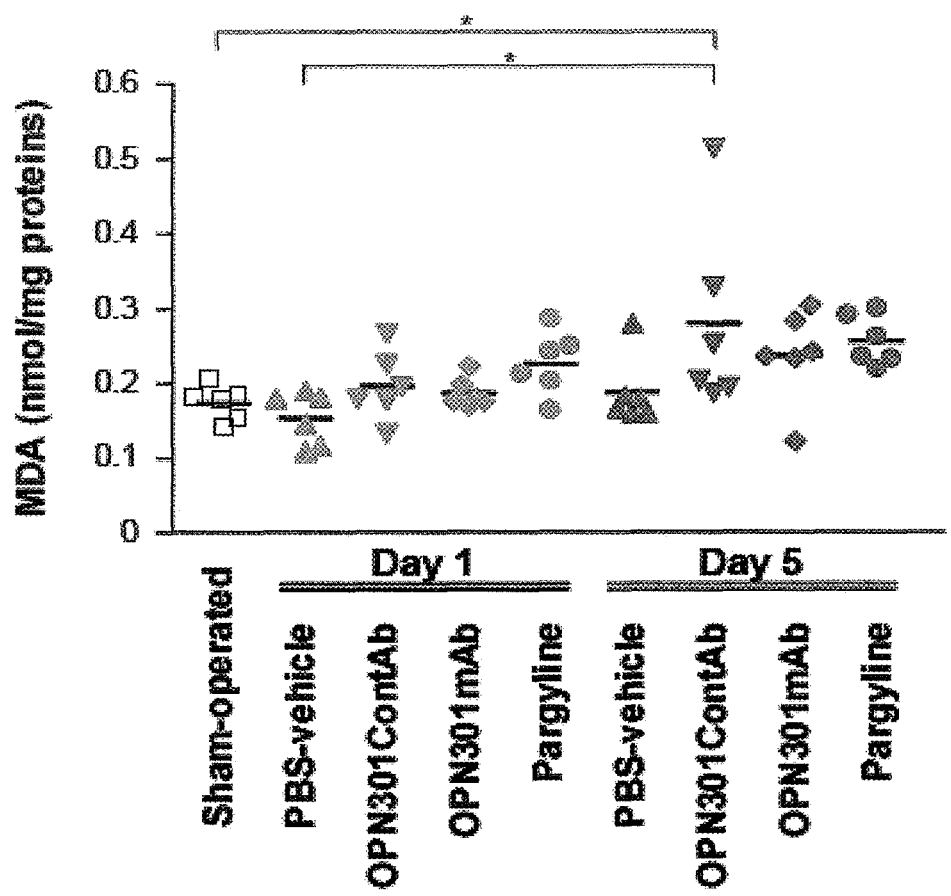
FIG. 16 shows a dot plot graph indicating malondialdehyde (MDA) production which is used as an index of lipid peroxidation (nmol/mg proteins) in mice kidney in Step 2 treatment groups as follows: (i) Sham-operated, (ii) PBS-vehicle, (iii) 10 mg/kg isotype control antibody (Control Ab), (iv) 10 mg/kg anti-TLR2 monoclonal antibody OPN301, and (v) 6 mg/kg pargyline measured 1 and 5 days after renal ischaemia/repefusion (n=6 per group)

At day 5, there was no difference between treatments; as expected, the regeneration step was functionally engaged. Considering parameters related to inflammation, mainly neutrophil accumulation in renal tissue (FIG. 15, Table 7), no modification in MPO activity was evidenced when compared with PBS-vehicle group 1 day after ischemia (84.03±4.10 U MPO/mg protein vs. 80.45±8.66 U MPO/mg protein in OPN301 anti-TLR2 monoclonal antibody D1 and PBS-vehicle D1 groups, respectively; $^£p<0.05$, $^{££}p<0.01$ compared to Pargyline D5 group. $^§p<0.05$ compared to OPN301 anti-TLR2 monoclonal antibody D5 group. $^#p<0.05$ compared to PBS-vehicle D5 group, *p<0.05, **p<0.01 compared to OPN301 anti-TLR2 monoclonal antibody D1 group; n=6 per group; ANOVA followed by Newman-Keuls test. At the same endpoint, the reference substance treatment with pargyline had a strongest effect on this parameter when compared to the OPN301 anti-TLR2 monoclonal antibody (57.37±5.78 U MPO/mg protein vs. 84.03±4.10 U MPO/mg protein in Pargyline D1 (day 1) and OPN301 anti-TLR2 monoclonal antibody (OPN301 mAb) D1 (day 1) groups, respectively. Five days after ischemia, MPO activity in renal tissue was decreased in the four different groups when compared to the PBS-vehicle D1 group.

TABLE 7

Individual data and mean results for the MPO activity as an index of neutrophil accumulation after 1 and 5 days.

| | Day 1 | | | | |
|---|---|---|---|---|---|
| | Sham-operated | PBS-vehicle | OPN301ContAb | OPN301mAb | Pargyline |
| | 124 | 76.6 | 68.4 | 91.3 | 48.8 |
| | 41.5 | 67.1 | 71.6 | 76.1 | 45.4 |
| | 70.9 | 119.6 | 79.8 | 83.7 | 47.9 |
| | 76.3 | 83.3 | 109.5 | 88.6 | 52.7 |
| | 99.6 | 57.9 | 58.7 | 95.7 | 68.7 |
| | 77 | 78.2 | 60.7 | 68.8 | 80.7 |
| Mean ± SEM | 81.55 ± 11.39 | 80.45 ± 8.66 | 74.78 ± 7.61 | 84.03 ± 4.10 | 57.37 ± 5.78 |

| | Day 5 | | | |
|---|---|---|---|---|
| | PBS-vehicle | OPN301ContAb | OPN301mAb | Pargyline |
| | 54.1 | 72.1 | 54.8 | 44.4 |
| | 53.1 | 51.4 | 47.2 | 49.2 |
| | 55.9 | 47.1 | 52.4 | 47.6 |
| | 55 | 66 | 52.8 | 42.2 |
| | 57.4 | 49 | 47.3 | 46.3 |
| | 54.2 | 61.5 | 46.3 | 49.6 |
| Mean ± SEM | 54.95 ± 0.62 | 57.85 ± 4.16 | 50.13 ± 1.48 | 46.55 ± 1.17 |

Statistical analyses were performed using one-way ANOVA followed by Newman-Keuls test.

TABLE 8

Individual data and mean results for the MDA level as an index of lipid peroxidation.

| | Day 1 | | | | |
|---|---|---|---|---|---|
| | Sham-operated | PBS-vehicle | OPN301ContAb | OPN301mAb | Pargyline |
| | 0.178 | 0.179 | 0.179 | 0.197 | 0.249 |
| | 0.183 | 0.116 | 0.132 | 0.176 | 0.202 |
| | 0.181 | 0.108 | 0.196 | 0.222 | 0.285 |
| | 0.204 | 0.145 | 0.225 | 0.175 | 0.163 |

TABLE 8-continued

Individual data and mean results for the MDA level as an index of lipid peroxidation.

|  | | | | | |
|---|---|---|---|---|---|
| | 0.153 | 0.181 | 0.177 | 0.180 | 0.212 |
| | 0.141 | 0.189 | 0.266 | 0.169 | 0.242 |
| Mean ± SEM | 0.173 ± 0.009 | 0.153 ± 0.014 | 0.196 ± 0.019 | 0.187± 0.008 | 0.225 ± 0.017 |

Day 5

|  | PBS-vehicle | OPN301ContAb | OPN301mAb | Pargyline |
|---|---|---|---|---|
| | 0.160 | 0.513 | 0.303 | 0.290 |
| | 0.159 | 0.187 | 0.121 | 0.231 |
| | 0.166 | 0.252 | 0.283 | 0.218 |
| | 0.182 | 0.194 | 0.241 | 0.261 |
| | 0.179 | 0.328 | 0.235 | 0.234 |
| | 0.279 | 0.203 | 0.232 | 0.299 |
| Mean ± SEM | 0.188 ± 0.019 | 0.279 ± 0.051 | 0.236 ± 0.026 | 0.255 ± 0.014 |

Figure 17:
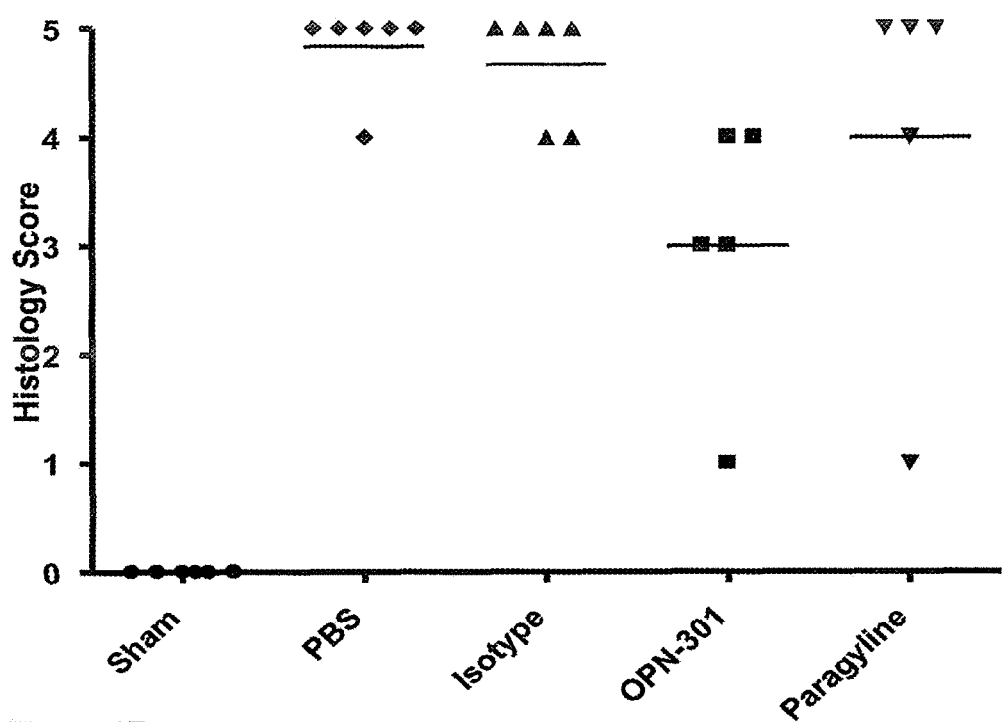
FIG. 17 shows a dot plot graph of semi quantitative scoring of the damage to tubules of mice from Step 2 treatment groups as follows: (i) Sham-operated, (ii) PBS-vehicle, (iii) 10 mg/kg isotype control antibody (Control Ab), (iv) 10 mg/kg anti-TLR2 monoclonal antibody OPN301, and (v) 6 mg/kg pargyline measured 1 and 5 days after renal ischaemia/repefusion (n=6 per group), FIGS. 18(a), (b) and (c) show a dot plots of accumulation of µ-GST µg/L in mice kidney from Step 2 treatment groups (i) Sham-operated (ii) PBS-vehicle iii) 10 mg/kg isotype control antibody (Control Ab), (iv) 10 mg/kg OPN301 mAb and (v) 6 mg/kg pargyline measured 1 day after renal ischemia/reperfusion at day 0 (FIG. 18(a)), day 1 (FIG. 18(b)) and day 5 (FIG. 18(c)) after renal ischemia/reperfusion (n=6 per group)
Figure 18A:
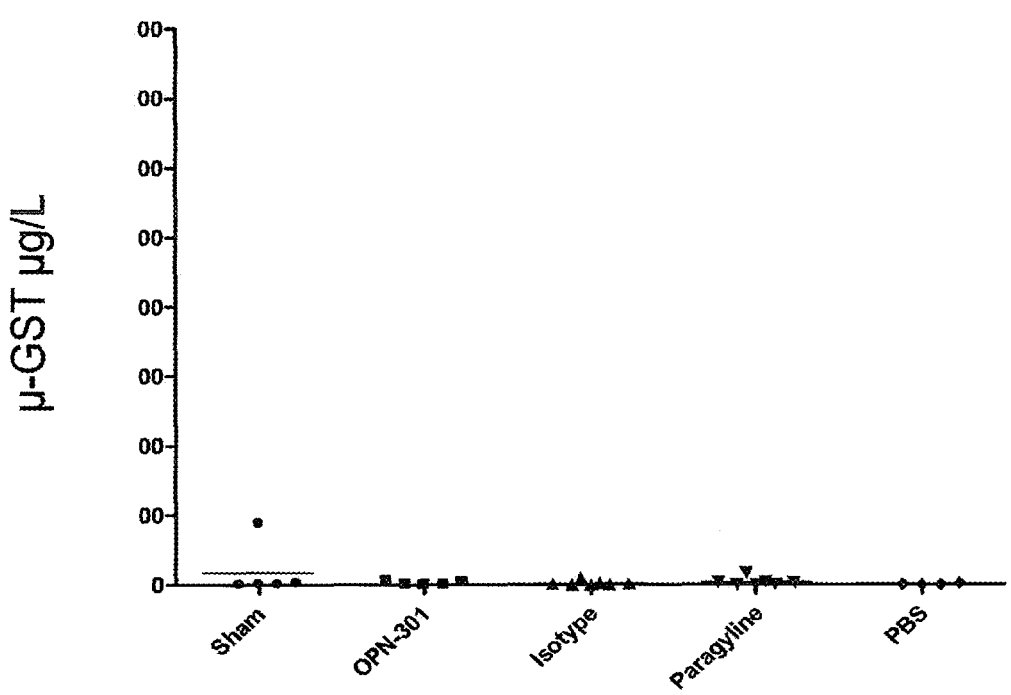
Figure 18B:
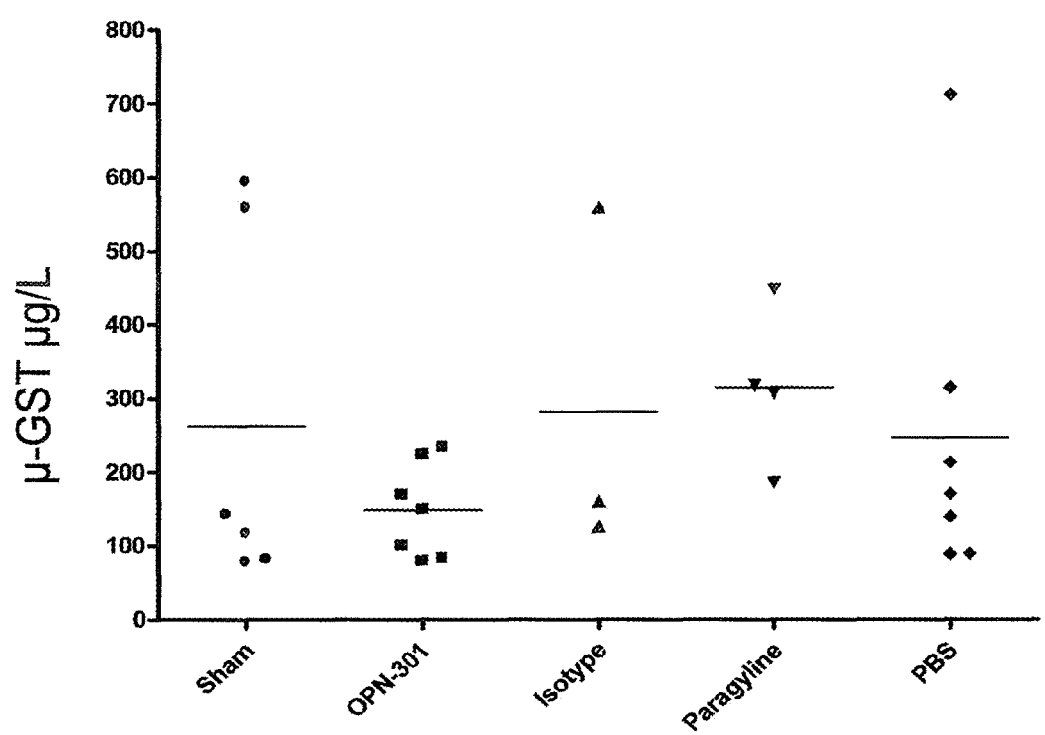
Figure 18C:
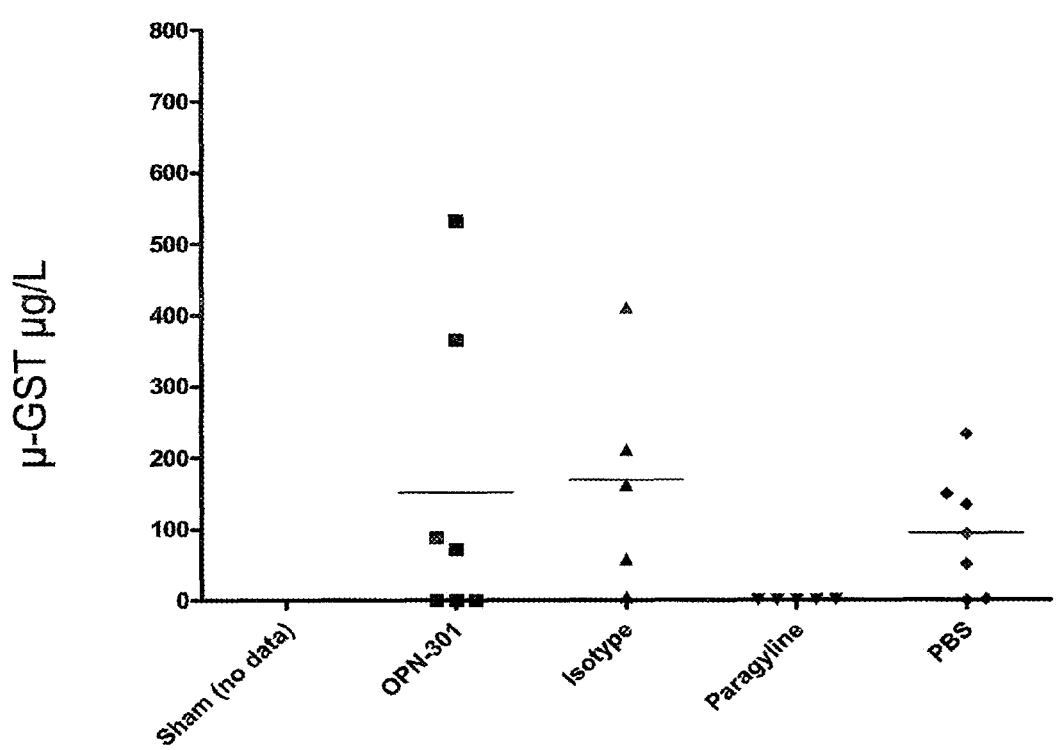

FIG. 17 indicates the degree of tubular injury in the kidney by measuring histological scores. One day after bilateral I/R, the degree of tubular injury in control and PBS-vehicle samples where severe compared with OPN301 mAb; (n=6 per group, ***p<0.01, ANOVA with Newman-Keuls test). μ-GST μg/L, an indicator of tubular damage in mice kidney was measured at day 0, day 1 and day 5 after renal ischemia/reperfusion (FIG. 18)

Conclusion

In the present study it was shown, for the first time in mice, that the optimal duration of renal warm ischemia is 25 minutes. This protocol induced clear renal function impairment at day 1 followed by recovery at day 5, as expected in an acute renal failure model. From a structural point of view, when 25 minute ischemia was performed, tubular damages were only restricted to the cortico-medullar junction at day 1 before affecting the cortical area and regenerating at day 5. Second, our functional results in Step 2 demonstrated that the treatment with OPN301 anti-TLR2 monoclonal antibody 10 mg/kg had a protective and specific effect against renal function alterations induced by ischemic injury 1 day after ischemia. The results of neutrophil accumulation (MPO) and oxidative stress (MDA) did not reveal any positive effects of OPN301 mAb treatment. However, the fact that we also did not observe significant differences between sham and ischemia-reperfusion animals (which is unusual) suggests that different experimental conditions (for instance, different time-course of ischemia-reperfusion) may be necessary. Moreover, the fact that the treatment with pargyline was without effects, in sharp contrast to our previous studies using the I/R model in rats (Kunduzova et al., 2002) suggest that species differences should be taken into account. In conclusion, this study is the first proof of concept for the use of OPN301 anti-TLR2 monoclonal antibody in the treatment of acute renal failure, i.e. 1 day after ischemia.

The invention claimed is:

1. A method for the treatment of a renal disorder, the method comprising administering a therapeutically effective amount of an antibody or an antigen binding fragment thereof, which has binding specificity for Toll-like Receptor 2 and which is an antagonist of the function of Toll-like Receptor 2, to a subject in need of such treatment, wherein said subject has not been administered said antibody or antigen binding fragment thereof prior to the onset of the renal disorder.

2. The method as claimed in claim 1 wherein the antibody is selected from the group consisting of a monoclonal antibody, a polyclonal antibody and a synthetic antibody, or an antigen binding fragment of any of same.

3. The method as claimed in claim 1, wherein the antibody is selected from the group consisting of a human antibody, a humanised antibody, a camelid antibody and in vitro generated antibody to human TLR2, or an antigen binding fragment of any of same.

4. The method as claimed in claim 1 wherein the antibody or antigen binding fragment thereof binds to an inhibitory epitope present on TLR2 with a dissociation constant (Kd) of from about $10^{-7}$ M to about $10^{-11}$ M.

5. The method as claimed in claim 1, wherein the antibody or antigen binding fragment thereof binds to an epitope defined by the extracellular domain of human TLR2.

6. The method as claimed in claim 1 wherein the antibody or antigen binding fragment thereof is administered to the subject in order to reduce or inhibit one or more TLR2 biological activities in a TLR2 expressing cell, wherein the cell is a cell selected from the group consisting of a renal tubular epithelial cell, an epithelial cell of the Bowman's capsule, a kidney glomerulus parietal cell, a kidney glomerulus podocyte, a kidney proximal tubule brush border cell, a loop of henle thin segment cell, a kidney distal tubule cell and a kidney collecting duct cell.

7. The method as claimed in claim 1 wherein the renal disorder is selected from the group consisting of renal disease, chronic renal failure, acute renal failure heterologous nephrotoxic nephritis, glomerulonephritis, sclerosis of the glomerulus, systemic lupus erythematosus (SLE), diabetic nephropathy and diabetic nephropathy.

8. The method as claimed in claim 1 wherein the renal disorder is selected from the group consisting of Immunoglobulin A nephropathy, membranoproliferative glomerulonephritis, mesangial proliferative glomerulonephritis, nonproliferative glomerulonephritis, membranous glomerulonephritis, minimal-change disease, primary focal segmental glomerulosclerosis, fibrillary glomerulonephritis, immunotactoid glomerulonephritis, proliferative glomerulonephritis, progressive glomerulonephritis, anti-GBM disease, kidney ischemia, delayed graft function, kidney vasculitis, including disease associated with anti-neutrophil cytoplasmic antibodies, lupus nephritis cryoglobulinemia-associated glomerulonephritis, bacterial endocarditis, Henoch-Schönlein purpura, postinfectious glomerulonephritis, Hepatitis C disease, diabetic nephropathy, myloidosis, hypertensive nephrosclerosis, light-chain disease from multiple myeloma, secondary focal glomerulosclerosis and hypertensive nephrosclerosis.

9. The method as claimed in claim 1 wherein the TLR2 is human TLR2 or murine TLR2.

10. The method as claimed in claim 1 further comprising the step of administering a therapeutically effective amount of at least one secondary therapeutic compound, said secondary therapeutic compound being an immunosuppressant compound.

11. The method as claimed in claim 10 wherein the secondary therapeutic compound is selected from the group consisting of a glucocorticoid, a cytostatic, an anti-metabolite, an anti-CD2 antibody or related binding fragment, an anti-CD20 antibody, an anti-Tumor Necrosis Factor-alpha (TNF-alpha) antibody, cyclosporine, tacrolimus, sirolimus and Fingolimod (FTY720).

12. The method as claimed in claim 1 wherein the renal disorder is ischemia reperfusion injury.

13. The method as claimed in claim 12 wherein the ischemia reperfusion injury results from kidney organ transplantation in the subject.

14. The method as claimed in claim 1 wherein the renal disorder is glomerulonephritis.

15. The method as claimed in claim 1 wherein the antibody or antigen binding fragment thereof blocks binding of TLR2 activating ligands which have binding specificity to TLR2.

* * * * *